(12) United States Patent
Cheney et al.

(10) Patent No.: US 11,793,586 B2
(45) Date of Patent: Oct. 24, 2023

(54) SYSTEMS, DEVICES, AND METHODS FOR MEASUREMENT AND TREATMENT OF TISSUE WITH FORCE CONTROL AND FEEDBACK

(71) Applicant: Impact Biosystems, Inc., Boston, MA (US)

(72) Inventors: Craig Cheney, Somerville, MA (US); Ian Hunter, Lincoln, MA (US); Geehoon Park, Acton, MA (US)

(73) Assignee: Impact Biosystems, Inc., Boston, MA (US)

( * ) Notice: Subject to any disclaimer, the term of this patent is extended or adjusted under 35 U.S.C. 154(b) by 0 days.

(21) Appl. No.: 17/845,713

(22) Filed: Jun. 21, 2022

(65) Prior Publication Data
US 2022/0313377 A1 Oct. 6, 2022

Related U.S. Application Data

(63) Continuation of application No. PCT/US2021/053799, filed on Oct. 6, 2021.
(Continued)

(51) Int. Cl.
*A61H 23/02* (2006.01)
*A61B 34/30* (2016.01)

(52) U.S. Cl.
CPC ............ *A61B 34/30* (2016.02); *A61H 23/02* (2013.01); *A61H 2201/5061* (2013.01); *A61H 2230/605* (2013.01)

(58) Field of Classification Search
CPC ...... A61H 23/00; A61H 23/02; A61H 23/008; B65D 17/24
See application file for complete search history.

(56) References Cited

U.S. PATENT DOCUMENTS

| | | | | |
|---|---|---|---|---|
| 1,599,628 A | * | 9/1926 | Ahlgren | A61H 9/005 601/108 |
| 2,067,991 A | * | 1/1937 | Taylor | A61H 9/005 601/111 |

(Continued)

FOREIGN PATENT DOCUMENTS

| | | | | |
|---|---|---|---|---|
| CN | 1119933 A | * | 4/1996 | ......... A61H 23/0254 |
| CN | 101396591 A | * | 4/2009 | ......... A61H 23/0245 |

(Continued)

OTHER PUBLICATIONS

International Search Report and Written Opinion for International Application No. PCT/US2021/053799, dated Feb. 10, 2022, 18 pages.
(Continued)

*Primary Examiner* — Michael J Tsai
(74) *Attorney, Agent, or Firm* — COOLEY LLP

(57) ABSTRACT

Systems, devices, and methods are described herein that relate to massage devices with force control and feedback for providing pain relief and improved muscle recover to users. The massage devices can output mechanisms for applying a mechanical output to a muscle area of a user to treat a muscle condition, driving mechanisms for driving the movement of the output mechanisms, and sensors for measuring force and other properties associated with application of the mechanical output. The massage devices can be configured to adapt therapy being applied to a muscle area or provide users with feedback based on sensor measurements.

30 Claims, 25 Drawing Sheets

Related U.S. Application Data

(60) Provisional application No. 63/116,546, filed on Nov. 20, 2020, provisional application No. 63/088,250, filed on Oct. 6, 2020.

(56) References Cited

U.S. PATENT DOCUMENTS

| | | | | |
|---|---|---|---|---|
| 4,088,128 | A * | 5/1978 | Mabuchi | A61H 23/0254 601/108 |
| 4,513,737 | A * | 4/1985 | Mabuchi | A61H 23/0254 601/108 |
| 4,566,442 | A * | 1/1986 | Mabuchi | A61H 23/0254 601/101 |
| 4,716,890 | A * | 1/1988 | Bichel | A61H 23/04 601/108 |
| 5,140,979 | A * | 8/1992 | Nakagawa | A61N 1/10 128/907 |
| 5,593,381 | A * | 1/1997 | Tannenbaum | A61H 23/0218 601/134 |
| 6,132,385 | A * | 10/2000 | Vain | A61B 5/103 600/553 |
| 6,423,014 | B1 | 7/2002 | Churchill et al. | |
| 7,079,898 | B2 * | 7/2006 | Cohn | A61F 7/007 607/45 |
| 9,808,158 | B2 * | 11/2017 | Peipsi | A61B 5/442 |
| 9,808,183 | B2 * | 11/2017 | Vain | A61B 9/00 |
| 10,568,561 | B2 * | 2/2020 | Peipsi | A61B 5/4519 |
| 10,682,281 | B2 * | 6/2020 | Smith, Jr. | A61H 1/00 |
| 10,806,660 | B1 * | 10/2020 | Smith, Jr. | A61H 1/00 |
| 2006/0052729 | A1 * | 3/2006 | Gurses | A61B 5/0053 600/557 |
| 2011/0054367 | A1 * | 3/2011 | Schulz | A61H 23/008 601/46 |
| 2015/0374275 | A1 * | 12/2015 | Peipsi | A61B 5/442 600/587 |

FOREIGN PATENT DOCUMENTS

| | | | | |
|---|---|---|---|---|
| GB | 2287887 | A * | 10/1995 | A61H 23/0254 |
| JP | 2014217409 | A * | 11/2014 | A61H 23/02 |
| KR | 20130004722 | | * 8/2013 | A61H 23/02 |
| WO | WO-2009121431 | A1 * | 10/2009 | B25D 16/003 |
| WO | WO-2013040451 | A2 | 3/2013 | |
| WO | WO-2014028843 | A1 * | 2/2014 | A61F 7/007 |

OTHER PUBLICATIONS

Ishii, H. & Nishida,Y., "Effect of Lactate Accumulation during Exercise-induced Muscle Fatigue on the Sensorimotor Cortex," J. Phys. Ther. Sci., 25:1637-1642 (2013).

* cited by examiner

SYSTEMS, DEVICES, AND METHODS FOR MEASUREMENT AND TREATMENT OF TISSUE WITH FORCE CONTROL AND FEEDBACK

CROSS-REFERENCE TO RELATED APPLICATIONS

This application is a continuation of International Patent Application No. PCT/US2021/05379, entitled "Systems, Devices, and Methods for Measurement and Treatment of Tissue with Force Control and Feedback," filed Oct. 6, 2021, which claims the benefit of U.S. Provisional Patent Application Ser. No. 63/088,250, entitled "Percussive Massage Devices with Force Control and Feedback and Systems and Methods thereof," filed Oct. 6, 2020, and U.S. Provisional Patent Application Ser. No. 63/116,546, entitled "Dual Actuator, Long Stroke, High Force, High Bandwidth Massager," filed Nov. 20, 2020, the disclosure of each of which is incorporated by reference herein in its entirety.

BACKGROUND

Intense physical activity may lead to various medical conditions including dehydration, hypothermia, musculoskeletal injuries, heat stroke, fever, and vomiting. However, more frequently, symptoms of intense physical activity include muscle fatigue and pain. The development of muscle fatigue and pain during and/or after physical activity may be related to muscle damage, which can induce inflammatory response, soreness, stiffness, and over time can lead to injuries. The onset of injuries, particularly in athletes, can impair performance, delay training, extend the time required to recover, and in some extreme cases lead to permanent disability. Consequently, there is a need to develop approaches to treat the effects of muscle fatigue and provide pain relief associated with intense physical activity.

SUMMARY

Apparatus and methods are described herein for applying therapy to treat muscle conditions with feedback and force control.

In an embodiment, an apparatus includes an output mechanism including a tip configured to apply a mechanical output to a muscle area of a user to treat a condition associated with the muscle area; a driving mechanism coupled to the output mechanism, the driving mechanism configured to drive mechanical motion of the output mechanism to produce the mechanical output; a sensor configured to measure a property associated with at least one of the output shaft or the driving mechanism; and a processor operatively coupled to the sensor, the processor configured to: receive, from the sensor, data representative of the property; determine, based on the data, a force associated with the application of the mechanical output to the muscle area; and in response to the force being outside of a predefined range: adjust at least one parameter of the mechanical output such that the mechanical output is adapted to treat the condition associated with the muscle area, or provide feedback to the user that informs the user to adjust the application of the mechanical output to the muscle area.

In an embodiment, a method includes receiving, from a sensor, data representative of a property associated with a massage device, the massage device configured to generate a mechanical output and apply the mechanical output to a muscle area of a user to treat a condition associated with the muscle area; determining, based on the data, a force associated with the application of the mechanical output to the muscle area; determining, based on the force, that a different application of the mechanical output to the muscle area is required to treat the condition associated with the muscle area; and in response to determining that a different application is required: adjusting at least one parameter of the mechanical output such that the mechanical output is adapted to treat the condition associated with the muscle area, or providing feedback to the user that informs the user to adjust the application of the mechanical output to the muscle area.

In an embodiment, an apparatus includes: an output mechanism including an end effector configured to apply a mechanical output to a muscle area of a user; a driving mechanism coupled to the output mechanism, the driving mechanism configured to drive mechanical motion of the output mechanism to produce the mechanical output; a shroud disposed around at least a portion of the output mechanism, the shroud including a surface configured to contact a skin of the user above the muscle area; a sensor configured to measure a property associated with the output mechanism; and a processor operatively coupled to the sensor and the driving mechanism, the processor configured to: control the driving mechanism to drive movement of the output mechanism for a predetermined period of time; receive, from the sensor during the predetermined period of time, data representative of the property over time; and determine, based on the data over time, a characteristic of the muscle area of the user.

In an embodiment, an apparatus includes: an output mechanism including an end effector configured to apply a mechanical output to a muscle area of a user to treat a condition associated with the muscle area; a driving mechanism coupled to the output mechanism, the driving mechanism configured to drive mechanical motion of the output mechanism to produce the mechanical output; a housing that houses the driving mechanism and includes an opening through which a portion of the output mechanism extends, the output mechanism being movable relative to the housing to apply the mechanical output to the muscle area; a sensor coupled to the housing and configured to measure a movement or acceleration of the housing; and a processor operatively coupled to the sensor and the driving mechanism, the processor configured to: receive, from the sensor, data indicative of the movement or the acceleration of the housing; and in response to the data indicating that the movement or the acceleration of the housing is greater than a predefined threshold: control the driving mechanism to adjust or pause the mechanical motion of the output mechanism; or provide feedback to the user that informs the user to adjust the application of the mechanical output to the muscle area.

In an embodiment, a system includes: a muscle measurement device configured to measure data indicative of a characteristic of a muscle area of a user; a muscle treatment device configured to apply a therapy to the muscle area based at least in part on the measured characteristic of the muscle area; and a processor operatively coupled to the muscle management device and the muscle treatment device, the processor configured to: receive data from a sensor associated with the muscle measurement device, the sensor configured to measure a property associated with an end effector of the muscle measurement device that contacts a tissue surface over the muscle area; determine, based on the data received from the sensor, the characteristic of the muscle area; and send instructions for controlling the muscle treatment device based on the characteristic of the muscle area.

In an embodiment, a method includes: receiving, from a sensor, data representative of a property associated with an end effector that is in contact with tissue overlaying a muscle area, the end effector configured to generate and apply a mechanical output to the tissue; determining, based at least in part on the data, a characteristic of the muscle area; and determining, based on the characteristic of the muscle area, one or more parameters of a treatment plan for treating a condition associated with the muscle area. In an embodiment, a method includes: receiving, from a first sensor, data representative of a property associated with an end effector that is in contact with tissue overlaying a muscle area, the end effector configured to generate and apply a mechanical output along a primary axis to the tissue; receiving, from a second sensor, data representative of a property associated with a moving shroud that is in contact with the tissue and configured to displace in a direction along the primary axis; and determining, based on the data from the first and second sensors, a characteristic of the muscle area.

DETAILED DESCRIPTION

Figure 1:
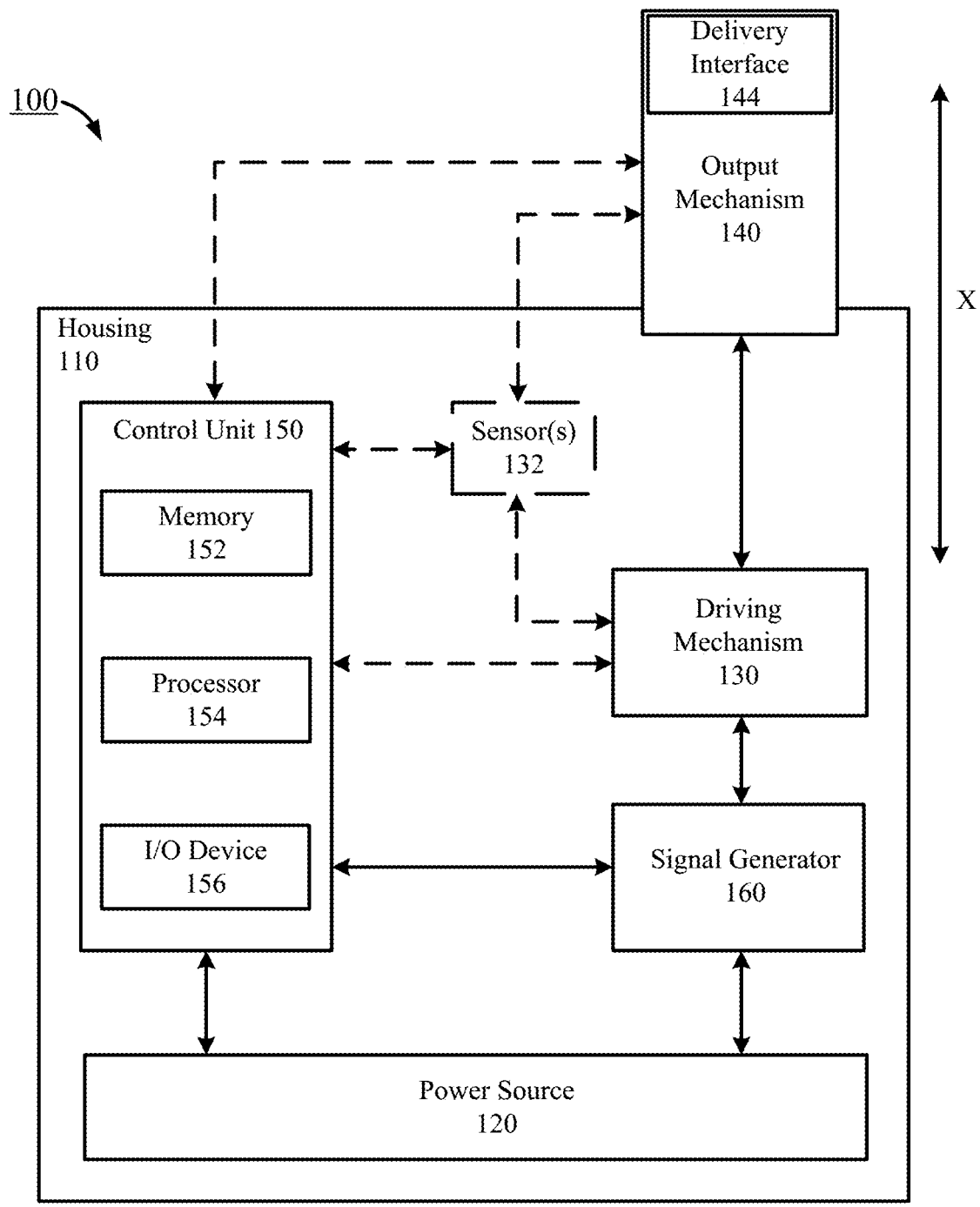
FIG. 1 is a schematic illustration of a muscle management device according to an embodiment.

The embodiments described herein relate generally to systems, devices, and methods for measuring characteristics of tissue and/or treating (e.g., massaging) tissue, and more particularly to handheld muscle measurement and/or treatment devices with force control and feedback that can be used to provide pain relief and improved muscle recovery to users.

Strenuous physical activity can lead to insufficient oxygen supply to meet the energetic demands of the body, resulting in degradation of glucose and production of lactate that accumulates in the muscles. The accumulation of lactate in the muscles has been associated to muscle fatigue and a decrease in athletic performance. Moreover, recent studies have demonstrated that lactate accumulated in muscles under insufficient oxygen supply (e.g., ischemic muscles) may contribute to pain by acting on sensory neurons innervating muscles.

Massage therapy, which involves the manipulation of soft tissue either manually or with the aid of mechanical devices, can increase movement of lymphatic fluid or blood throughout the muscles, accelerating the transport of accumulated lactate to a gluconeogenic organ such as the liver. Consequently, massage therapy has been used to reduce the effects of muscle fatigue and to relieve pain after physical activity.

Common approaches that leverage the therapeutic effects of massages to treat muscles before, during, and after physical activity include the use of foam rollers (e.g., self-myofascial release, SMR), percussive massagers, and trained massage therapists or chiropractors. The use of foam rollers is an emerging intervention approach that applies the principle of biomechanical loading of soft tissue and stimulation of mechanoreceptors in the muscles, tendons and fascia, which results in autogenic inhibition and allows the muscles to relax. Foam rollers are cylindrical or spherical devices that can include textured surfaces designed to target specific muscles, and that can be fabricated in different sizes and densities using various materials such as expanded polypropylene (EPP) or ethylene-vinyl acetate (EVA). Foam rollers are used by applying gentle and sustained pressure to a tender area in the fascia, while maintaining the position and load until the tissue responds by relaxing and allowing the fascia to release. Research studies have shown the use of foam rollers can significantly improve the range of motion (ROM) and prevent injury in the lumbar spine, hip, knee, and ankle joints. However, the use of foam rollers requires knowledge of the muscle or groups of muscles that need to be massaged, as well as the correct techniques to execute the massages in order to achieve the desired effect. Improper use of foam rollers can sometimes exacerbate the effects of muscle fatigue and in some cases cause injury.

Percussive massagers are hand-held devices that include an electric motor coupled to a reciprocating piston within a cylinder, and a variety of percussive heads that can be attached to the piston to provide rhythmic, rapid tapping, cupping or hacking on selected areas of the body. The use of percussive massagers is aimed at stimulating the cutaneous tissue, superficial muscle, and nerve endings to increase blood flow within the muscle, accelerating delivery of oxygen and improving drainage of the lymphatic system. Percussive massagers have been used to treat muscles during warm-up sessions as well as during muscle recovery after intense physical activity. Despite these advantages, percussive massagers have several limitations, including inability to change the shape, amplitude, and/or driving mode, which restricts the types of massages that can be performed, high cost, relatively large size and weight, and high levels of noise due to the mechanisms used to convert the rotational energy of the electric motor to the reciprocating motion of the piston. Additionally, the use of percussive massagers often requires well trained operators (i.e., masseuses) that know the correct areas to target for massaging, and the intensity of the massage required to achieve the desired response. Use of percussive massagers by individuals that are not well trained and/or that may have previously sustained injuries such as strains, sprains or even extreme swelling can potentially exacerbate the injury, causing further damage.

Massage therapists and/or chiropractors are trained individuals that can evaluate the needs of an individual and/or athlete based on several factors including the type, frequency, and intensity of physical activity, physiological characteristics, and/or preferences, providing customized treatments specifically designed to target the muscles or group of muscles requiring attention. Experienced massage therapists can (i) massage a muscle or group of muscles, (ii) sense with their hands properties related to condition of a muscle or group of muscles, for example stiffness, mobility, flexibility, and/or neural tone, and (ii) make adjustments to the intensity and type of massage being executed in order to achieve best results. Furthermore, studies have shown massage therapists routinely provide treatments that incorporate multimodal massages such as soft tissue therapy, mobilization, kinesiotherapy, low force techniques, and instrument assisted soft tissue therapy, prescribe rehabilitative exercises, and give ergonomic and nutritional advice. Massage therapists and/or chiropractors can offer comprehensive strategies to relieve pain and provide physical recovery resulting in long-term benefits. The disadvantages of using trained massage therapists and/or chiropractors are mostly related to their limited availability and high cost of their services, which frequently makes them accessible only to high performance athletes and sports professionals.

Systems, devices, and methods described herein address the limitations of existing systems by providing systems, devices, and methods for treatment of muscle fatigue and/or pain that allows for dynamic control of forces applied to specific areas of the body based on feedback received from one or more sensors and/or a user. Such systems, devices, and methods can treat the effects of muscle fatigue and provide pain relief by tailoring massage therapy to individual users, thereby incorporating certain advantages and benefits of having a trained massage therapist and/or chiropractor. Such treatment can be accessible to users in a wide range of settings and offers a low-cost alternative to using a trained massage therapist and/or chiropractor. Moreover, devices described herein can provide instruction and/or feedback to a user to assist users in providing more effective therapy than existing form rollers, percussive massage devices, and other devices.

In some embodiments, the massage devices described herein can include one or more sensors that can accurately measure information related to output forces produced by a massage device and imparted on a muscle or group of muscles of a user. The information measured by the one or more sensors can be processed and analyzed by a control unit (e.g., a processor) to adjust the profiles or waveforms of output forces produced by the massage device and/or provide a user with feedback on how to apply the message therapy to achieve more effective results.

FIG. 1 is a schematic illustration of an example muscle measurement and treatment device 100 according to an embodiment. The muscle measurement and treatment device 100 (also referred to herein as "muscle management device") can include a housing 110, a power source 120, a driving mechanism 130, an output mechanism 140, a control unit 150, and a signal generator 160. Optionally, the muscle management device 100 can include one or more sensor(s) 132 that can be operatively coupled to one or more other components of the muscle management device 100. In some embodiments, the muscle management device 100 can be configured to provide treatment of muscle fatigue and/or pain of a user that allows for dynamic control of forces applied to specific areas of the body based on feedback received from the sensor(s) 132. In some embodiments the muscle management device 100 can also be configured to measure and/or determine the state or condition of a tissue or muscle by transferring mechanical energy to a target area (e.g., skin and/or muscle) and measuring, via the sensor(s) 132, forces exerted on the muscle management device 100 in response to the transferred mechanical energy.

The housing 110 can define one or more areas (e.g., chambers) for accommodating (e.g., housing, containing, supporting, etc.) one or more components of the muscle management device 100, while providing one or more interfaces that enable such components to be coupled to external components and/or other devices. As depicted in FIG. 1, the housing 110 can accommodate the power source 120, the driving mechanism 130, the control unit 150, and the signal generator 160 of the muscle management device 100. The housing 110 can be formed of any suitable material, including, for example, a metal, glass, ceramic, and/or polymer. In some embodiments, the housing 110 can include multiple portions that can be coupled together to form one or more chambers for receiving the components of the muscle management device 100. In some embodiments, the housing 110 can be formed of multiple layers of material, e.g., an inner layer having more rigidity and an outer layer having more flexibility to facilitate gripping and/or other manipulation of the muscle management device 100. In some embodiments, the housing can include or house one or more materials that exhibit properties such as, for example, audible noise dampening agents, heat dissipation materials, etc.

The housing 110 can have any suitable shape or configuration for housing and/or supporting the one or more components of the muscle management device 100 and/or facilitating manipulation by a user. In some embodiments, the housing 110 can be an elongate member that has any suitable cross-sectional shape, including, for example, a circle, a square, rectangular, and/or other polygonal cross-sectional shape. In some embodiments, the housing 110 can be a cube or the like having rounded or non-rounded edges, corners, etc. In some embodiments, the housing 110 can have a shape, surface features, and/or surface material or finishes that can be configured to increase the ergonomics of the muscle management device 100, which can, for example, allow a user to manipulate the muscle management device 100 with one hand (i.e., single-handed use). In some embodiments, the housing 110 can be shaped and/or configured to achieve a desired positioning of the output mechanism 140 against a target area of the body of a user.

In some embodiments, the housing 110 can include one or more openings that enable coupling between interior and exterior components of the muscle management device 100 as well as coupling between one or more components of the muscle management device 100 and other devices. For example, the housing 110 can include openings that enable coupling between the output mechanism 140 and the driving mechanism 130, control unit 150, and/or sensor(s) 132, as further described below. In some embodiments, the housing 110 can include one or more ports for coupling the muscle management device 100 to one or more compute devices (e.g., for sending and/or receiving data) and/or external power sources.

The muscle management device 100 can include an onboard power source 120, e.g., to power one or more components of the massage device 100. The power source 120 can be any suitable energy source and/or energy storage device. In some embodiments, the power source 120 can include one or more rechargeable batteries. In some embodiments, the muscle management device 100 can include one or more ports that enable connection between an external power source and one or more components of the muscle management device 100. The external power source can be used to directly power the components of the muscle management device 100 and/or recharge the onboard power source 120.

The control unit 150 can be configured to activate and/or control the operation of one or more components of the muscle management device 100, e.g., by receiving electrical signal(s) from and/or sending electrical signal(s) to other components of the muscle management device 100. The control unit 150 can include a memory 152, a processor 154, and an input/output (I/O) device 156.

The memory 152 can be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, memory 152 stores instructions that cause processor 154 to execute modules, processes, and/or functions associated with operating one or more components of the muscle management device 100. Such instructions can be designed to integrate specialized functions into the control unit 150, such that the muscle management device 100 can perform methods, as further described below.

The processor 154 of control unit 150 can be any suitable processing device configured to run and/or execute functions associated the muscle management device 100. For example, processor 154 can be configured to process and/or analyze sensor data (e.g., received from sensor(s) 132), to cause the signal generator 160 to generate signals (e.g., waveforms) for activating movement of the output mechanism 140, to adjust one or more parameters of the signals (e.g., waveform shape, frequency, amplitude, etc.), and to generate feedback and/or instructions to provide to a user to facilitate application of the muscle management device 100 to treat one or more muscle conditions. Such functions and others are further described with reference to later figures herein. The processor 154 can be a general-purpose processor, a Field Programmable Gate Array (FPGA), an Application Specific Integrated Circuit (ASIC), a Digital Signal Processor (DSP), and/or the like.

The input/output (I/O) device 156 include one or more components for receiving information and/or sending information to other components of muscle management device 100 and/or other devices. In some embodiments, the I/O device 156 can optionally include or be operatively coupled to a display, audio device, or other output device for presenting information to a user. In some embodiments, the I/O device 156 can include a communication interface that can enable communication between control unit 150 and one or more of sensor(s) 132, power source 120, signal generator 160, driving mechanism 150, output mechanism 140, etc. In some embodiments, the I/O device 156 can include a network interface that can enable communication between control unit 150 and one or more external devices, including, for example, an external user device (e.g., a mobile phone, a tablet, a laptop) and/or other compute device (e.g., a local or remote compute, a server, etc.). The network interface can be configured to provide a wired connection with the external device, e.g., via a port or firewall interface, can be configured to communicate with the external device via a wireless network (e.g., Wi-Fi, Bluetooth®, low powered Bluetooth®, Zigbee and the like). In some embodiments, the communication interface can also be used to recharge a power source (e.g., power source 120), such as a rechargeable battery.

In some embodiments, the control unit 150 can be or form part of an integrated circuit. For example, the control unit 150 can be an integrated chip that integrates components including a memory (e.g., memory 152), a central processing unit (e.g., processor 154), and one or more ports and/or interfaces for communication (e.g., I/O device 156). The integrated circuit can also include one or more other components of the system, including, for example, signal generator 160.

The control unit 150 can generate electrical signals to control one or more components of the muscle management device 100, e.g., based on instructions stored in the memory 152. These electrical signals may be communicated between the control unit 150 and other components of the muscle management device 100 via a communication interface of I/O device 156. In some embodiments, the control unit 150 can control the signal generator 160 to generate one or more signals to drive the driving mechanism 130. For example, the control unit 150 can control the signal generator 160 to generate one or more current patterns or waveforms, which can be used to drive one or more components of the driving mechanism 130, as further explained in detail with reference to later figures. In some embodiments, the control unit 150 can control the signal generator 160 to adjust one or more parameters of a signal (e.g., waveform shape, frequency, amplitude) based on signals or data received from one or more sensors (e.g., sensor(s) 132). For example, one or more sensor(s) 132 can be configured to measure voltage, current, impedance, movement, acceleration, or other data associated with the muscle management device 100, and the control unit 150 can control the operation of the signal generator 160 and/or driving mechanism 130 (e.g., by sending electrical signals to the signal generator 160 and/or driving mechanism 130) based on data received from the sensors.

The signal generator 160 can be operatively coupled to the control unit 150 and the power source 120, and can generate one or more signals that energize the driving mechanism 130. In some embodiments, the signal generator 160 can form part of or be integrated into the control unit 150. The signal generator 160 and/or circuitry coupled to the signal generator 160 can be configured to generate one or more current waveforms that can be used to drive movement of a transducer, motor, or other components of the driving mechanism 130. The waveforms can have one or more parameters that can be adjusted, e.g., based on data received from the one or more sensor(s) 132). For example, the waveforms can have a predefined shape (e.g., a sine wave, a sawtooth wave, a square wave, etc.), a predefined frequency, a predefined amplitude, or other parameters that can be adjusted, e.g., by control unit 150. In some embodiments, the signal generator 160 and/or circuitry can generate a current waveform that can be passed through a coil (e.g., electromagnetic coil) to generate a magnetic field, whereby changes in the magnetic field can drive movement of one or more components of the muscle management device 100. Further details regarding this application are described with reference to FIG. 3 below.

The driving mechanism 130 of the muscle management device 100 can be configured to drive movement of the output mechanism 140 such that the output mechanism 140 produces a mechanical output. The driving mechanism 130 can be, for example, an electric motor, a transducer, or other suitable component for generating mechanical movement. The driving mechanism 130 can be operatively coupled to the signal generator 160, the output mechanism 140, and/or one or more other components of the muscle management device 100. In some embodiments, the driving mechanism 130 can be configured to receive an electrical signal (e.g., an electric current) from the signal generator 160 and to generate mechanical movement along an axis X (or primary axis) of the muscle management device 100 (e.g., a longitudinal axis of the muscle management device 100). The mechanical movement can cause the output mechanism 140 to produce an output signal (e.g., by moving back-and-forth or in an oscillatory or vibratory manner) that can be applied to a user to treat one or more muscle conditions (e.g., fatigue, tension, pain, etc.). The output signal can have certain properties (e.g., frequency, amplitude, force, pattern, etc.), which can be adjusted (e.g., by changing the electric signal used to drive the driving mechanism 130) to be therapeutically effective at treating specific muscle conditions.

Various factors that can affect and/or determine the properties of the output signals of the output mechanism 140 include, for example, the characteristics of electric motor of the driving mechanism 130 (e.g., brushless motor, brushed motor, direct drive motor, linear motor, servo motor etc.), the ease of movement of the output mechanism (e.g., how frictionless is the movement of the output mechanism), the paths of energy dissipation (e.g., off-axis movement, heat, friction, etc.), and/or the direction of movement with respect to external forces (e.g., pressure and/or forces encountered by the output mechanism 140 during use, gravitational forces, etc.). The driving mechanism 130 can be configured to reduce or minimize factors (e.g., including friction, off-axis movement, etc.) that can affect the efficiency of the mechanical movement of the output mechanism 140. For example, the driving mechanism 130 can include guide members or walls that reduce movement of components that are off axis to axis X.

In some embodiments, the driving mechanism 130 can be or include a Lorentz force motor (e.g., a linear Lorentz force or voice-coil motor). A Lorentz force motor can be lightweight and have a compact size that is particularly suitable for applications described herein. The Lorentz force motor can use a magnet and a coil (e.g., conductor) to convert electrical energy to mechanical energy according to the Lorentz force principle, e.g., that a current-carrying conductor located within a magnetic field can generate a force (Lorentz or electromagnetic force). The magnitude of the Lorentz force is proportional to the electrical current passing through the conductor and the magnetic flux produced by the magnet, producing linear force or torque output, and high acceleration or frequency actuation. Further details regarding embodiments using a Lorentz force motor are described below with reference to FIGS. 3 and 4. In some embodiments, the driving mechanism 130 can be or include an alternating current (AC) brushless motor with permanent electromagnets that uses induction of a rotating magnetic field generated in a stator component to turn the stator and a rotor at a synchronous rate. The AC brushless motor can produce high torque to weight ratio, high torque per watt of power input, and low susceptibility to mechanical wear. In some embodiments, the driving mechanism 130 can be or include a direct current (DC) brushed motor with permanent magnets on the outside (e.g., stationary components or stator components), and a spinning armature (rotor) located on the inside. The spinning armature, which contains the brushes, an electromagnet, and a coil wound around the electromagnet, rotates 180 degrees when an electric current is run through the coil until the brushes make contact with the stator components, reversing the magnetic field and allowing the rotor to spin 360 degrees. DC brushed motors exhibit linear performance characteristics and high torque and wide speed range, producing smooth motion at low speeds and allowing for precise speed control. In some embodiments, the driving mechanism 130 can be or include a piezoelectric transducer driven by an electrical signal to generate vibrations, e.g., in the ultrasonic frequency range. The vibrations of the piezoelectric transducer at high frequencies can produce acoustic radiation pressure. The driving electrical signal can also be clocked on and off at a low frequency, such that the pressure from the piezoelectric transducer applied on and off at the lower frequency generates a corresponding vibratory signal at low frequency. The use of a piezoelectric transducer can reduce a size and weight of the muscle management device 100, as piezoelectric transducers can be smaller and lighter than other types of electro-mechanical transducers. Other suitable transducers, electromagnetic devices, motors, etc. can be used with or as alternatives to the embodiments described herein.

In some embodiments, the driving mechanism 130 can move the output mechanism 140 at a first frequency along a first axis (e.g., axis X) and also move output mechanism 140 at a second frequency along second axis (e.g., an axis off axis from axis X, such as an axis perpendicular to axis X). In some embodiments, the driving mechanism 130 can be configured to move the output mechanism 140 along a single axis and to reduce movement (e.g., vibrations) along one or more secondary axes, e.g., using one or more mechanical components (e.g., guides).

In some embodiments, the muscle management device 100 can optionally include one or more sensor(s) 132. The sensor(s) 132 can be configured to measure and/or record information associated with the muscle management device 100. For example, the sensor(s) 132 can measure voltage, current, impedance, electric and/or magnetic field (e.g., a directional magnetic field generated by the electrical signal and applied near the driving mechanism 130), movement (e.g., a position and/or movement of a component of the driving mechanism 130 and/or output mechanism 140), acceleration (e.g., an acceleration of a component of the driving mechanism 130 and/or output mechanism 140), force (e.g., a strain on a component of the driving mechanism 130 and/or output mechanism 140), or other data associated with one or more components of the muscle management device 100.

In some embodiments, a sensor 132 can be integrated with and/or form part of other components of the muscle management device 100 such as, for example, the driving mechanism 130, the output mechanism 140, and/or the control unit 150. Alternatively, in other embodiments, a sensor 132 can be separate from but be operatively coupled to the driving mechanism 130, the output mechanism 140, and/or the control unit 150.

In some embodiments, the sensor(s) 132 can be used to monitor the performance of the muscle management device 100, e.g., to detect inefficiencies in performance, errors, etc. In some embodiments, the sensor(s) 132 can be used to monitor feedback from operating the device, e.g., feedback from applying the device to skin and/or muscle tissue. In some embodiments, the sensor(s) 132 can be used to monitor one or more environmental conditions and/or physiological conditions of a user. The control unit 150, in response to receiving data from the sensor(s) 132, can be configured to adjust the operation of the muscle management device 100 (e.g., adjust a parameter of the signal waveform used to drive the driving mechanism 130, power off or on the massage device 100, etc.) based on the sensor data.

In some embodiments, the sensor 132 can include an ammeter for monitoring a current associated with the driving mechanism 130 and/or another portion of the muscle management device 100. Based on the measured current, the control unit 150 can control the signal generator 160 to adjust one or more parameters (e.g., frequency, amplitude, shape) of an electrical signal being produced by the signal generator 160 and used to energize the driving mechanism 130.

In some embodiments, the sensor 132 can include a strain gauge (or a load cell including strain gauges) to detect the magnitude and direction of strain experienced by one of more components of the muscle management device 100. The strain gauge can be fabricated from thin wire or foil organized in a grid pattern and attached to a flexible backing such that when the shape of the strain gauge is altered, a change of its electrical resistance occurs. The geometry of the wire or foil in the strain gauge is such that when force is applied one direction, a linear change on resistance takes place. For example, tension force can stretch a strain gauge, causing it to become thinner (e.g., elongated) and increasing the electrical resistance. In contrast, compression force can deform the wire or foil making it thinker and reducing the electrical resistance. The changes of electrical resistance of an individual strain can be small. As such, a plurality of strain gauges (e.g., mounted on a load cell) can be used together to detect changes in electrical resistance. For example, a strain gauge load cell can include four strain gauges accommodated in a Wheatstone bridge. In some embodiments, the strain gauge can be coupled to a member supporting the output mechanism 140 and/or a portion of the driving mechanism 140 such that forces exerted on the output mechanism 140 and/or delivery interface 144 of the output mechanism 140 can be measured and/or detected by measurements made by the strain gauges. An example of such an embodiment is described below with reference to FIGS. 5 and 6. In some embodiments, the sensor 132 can be configured to measure a position, velocity, and/or acceleration of the output mechanism 140.

Such force or strain measurements or position, velocity and/or acceleration measurements can be indicative of or used to determine a state or condition of tissue or muscle with which the output mechanism 140 is in contact. For example, muscle that is more knotted and/or tense may exert greater forces upon the output mechanism 140 and monitoring such changes in force can enable adjustments to be made to the force imparted by the output mechanism 140 on the tissue or muscle. A muscle that is more knotted and/or tense may also resist deformation, and therefore measurements associated with a position or movement of the output mechanism 140 (such as position, velocity, and/or acceleration measurements) can vary depending on the state or condition of the muscle. As such, force or strain measurements or position, velocity and/or acceleration measurements can be used to determine one or more properties of the muscle or tissue being contacted by the output mechanism 140 (or a delivery interface or end effector of the output mechanism 140). For example, such measurements can be used to determine one or more biomechanical properties (e.g., stiffness or elasticity and/or compliance) of the muscle.

In some embodiments, measurements of the forces exerted by or on the output mechanism 140 can be used to provide feedback to a user, e.g., via control unit 150. For example, the control unit 150 can detect that force below a predefined value or force above a predefined value is being exerted on tissue and/or muscle (e.g., forces outside of a predefined range is being exerted on tissue and/or muscle) and provide that feedback to a user. The feedback can inform the user of improper and/or ineffective usage of the muscle management device 100, and allow the user to change a direction, orientation, and/or force applied by the muscle management device 100 on tissue and/or muscle. In some embodiments, having multiple strain gauges orientated in different directions or along different support members can facilitate discrimination between lateral and/or axial forces and enable further adjustments by a user and/or control unit 150 to be made. In some embodiments, the control unit 150 can be configured to generate and/or provide instructions to a user based on the feedback from the sensor(s) 132.

In some embodiments, a sensor 132 can include a position sensor to detect the position of components of the driving mechanism 130 and/or output mechanism 140. The position sensor may indicate absolute position (location) or relative position (displacement), in terms of linear travel, rotational angle, or three-dimensional space. In some embodiments, the position sensor can be a capacitive displacement sensor that measure variations of capacitance between two points (e.g., the sensor and a conductive target). In some embodiments, the position sensor can be an inductive sensor that uses a coil and an oscillator to create a magnetic field in the close surroundings of the sensing surface and produce a dampening of the oscillation amplitude in response to the position of an actuator. In some embodiments, the position sensor can be an optical component such as a laser doppler vibrometer that directs a laser beam at surface of interest, and the vibration amplitude and frequency are extracted by the doppler shift of the of a reflected laser beam frequency due to the motion of the surface. In some embodiments, the position sensor can be a linear variable differential transformer (LVDT), a piezoelectric transducer, a potentiometer, an ultrasonic sensor or the like.

In some instances, one or more components of the driving mechanism 130 can be affected by external fields and other factors that can impact the performance of the driving mechanism 130. For example, in the case of a Lorentz motor, nearby magnetic obtain may have an impact on the performance of the motor. In some embodiments, the muscle management device 100 can include a sensor 132 implemented as a Hall effect sensor that monitors magnetic field fluctuations and sends electrical signals associated to those measured fluctuations to the control unit 150. In response to those measured fluctuations, the control unit 150 can modify the electrical signal being generated by the signal generator 160, e.g., to adjust the frequency, amplitude, etc. of the electrical signal to achieve desirable ranges of operation.

The output mechanism 140 of the muscle management device 100 can be configured to transfer the mechanical energy generated by the muscle management device 100 to a target area (e.g., skin and/or muscle area) of a user. The output mechanism 140 can be operatively coupled to the driving mechanism 130 and be configured to move in response to movement generated by the driving mechanism 130. In some embodiments, the output mechanism 140 can be disposed outside of the housing 110, while in other embodiments, a portion of the output mechanism 140 can be disposed within the housing 110 with a portion of the output mechanism 140 extending from the housing 110. In some embodiments, the output mechanism 140 can move in and out of the housing 110, in response to the mechanical movement of the driving mechanism 130. In some embodiments, the output mechanism 140 can include a shaft. In some embodiments, the shaft can extend from an opening in the housing 110. In some embodiments, the muscle management device 100 can optionally include a linear bearing within which the shaft is disposed, such that the linear bearing can guide the movement of the shaft. Further details of such an embodiment are described with reference to FIGS. 3 and 4. In some embodiments the output mechanism 140 can include a crank arm, a connecting rod (con rod), a long stroke piston, and a shaft. The crank arm can include a first end coupled to a rotary motor of the driving mechanism 130 and a second end coupled to the con rod and to convert the rotational movement generated by the rotary to a linear movement. In operation, the rotary motor causes the con rod to reciprocate axially and move the long stroke piston, which is coupled the shaft.

The output mechanism 140 can include a delivery interface 144 that is configured to contact the skin and/or muscle of a user. In some embodiments, the delivery interface 140 can be configured with considerations of ease of use and/or comfort for the user, for example, during use of the muscle management device 100 to treat a muscle condition. The delivery interface 140 may be configured to reduce secondary effects that may be undesirable such as the generation and accumulation of heat, generation of audible noise, lack of air circulation, application of pressure against a target area, etc. In some embodiments, the delivery interface 144 can be implemented as one or more interchangeable tips, which can each be used to apply a force generated by the message device on a muscle or group of muscles of a user. The interchangeable tips can be any suitable size, shape, or configuration for applying therapeutically effective forces for treating a muscle condition. For example, the interchangeable tips can be configured to concentrate force over a predefined area and/or in a predefined way such that the tips can be used to target specific tissue and/or muscles. In some embodiments, the interchangeable tips can be spherical, conical, disc, cylinder, toroid, cuboid, polyhedral or any other geometrical shape. In some embodiments, the interchangeable tips can be an irregular shape. The interchangeable tips can be fabricated from flexible, elastic and/or compliant materials including ethylene vinyl acetate (EVA), polyethylene, polyurethane, rubber, etc. In some embodiments, the surface of the interchangeable tips can be textured surfaces designed to increase friction against skin and/or target specific tissue and/or muscles. While a single output mechanism 140 with a single delivery interface is depicted, it can be appreciated that multiple output mechanisms and/or delivery interfaces can be used.

As described above, the muscle management device 100 can be configured to provide treatment of muscle fatigue and/or pain, and to measure and/or determine the state or condition of muscle. In some embodiments, the treatment of muscle fatigue and/or pain and the measurement of the state or condition of muscle can be performed by separate devices. That is, in some embodiments the treatment of muscle fatigue and/or pain can be performed using a first device which can be referred to as a "muscle treatment device" or "massager device", and the measurement of the state or condition of muscle can be performed using a second device, separate from the first device (but can optionally be communicatively coupled to the first device), which can be referred to as a "measurement device" or "scanner." In some instances, the massager device and the measurement device can be part of a muscle management system configured to determine the state or condition of muscle of a user and/or to provide treatment of muscle fatigue and/or pain to the user, as further described herein.

Figure 9:
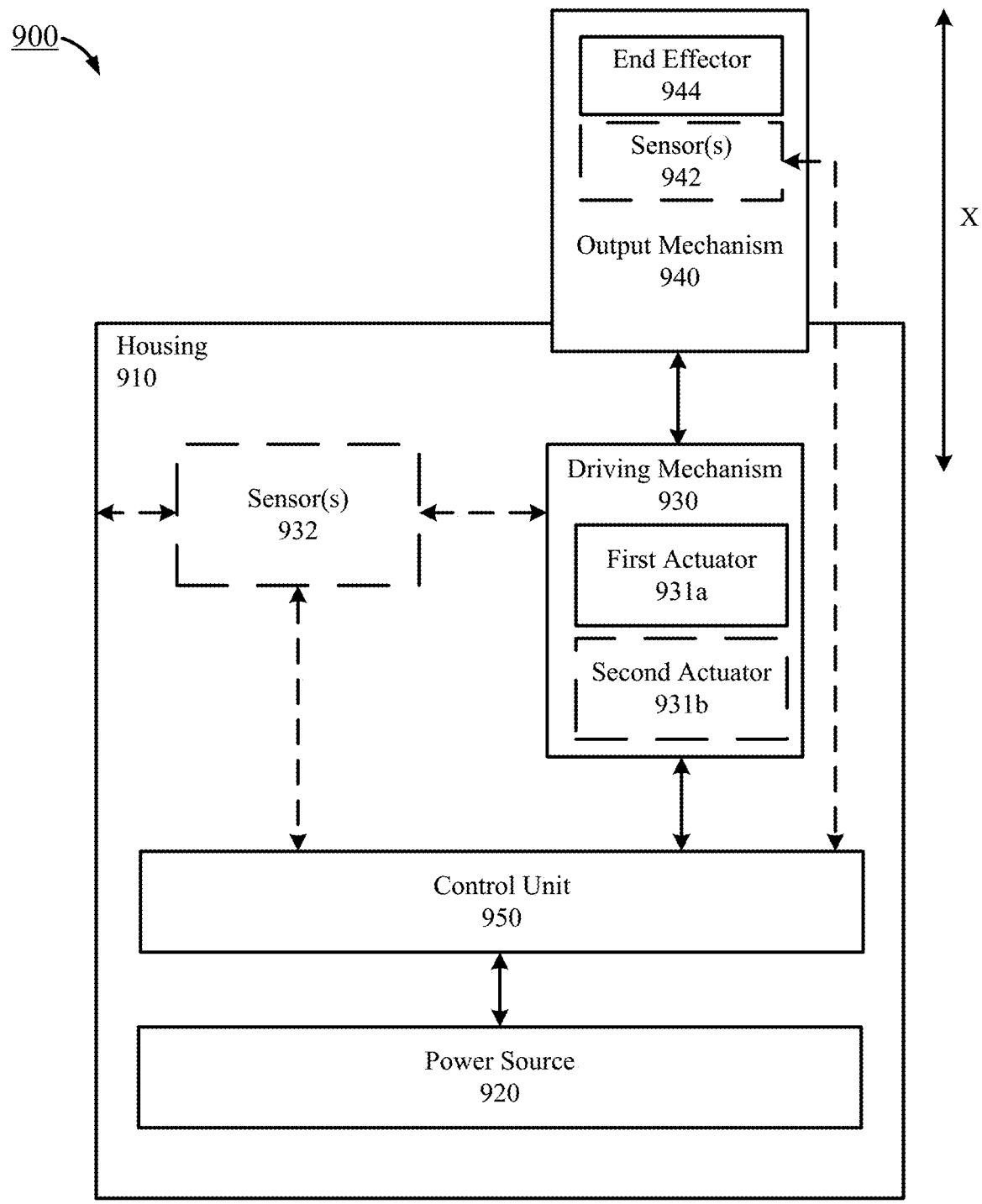
FIG. 9 is a schematic illustration of a massager device, according to an embodiment.

FIG. 9 shows a schematic illustration of a massager device 900, also referred to as massage device or muscle treatment device, according to an embodiment. The massager device 900 can be configured to provide treatment of muscle fatigue and/or pain of a user. The massager device 900 can include components that are structurally and/or functionally similar to components of the muscle management device 100. For example, the massager device 900 can include a housing 910, a power source 920, a driving mechanism 930, an output mechanism 940, and a control unit 950. Optionally, the massager device 900 can include one or more sensor(s) 932 and/or sensor(s) 942 that can be operatively coupled to the housing 910, the driving mechanism 930, and/or the control unit 950. Thus, portions and/or components of the massager device 900 that have been described above with respect to FIG.1 are not described in detail again herein.

The housing 910 can define one or more areas (e.g., chambers) for accommodating (e.g., housing, containing, supporting, etc.) one or more components of the massager device 900. For example, in some embodiments the housing 910 can include a first chamber and a second chamber. The first chamber can be configured to house, contain, and/or accommodate the driving mechanism 930, the output mechanism 940, the control unit 950, and optionally one or more sensor(s) 932. The second chamber can be configured to house, contain, and/or accommodate the power source 920. The first chamber can be configured to be removably couplable to the second chamber to facilitate removing a depleted power source 920 (e.g., a discharged power source 920 or a power source 920 that has consumed its stored energy to power the massager device 900) and replacing the depleted power source 920 with a fully charged power source 920. The first chamber can be removably couplable to the second chamber by any suitable coupling mechanism.

For example, in some embodiments the first chamber can include an engineering fit, interreference fit, press fit and/or friction fit configured to receive and immobilize the second chamber of the massager device 900. In some embodiments the first chamber can include an opening, cavity, slot or the like defining an interference fit that can secure a portion of the second chamber by friction, after a surface defining an opening of the first chamber and the second chamber are pushed together. In other embodiments, the first chamber can include a threaded end or threaded portion that can be coupled to a similarly sized threaded end or threaded portion disposed on the second chamber such that the power source 920 is secured and/or attached to the massager device 900. Alternatively, in some embodiments, the housing 910 can include a single chamber or main chamber that houses the driving mechanism 930, the output mechanism 940, the control unit 950, the power source 920, one or more sensor(s) 932, and/or other components of the massager device 900. The housing 910 can include one or more windows or doors that can open to provide access to one or more internal components of the massager device 900, such as, for example, the power source 920, for replacement and/or maintenance.

The housing 910 can be formed of any suitable material, including, for example, a metal, glass, ceramic, and/or polymer. In some embodiments the first and the second chamber of the housing 910 can be formed of multiple layers of material, e.g., an inner layer having more rigidity and an outer layer having more flexibility (e.g., made of a textured material to facilitate gripping and/or other manipulation of the massager device 900). In some embodiments, the housing 910 can include a first chamber and a second chamber that have a shape, surface features, and/or surface material or finishes that can be configured to increase the ergonomics of the massager device 900, which can, for example, allow a user to manipulate the massager device 900 with one hand (i.e., single-handed use). In some embodiments, the housing 910 can be shaped and/or configured to achieve a desired positioning of the output mechanism 940 against a target area of the body of a user.

The power source 920 can be any suitable energy source and/or energy storage device. In some embodiments, the power source 920 can include one or more rechargeable batteries. In some embodiments, the massager device 900 can include one or more ports disposed on the second chamber of the housing 910 that enable connection between an external power source and one or more components of the massager device 900. The external power source can be used to directly power the components of the massager device 900 and/or recharge the onboard power source 920.

The control unit 950 can be configured to activate and/or control the operation of one or more components of the massager device 900, e.g., by receiving electrical signal(s) from and/or sending electrical signal(s) to other components of the massager device 900. The control unit 950 can be coupled to the power source 920 and the driving mechanism 930. Optionally, in some embodiments the control unit 950 can be coupled to one or more sensor(s) 932 and/or sensor(s) 942, as further described herein. While not depicted herein, the control until 950 can include components such as a memory, a processor, and/or an I/O device, which can be structurally and/or functionally similar to the memory 152, processor 154, and I/O device 156, respectively, as described above with reference to FIG. 1.

In some embodiments, the control unit 950 can control delivery of power from the power source 920 to the driving mechanism 930. In some embodiments, the control unit 930 can generate (e.g., via a signal generator (not depicted)) one or more signals to drive the driving mechanism 930. For example, the control unit 950 can generate one or more current patterns or waveforms, which can be used to drive one or more components of the driving mechanism 930. Moreover, in some embodiments the control unit 950 can also adjust one or more parameters of a signal (e.g., waveform shape, frequency, amplitude) based on signals or data received from the one or more sensor(s) 932 and/or the sensor(s) 942. For example, one or more sensor(s) 932 can be coupled to the housing 910 and configured to measure movement and/or position of the output mechanism 940 with respect to the housing 910. In particular, a sensor 932 coupled to the housing 910 can detect when the housing 910 is moving, which can indicate that the massager device 900 is not providing the desired muscle treatment and/or therapy. For example, a user may have pressed the output mechanism 940 of the massager device 900 too much against a region of tissue or the massager device 900 is pushing against bone or other hard structure, which causes the housing 910 of the massager device 900 to move together with the output mechanism 940. As such, a sensor 932 that detects the movement or acceleration of the housing 910 can inform the control unit 950 (or another device that is operatively coupled to the massage device 900, such as, for example, user device 1180, compute device(s) 1190, third-party device(s) 1185, and/or other devices, as described below with reference to FIG. 11) that the massage device 900 is not delivering the necessary massage treatment and/or needs to be adjusted (e.g., to move off of bone and/or press less firmly against the muscle). In some embodiments, the data captured by the sensor(s) 932 can be received by the control unit 950 and can be used to adjust one or more parameters of the operation of the driving mechanism 930 (e.g., by sending electrical signals to the driving mechanism 930).

Alternatively and/or additionally, in some embodiments one or more sensor(s) 942 can be included in the output mechanism 940 and can be configured to measure, for example, the movement, acceleration, and/or position of the output mechanism 940. The data captured by the sensor(s) 942 can be received by the control unit 950 and can be compared and/or combined with the data received from the sensor(s) 932, e.g., to provide information to one or more devices and/or processors regarding the muscle treatment being applied, to facilitate instructions to the user to adjust the positioning and/or use of the massager device 900, and/or to adjust one or more parameters of the operation of the driving mechanism 930.

The output mechanism 940 of the massager device 900 can be configured to transfer mechanical energy generated by the massager device 900 to a target area (e.g., skin and/or muscle area) of a user. The housing 910 can include an opening through which the output mechanism 940 can extend. The output mechanism 940 can include a proximal end that is coupled to the driving mechanism 930. The output mechanism 940 can be configured to move in response to movement generated by the driving mechanism 930. In some embodiments, the output mechanism 940 can be disposed outside of the housing 910, while in other embodiments, a portion of the output mechanism 940 can be disposed within the housing 910 with a portion of the output mechanism 940 extending from the housing 910. The output mechanism 940 can include a delivery interface or end effector 944 that is configured to contact the skin and/or muscle of a user. In some embodiments, the end effector 944 can have a shape that is suitable for contacting and applying pressure (e.g., applying muscle treatment and/or therapy) to a user. In some embodiments, the end effector 944 can have a rounded, atraumatic shape (e.g., a rounded dome-like shape), while in other embodiments, the end effector 944 can include multiple protrusions, convexities, concavities, textures, etc.

The driving mechanism 930 of the massager device 900 can be configured to drive movement of the output mechanism 940 such that the output mechanism 940 produces a mechanical output. The driving mechanism 930 can include, for example, an electric motor (e.g., Lorentz force motor, AC motor, DC motor, etc.) or other suitable actuator for generating mechanical movement, as further described below. The driving mechanism 930 can be operatively coupled to the control unit 950 and the output mechanism 940. Optionally, the driving mechanism 930 can be coupled to the one or more sensor(s) 932, as further described herein. The driving mechanism 930 can be configured to receive an electrical signal (e.g., an electric current) from the control unit 950 and to generate mechanical movement of the output mechanism 940 along an axis X. The axis X can correspond to a longitudinal axis of the massager device 900, as shown in FIG. 9. The mechanical movement can cause the output mechanism 940 to produce an output signal (e.g., by moving back-and-forth or in an oscillatory or vibratory manner) that can be applied to a user to treat one or more muscle conditions (e.g., fatigue, tension, pain, etc.). The output signal can have certain properties (e.g., frequency, amplitude, force, pattern, etc.), which can be adjusted (e.g., by changing the electric signal used to drive the driving mechanism 930) to be therapeutically effective at treating specific muscle conditions.

As noted above, the driving mechanism 930 can include one or more actuators, such as a first actuator 931a and, optionally, a second actuator 931b. In some embodiments, the first actuator 931a and the second actuator 931b can be separately coupled to the output mechanism 940, and each can be used independently to drive the movement of the output mechanism 940. In some embodiments, the first actuator 931a can be coupled to the second actuator 931b to generate more complex output signals, as further disclosed herein. The first actuator 931a and the second actuator 931b can each be an electric motor including, for example, a Lorentz force motor, a brushless DC motor, a brushed DC motor, a piezoelectric actuator, a locked-rotor amperage (LRA) motor, a solenoid or the like. The first actuator 931a and the second actuator 931b can be coupled to motor drives that can impart mechanical movement to the output mechanism 940. In some embodiments, the first actuator 931a and the second actuator 93 lb can be the same type of actuator. Alternatively, in other embodiments the first actuator 931a and the second actuator 931b can be different types of actuators. For example, in some embodiments the first actuator 931a can be an electric motor that can generate low frequency but high force and/or displacement movements along the X axis, and the second actuator 931b can be an electric motor that can generate low force and/or displacement but high frequency or bandwidth movements along the X axis. In some embodiments, the first actuator 931a can include an electric motor coupled to a crank-piston that can convert rotary motion into linear motion (e.g., motion along the axis X of the massager device 900), and the second actuator 93 lb can be an electric motor configured to produce and/or generate low-force, low displacement movement but in a high range of frequencies or frequency bandwidth. In some embodiments, the first actuator 931a and the second actuator 931b can be mechanically coupled in series, with the first actuator 931a and the second actuator 931b being configured to be independently controlled by the control unit 950. The combined actuators can then generate and/or produce a high force, long stroke output, and high bandwidth output signal. In other embodiments, the first actuator 931a and the second actuator 931b can be mechanically coupled in parallel. In this configuration, operation of one actuator 931a, 931b does not require moving the mass associated to the other actuator 931a, 931b, which can allow for higher bandwidth for both actuators.

In some embodiments, the driving mechanism 930 can move the output mechanism 940 at a first frequency along a first axis (e.g., axis X) and also move output mechanism 940 at a second frequency along second axis (e.g., an axis off axis from axis X, such as an axis perpendicular to axis X). In some embodiments, the massager device 900 can be configured to limit the movement of the output mechanism to a single direction (e.g., along an axis X). While note depicted, the massage device 900 can include guiding channels, grooves, and/or housings, guiding posts and/or rods, elastic and/or compliant elements, bearings, flexures, etc. for limiting movement of the output mechanism 940 along axes that are offset from the axis X.

The sensor(s) 932 can be configured to measure and/or record information associated with the massager device 900 and/or some of its components. For example, the sensor(s) 932 can measure a position and/or movement of a component of the driving mechanism 930 and/or output mechanism 940, or other data associated with one or more components of the massager device 900. Optionally, in some embodiments the output mechanism 940 can also include one or more sensor(s) 942 configured to measure movement, position, and/or acceleration of a component of the output mechanism 140. More specifically, a position sensor may indicate absolute position (location) or relative position (displacement), in terms of linear travel, rotational angle, or three-dimensional space. In some embodiments, a position sensor can be a capacitive displacement sensor that measure variations of capacitance between two points (e.g., the sensor and a conductive target). In some embodiments, a position sensor can be an inductive sensor that uses a coil and an oscillator to create a magnetic field in the close surroundings of the sensing surface and produce a dampening of the oscillation amplitude in response to the position of an actuator. In some embodiments, a position sensor can be an optical component such as a laser doppler vibrometer that directs a laser beam at surface of interest, and the vibration amplitude and frequency are extracted by the doppler shift of the of a reflected laser beam frequency due to the motion of the surface. In some embodiments, a position sensor can be a linear variable differential transformer (LVDT), a piezoelectric transducer, a potentiometer, an ultrasonic sensor or the like. In some embodiments, the sensor(s) 932 and/or 942 can include an accelerometer (e.g., for measuring acceleration of a component), a force sensor (e.g., for measuring loads and/or forces applied to a component), a temperature sensor (e.g., for measuring a temperature of a component), etc.

The sensor(s) 932 and/or 942 can be used to monitor feedback from operating the massager device 900, e.g., feedback from applying the massager device 900 to skin and/or muscle tissue. In some embodiments, the control unit 950, in response to receiving data from the sensor(s) 932 and/or the sensor(s) 942 can be configured to adjust the operation of the massager device 900 (e.g., adjust a parameter of the signal waveform used to drive the driving mechanism 930, power off or on the massage device 900, etc.) based on the sensor(s) 932 and the sensor(s) 942 data.

In some embodiments, the control unit 950 can be configured to send data from the sensor(s) 932 and/or the sensor(s) 942 to other devices, e.g., a compute device 1190, user device 1180, and/or other devices, that can process and/or analyze the sensor data and provide recommendations to the user for adjusting the positioning and/or usage of the massage device 900.

Figure 10:
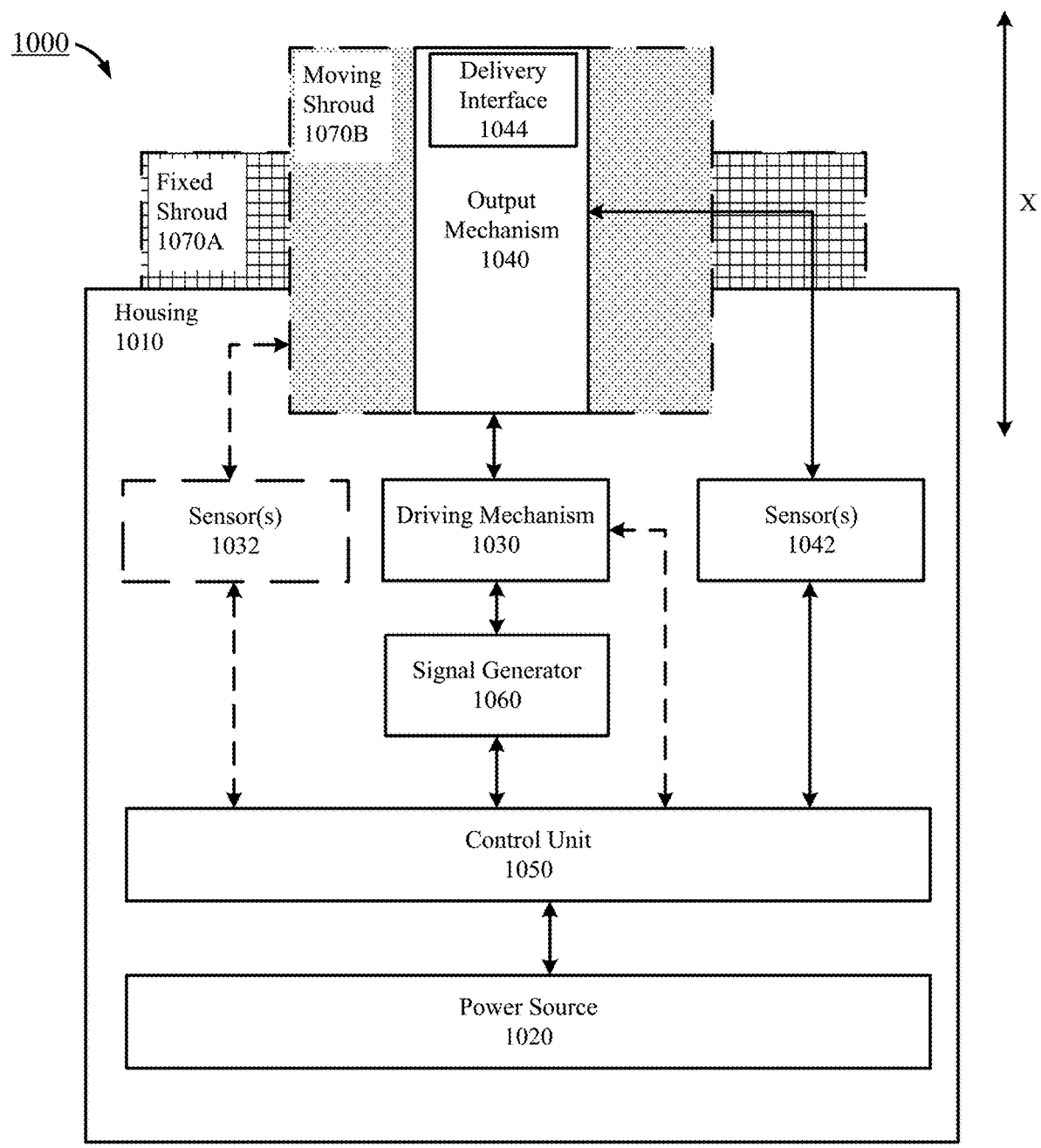
FIG. 10 is a schematic illustration of a measurement device, according to an embodiment.

FIG. 10 shows a schematic illustration of a measurement device or scanner 1000 according to an embodiment. The measurement device 1100 can be configured to measure and/or determine the state or condition of a tissue or muscle. The measurement device 1000 can include components that are structurally and/or functionally similar to components of the muscle management device 100. For example, the measurement device 1000 can include a housing 1010, a power source 1020, a driving mechanism 1030, an output mechanism 1040, one or more sensor(s) 1042, a control unit 1050, and a signal generator 1060. Optionally, the measurement device 1000 can include one or more sensor(s) 1032. Thus, portions and/or components of the measurement device 1000 may not be described again in detail herein.

The housing 1010 can define one or more areas (e.g., chambers) for accommodating and/or containing one or more components of the measurement device 1000, while providing one or more interfaces that enable coupling to other components of the measurement device 100. For example, in some embodiments the housing 1010 can include a compartment or chamber configured to accommodate and/or contain various components of the measurement device 1000 such as the power source 1020, the driving mechanism 1030, the one or more sensor(s) 1032, 1042, the control unit 1050, the signal generator 1060, a fixed shroud 1070, and/or a moving or movable shroud 1072. In some embodiments, the housing 1010 can include openings that allow portions of one or more components to extend outside of the housing. For example, the housing 1010 can include an opening that allows the output mechanism 1040 and/or moving shroud 1070B to extend out of the housing 1010. Certain components can also be directly coupled to or integrated with the housing 1010, such as, for example, the fixed shroud 1070A. In some embodiments, the fixed shroud 1070A can be an annular wall that is coupled to and/or integrated with the housing 1010 and at least partially surrounds the output mechanism 1040 and/or delivery interface 1044. Further details of the fixed shroud 1070A and the moving shroud 1072B are provided in latter sections.

The housing 1010 can have any suitable shape or configuration for housing and/or supporting the one or more components of the muscle management device 1000 and/or facilitating manipulation by a user. In some embodiments, the housing 1010 can be an elongate member having suitable cross-sectional shape, including, for example, circular, square, rectangular, and/or other polygonal cross-sectional shape. In some embodiments, the housing can have rounded edges and/or corners to increase ergonomics of the measurement devices 1000 such that a user may be able to manipulate the measurement device 100 with one hand (i.e., single-handed use)

The power source 1020 can be substantially similar to the power source 120 described above with reference to FIG. 1. For example, the power source 1020 can be any suitable energy source and/or energy storage device. In some embodiments, the power source 1020 can include one or more rechargeable batteries. In some embodiments, the measurement device 1000 can include one or more ports that enable connection between an external power source and one or more components of the muscle management device 1000. The external power source can be used to directly power the components of the measurement device 1000 and/or recharge the onboard power source 1020. While the power source 1020 is not depicted as being coupled to the signal generator 1060, the driving mechanism 1030, or the sensor(s) 1032, 1042, it can be appreciated that the power source 1020 can be operatively coupled to one or more of such components and can supply power to such components, as described with reference to power source 120 depicted in FIG. 1.

The control unit 1050 can be configured to activate and/or control the operation of one or more components of the measurement device 1000. While not depicted in FIG. 10, the control unit 1050 can include a memory, a processor, and/or an I/O device, similar to control unit 150 as depicted and described with reference to FIG. 1. In some embodiments, the control unit 1050 can be coupled to the power source 1020 to establish and/or interrupt a flow of electric power (e.g., an electric current) to operate one or more components of the measurement device 1000. The control unit 1050 can be coupled to the signal generator 1060 to control the signal generator 1060 to generate one or more current patterns or waveforms, which can be used to drive the driving mechanism 1030. The control unit 1050 can also be coupled to the sensor(s) 1032, 1042, e.g., to receive sensor data from the sensor9s) 1032, 1042 and to process and/or analysis such sensor data, as further described herein.

Figure 11:
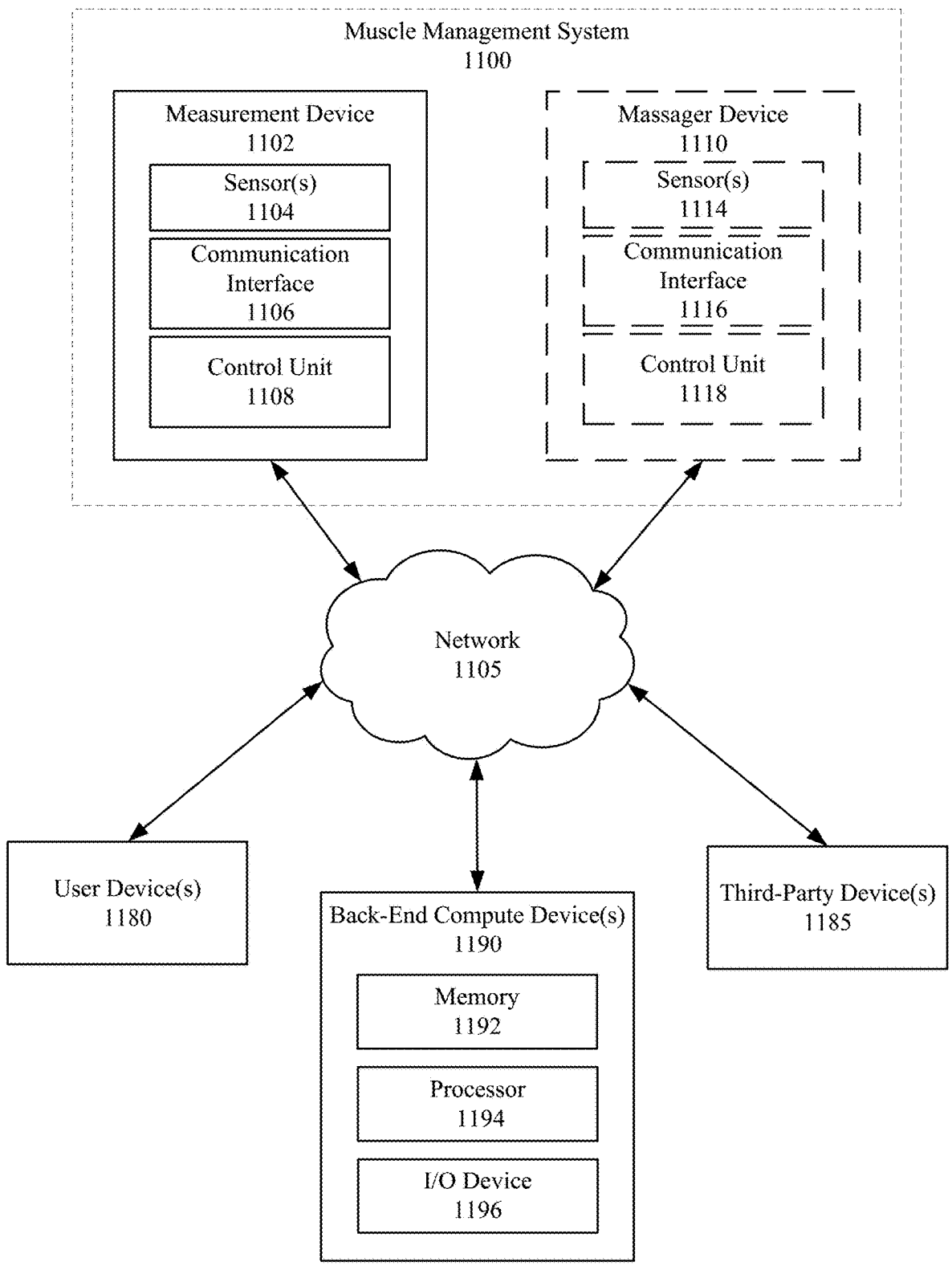
FIG. 11 schematically depicts a network of devices for measuring one or more characteristics of a tissue or muscle of a user and providing treatment of muscle fatigue and/or pain to the user.

In some embodiments, the control unit 1050 can be configured to receive and store instructions from an external device such as a user device, a back-end compute device, and/or a third-party device, as further described herein with reference to FIG. 11. Based on these instructions, the control unit 1050 can generate signals to control one or more components of the measurement device 1000. For example, the control unit 1050 can cause the signal generator 1060 to generate signals (e.g., waveforms) for activating movement of the output mechanism 1040, to adjust one or more parameters of the signals (e.g., waveform shape, frequency, amplitude, etc.), and/or to receive, process, analyze, and/or store, sensor data (e.g., data received from the sensor(s) 1032 and the sensor(s) 1042). In some embodiments, the control unit 1050 can be configured to receive data from the sensor(s) 1032, and 1042, compare such data to each other and/or reference values (or otherwise process and/or analysis such data), and cause the signal generator 1060 to generate signals (e.g., waveforms) for activating movement of the output mechanism 1040 and/or to adjust one or more parameters of the signals (e.g., waveform shape, frequency, amplitude, etc.).

The signal generator 1060 can be substantially similar to the signal generator 160 described above with reference to FIG. 1. For example, the signal generator 1060 can be operatively coupled to the control unit 1050 and can generate one or more signals that energize the driving mechanism 1030. In some embodiments, the signal generator 1060 can form part of or be integrated into the control unit 1050. The signal generator 1060 and/or circuitry coupled to the signal generator 1060 can be configured to generate one or more current waveforms that can be used to drive movement of a transducer, motor, or other components of the driving mechanism 1030.

The driving mechanism 1030 of the measurement device 1000 can be configured to drive movement of the output mechanism 1040 such that the output mechanism 1040 produces a mechanical output. The driving mechanism 1030 can be, for example, an electric motor, a transducer, or other suitable component for generating mechanical movement. In some embodiments, the driving mechanism 1030 can be disposed within an enclosure 1036 configured to provide mechanical support to the components of the driving mechanism. In some embodiments, the enclosure 1036 can be configured to couple one or more components of the measurement device 1000 such as the control unit 1050 and/or the signal generator 1060. The driving mechanism 1030 can be operatively coupled to the signal generator 1060, and to the output mechanism 1040. In some embodiments, the driving mechanism 1030 can be configured to receive an electrical signal (e.g., an electric current) from the signal generator 1060 and to generate mechanical movement along an axis X of the muscle management device 1000 (e.g., a longitudinal axis of the measurement device 1000). The mechanical movement can cause the output mechanism 1040 to produce an output signal (e.g., by moving back-and-forth or in an oscillatory or vibratory manner) that can be applied to a user to a characteristic of a tissue or muscle. In some instances, the driving mechanism 1030 can produce the output signal (and therefore measure data associated with the tissue or muscle) for a period of time of between about 2 seconds and about 5 minutes, including all values and subranges therebetween. For example, the driving mechanism 1030 can be configured to produce an output signal for a period of time of no more than about 2 seconds, no more than about 5 seconds, no more than about 10 seconds, no more than about 30 seconds, no more than about 1 min, no more than about 2 min, no more than about 3 min, no more than about 4 min, no more than about 5 min, inclusive of all values and ranges therebetween.

As described above with reference to the driving mechanism 130, there are various factors that can affect and/or determine the properties of the output signals of the output mechanism 1040 including, for example, the characteristics of electric motor of the driving mechanism 1030 (e.g., brushless motor, brushed motor, direct drive motor, linear motor, servo motor etc.), the ease of movement of the output mechanism (e.g., how frictionless is the movement of the output mechanism), the paths of energy dissipation (e.g., off-axis movement, heat, friction, etc.), and/or the direction of movement with respect to external forces (e.g., pressure and/or forces encountered by the output mechanism 1040 during use, gravitational forces, etc.). The measurement device 1000 can be configured to reduce or minimize factors (e.g., including friction, off-axis movement, etc.) that can affect the efficiency of the mechanical movement of the output mechanism 1040. For example, in some embodiments the measurement device 1000 can include one or more flexures, springs, or other elastic, compliant, or bearing components (not depicted in FIG. 10) configured to minimize or reduce off-axis movement of the output mechanism 1040 (e.g., movement not along the X axis). In some embodiments, the measurement device 1000 can include spiral flexures that have high off-axis stiffness and low in-line or on-axis stiffness. Accordingly, the flexures can be configured to efficiently drive the output mechanism 1040 along the X-axis but reduce or prevent movement of the output mechanism 1040 in directions lateral to or offset from the X-axis. In some embodiments, the flexures, springs, or other elastic and/or compliant components for reducing off-axis movement of the output mechanism 1040 can be made of any suitable material such as a metal, a metal alloy, a polymeric material, and/or a ceramic material. In some embodiments, such components can be mechanically coupled a shaft of the output mechanism 1040 which is configured to transfer the mechanical energy generated by the measurement device 1000 to a target area of a user. One or more flexures can be disposed inside the housing 1010 at one or more points along a length of the shaft and appropriately positioned to guide the movement of the shaft. Further details of flexures are described with reference to FIGS. 16A-19.

In some embodiments, the driving mechanism 1030 can be or include a Lorentz force motor (e.g., a linear Lorentz force or voice-coil motor). A Lorentz force motor can be lightweight and have a compact size that is particularly suitable for applications described herein. The Lorentz force motor can use a magnet and a coil (e.g., conductor) to convert electrical energy to mechanical energy according to the Lorentz force principle, e.g., that a current-carrying conductor located within a magnetic field can generate a force (Lorentz or electromagnetic force). The magnitude of the Lorentz force is proportional to the electrical current passing through the conductor and the magnetic flux produced by the magnet, producing linear force or torque output, and high acceleration or frequency actuation. In some embodiments, the use of a Lorentz motor in conjunction with one or more flexures can facilitate conducting highly sensitive mechanical dynamics analysis.

The output mechanism 1040 can be substantially similar to the output mechanism 140 described above with reference to FIG. 1. For example. in some embodiments the output mechanism 1040 of the measurement device 1000 can be configured to transfer the mechanical energy generated by the measurement device 1000 to a target area (e.g., skin and/or muscle area) of a user. The output mechanism 1040 can include a delivery interface 1044 that is configured to contact the skin and/or muscle of a user, e.g., at the target area. The output mechanism 1040 can be operatively coupled to the driving mechanism 1030 and be configured to move in response to movement generated by the driving mechanism 1030. In some embodiments, the output mechanism 1040 can be disposed outside of the housing 1010, while in other embodiments, a portion of the output mechanism 1040 can be disposed within the housing 1010 with a portion of the output mechanism 1040 extending from the housing 1010. In some embodiments, the output mechanism 1040 can move in and out of the housing 1010, in response to the mechanical movement of the driving mechanism 1030. In some embodiments, the output mechanism 1040 can include a shaft. As described above, at least a portion of the shaft can be disposed inside the housing 1010 and can be coupled with one or more flexures, springs, or other elastic and/or compliant components that can facilitate conduction or transfer of mechanical movements (e.g., highly sensitive mechanical dynamics) from the driving mechanism 1030 to the shaft.

The sensor(s) 1042 can be configured to measure and/or record information associated with the output mechanism 1040 of the measurement device 1000. The sensor(s) 1042 can be configured to measure and/or record a position of the output mechanism 1040, an acceleration of the output mechanism 1040, a strain on or force applied to a portion of the output mechanism 1040, or other data associated with the output mechanism 1040. For example, in some embodiments, a sensor 1042 can include a position sensor to detect the position of the shaft of the output mechanism 1040. The position sensor may indicate absolute position (location) or relative position (displacement), in terms of linear travel, e.g., along a direction of the axis X. In some embodiments, the position sensor can be a capacitive displacement sensor that measure variations of capacitance between two points (e.g., the sensor and a conductive target). In some embodiments, the position sensor can be an inductive sensor that uses a coil and an oscillator to create a magnetic field in the close surroundings of the sensing surface and produce a dampening of the oscillation amplitude in response to the position of an actuator. In some embodiments, the position sensor can be an optical component such as a laser doppler vibrometer that directs a laser beam at surface of interest, and the vibration amplitude and frequency are extracted by the doppler shift of the of a reflected laser beam frequency due to the motion of the surface. In some embodiments, the sensor(s) 1042 can include an accelerometer configured to measure an acceleration profile of the output mechanism. The accelerometer can be disposed on a shaft of the output mechanism 1040 and/or on a delivery interface 1044 of the output mechanism 1040. In some embodiments the position, acceleration, and/or force data measured by the sensor(s) 1040 can be used to calculate one or more characteristics of a tissue and/or muscle of a user, such as a stiffness, a dampening constant, a mass of a muscle, or other biomechanical properties of the tissue or muscle.

Optionally, the measurement device 1000 can include one or more sensor(s) 1032 and/or a moving or movable shroud 1070B. The sensor(s) 1032 can be coupled to the control unit 1050 and to the moving shroud 1070B. In some embodiments, the sensor(s) 1032 can include a position sensor configured to detect the position of the moving shroud 1070B. The position sensor may indicate absolute position (location) or relative position (displacement), in terms of linear travel, e.g., along a direction of the axis X. In some embodiments, the control unit 1050 (or another processor, such as a processor associated with a user device 1180, a back-end compute device 1190, and/or a third-party device 1185, as described with reference to FIG. 11) can receive data representative of the position (location) of the moving shroud 1070B from the sensor(s) 1032 and use that data to process and/or analyze data representative of the position (location) of the output mechanism 1040 (e.g., received from the sensor(s) 1042). For example, the moving shroud 1070B can provide a depth reference for measurements of muscle stiffness. The moving shroud 1070B can be configured to move (e.g., retract into the housing 1010 along axis X) as a user presses the measurement device 1000 against a surface of the user's skin. As such, the movement or displacement of the moving shroud 1070B can be indicative of a measure of depth or position of the measurement device 1000 relative to the user's muscle. The sensor(s) 1032 can be configured to measure this displacement of the moving shroud 1070B, e.g., by tracking a position of the moving shroud 1070B when the measurement device 1000 is placed against a surface of the user's skin. This depth information can provide greater dimensionality of data regarding muscle stiffness, when used in conjunction with the sensor(s) 1042. As described above, the sensor(s) 1042 can measure position, acceleration, force, and/or other data associated with the output mechanism 1040. Such data can be used to determine or evaluate one or more characteristics of a user's muscle, such as, for example, muscle stiffness. Accordingly, when used in conjunction with a moving shroud 1070B and sensor(s) 1032, output mechanism 1040 and sensor(s) 1042 can be used to provide richer information regarding muscle stiffness, including for example, stiffness as a function of depth or position (e.g., a depth that the output mechanism 1040 is displacing into tissue).

Having depth or position information can also enable the measurement device 1000 to be used for longer periods of time, e.g., to measure data associated with the output mechanism 1040 for a longer period of time and/or to account of variation due to changing depth or position. For instance, when a user is using measurement device 1000 to measure muscle stiffness, such measurements can be affected by the depth that the output mechanism 1040 is extending into the user's tissue (or the position of the output mechanism 1040 relative to the muscle). When the user presses the measurement device 1000 harder against the user's tissue, the forces acting upon the output mechanism 1040 (and therefore measurements of muscle stiffness or other muscle characteristics) are likely to be different than when the user presses the measurement device 1000 lighter against the user's tissue. In instances where measurements of muscle stiffness are conducted over a longer period of time, the user is likely to change the depth or position of the measurement device 1000. As such, measurement devices that cannot account of changes in depth or position cannot adjust for variation induced by such changes and are limited to collecting data regarding muscle stiffness or other muscle characteristics over a short period of time (e.g., a short period of time during which the user is unlikely to change the depth or position of the measurement device). The measurement device 1000, however, is capable of being used for longer periods of time, as the sensor(s) 1032 with the moving shroud 1070B can be used to capture depth or position data, and therefore be used to adjust the sensor data that is collected regarding muscle stiffness. By being able to collect muscle data for longer periods of time without suffering from noise or variations introduced by changing depth or position, the measurement device 1000 allows a user to collect measurements over time, e.g., to produce additional data regarding muscle characteristics. For example, sensor data collected over a longer period of time can be used to assess muscle damping over time (while controlling or adjusting for changes in depth or position), as well as other muscle characteristics over time.

In some embodiments, the moving shroud 1070B can be coupled to a cage, where the cage includes a plurality of compressible members that are configured to depress in a direction along a longitudinal axis of the output mechanism in response to a displacement of the moving shroud while reducing movement of the moving shroud in directions other than the direction along the longitudinal axis of the output mechanism.

In some embodiments, based on the data being received from the sensor(s) 1032 and the sensor(s) 1042, the control unit 1050 can adjust one or more parameters of the output signal (e.g., waveform shape, frequency, amplitude, etc.). In some embodiments, the sensor data can be processed and/or analyzed by a processor of the control unit 1050 (and/or some other processor, such as a processor associated with a user device 1180, a back-end compute device 1190, and/or a third-party device 1185, as described with reference to FIG. 11), and such processor can be configured to determine whether instructions for adjusting the measurement device 1000 (e.g., for collecting measurements) should be presented to the user, e.g., via the measurement device 1000 and/or a user device. For example, the sensor data collected by sensor(s) 1042 and/or sensor(s) 1032 can be used to determine that the measurement device 1000 has not be properly placed against a surface of the user's skin, and the processor can be configured to present instructions to the user to reposition the measurement device 1000.

In some embodiments, the measurement device 1000 can optionally include a fixed shroud 1070A. The fixed shroud 1070A can be used as a reference for how deep or how much to press the output mechanism 1040 against a surface of the user's skin. The fixed shroud 1070A can be coupled to and/or integrated with the housing 1010 and can be configured to remain stationary while the output mechanism 1040 is configured to move about the axis X. The fixed shroud 1070A can be any suitable mechanical structure coupled to the housing 1010 that can make contact with a surface of the user's skin. In some embodiments, the shroud 1070A can be an annular wall or structure (e.g., a tubular wall, elliptical wall, etc.) that surrounds or partially surround the output mechanism 1040 and provides a surface that can be placed in direct contact with the user's skin at a target area and/or region over which a tissue and/or muscle to be measured is located. In some embodiments, the shroud 1070A can be a polygonal shaped structure (e.g., triangular, square, etc. walls that surround the output mechanism 1040) that forms a boundary or wall around the output mechanism 1040. In some embodiments, the shroud 1070A can have an irregular cross-sectional shape defining a wall which is coupled to the housing 1010 and surrounds the output mechanism 1040.

The moving shroud 1070B can have a structure that is similar to the fixed shroud 1070A, e.g., have an annular structure that at least partially surrounds the output mechanism 1040.

The moving shroud 1070B can be movable relative to the housing, e.g., in the same X axis direction as the output mechanism 1040. In some embodiments, the measurement device 1000 can include a fixed shroud 1070A and a moving shroud 1070B, while in other embodiments, the measurement device 1000 can include one of the fixed shroud 1070B or the moving shroud 1070B. In some embodiments, the fixed shroud 1070A and the moving shroud 1070B can be positioned concentrically around the output mechanism 1040. Further details of such embodiments are described with reference to FIGS. 12-19.

FIG. 11 depicts a block diagram illustrating a muscle management system 1100 in communication with other devices via a network 1105. As described above, in some instances a massage device and a measurement device can be part of a muscle management system configured to provide treatment of muscle fatigue and/or pain to a user and/to determine the state or condition of a tissue or muscle of the user. As shown in FIG. 11, the muscle management system 1100 can include a measurement device 1102 configured to measure and/or determine the state or condition of a tissue or muscle and optionally a massager device 1110 configured to provide treatment of muscle fatigue and/or pain. The muscle management system 1100 can also include component(s) that are structurally and/or functionally similar to those of other massager devices and/or measurement devices described herein. For example, the massager device 1110 can be structurally and/or functionally similar to the massage device 900, and the measurement device 1102 can be structurally and/or functionally similar to the measurement device 1000. In particular, the massager device 1110 can include one or more sensor(s) 1114 (e.g., structurally and/or functionally similar to sensor(s) 932, 942) that can be configured to measure movement, acceleration, or other data associated with one or more components of the massager device 1110. The measurement device 1102 can include one or more sensor(s) 1104 (e.g., structurally and/or functionally similar to sensor(s) 1032, 1042) that can be configured to measure movement, acceleration, or other data associated with one or more components of the measurement device 1102.

In some embodiments, the massager device 1110 and the measurement device 1102 can optionally communicate with each other via the network 1105. For example, the measurement device 1102 can be used to apply an output signal to a target area to determine one or more characteristics of a tissue and/or muscle of a user (e.g., muscle stiffness), and the characteristics of the user's tissue and/or muscle can be communicated via the network 1105 to the massager device 1110. The massager device 1110 can analyze the data received from the measurement device 1102 and deliver a suitable treatment of muscle stiffness, fatigue and/or pain experienced by the user.

In some embodiments, the muscle management system 1100 can be configured to communicate with other devices, such as one or more back-end compute device(s) 1190, one or more user device(s) 1180, and one or more third-party device(s) 1185, etc., via the network 1105. The network 1105 can include one or more network(s) that may be any type of network (e.g., a local area network (LAN), a wide area network (WAN), a virtual network, a telecommunications network) implemented as a wired network and/or wireless network and used to operatively couple to any compute device, including the muscle management system 1100, the back-end compute device(s) 1190, the user device(s) 1180, and the third-party device(s) 1185.

The communication interfaces 1106, and 1116 can be configured to allow two-way communication between the measurement device 1102 and the massage device 1110, respectively, with an external device, e.g., a smart phone application (e.g., of the user device 1180), a third-party device 1185, and/or one or more other compute devices such as a local computer and/or a remote server. In some embodiments, the communication interfaces 1106, 1116 can provide wired communication with the external device, e.g., a USB or firewire interface. In some embodiments, the communication interfaces 1106, 1116 can also be used to recharge a power source (not shown), e.g., a rechargeable battery. In some embodiments, the communication interfaces 1106, 1116 can include components for wireless communication with the external device, e.g., Wi-Fi, Bluetooth®, low powered Bluetooth®, Zigbee and the like.

In some embodiments, the muscle management system 1100 can be configured to receive information and/or data via communication interfaces 1106 and 1116 from the back-end compute device(s) 1190, the user device(s) 1180, and/or the third-party device(s) 1185 via the network 1105. The data can include information related to the physiology of a user such as weight, height, gender, age, race, and the like; data related to the medical history of the user (e.g., general physical state, injuries, etc.); a history of treatments performed by the muscle management system 1100 on the user; and/or a set of instructions for measuring one or more tissues and/or muscles of the user or implementing a treatment on a tissue and/or muscle of the user. In some embodiments, the muscle management system 1100 can be configured to send data, e.g., measured by the sensor(s) 1114 and/or the sensor(s) 1104 via communication interfaces 1106 and 1116 to the back-end compute device(s) 1190, the user device(s) 1180, and/or the third-party device(s) 1185.

In some embodiments, the massager device 1110 and the measurement device 1102 of the muscle management system 1100 can each include an onboard control unit, such as, for example, a control unit 1118 and a control unit 1108, respectively. The control units 1108, 1118 can be structurally similar to other control units described herein. In particular, the control unit 1108 of the measurement device 1102 can be structurally and/or functionally similar to the control unit 1050 of the measurement device 1000, and the control unit 1118 of the massage device 1110 can be structurally and/or functionally similar to the control unit 950 of the massage device 900. Each control unit 1108, 1118 can include a memory, a processor, and/or an I/O device. In some embodiments, the processor of the control unit 1108 can be configured to process and/or analyze sensor data captured by the sensor(s) 1104, and/or the processor of the control unit 1118 can be configured to process and/or analyze sensor data captured by the sensor(s) 1114. For example, the processors of the control units 1108 and 1118 can be configured to process sensor data (e.g., filter, convert, etc.) prior to sending the sensor data to the back-end compute device(s) 1190, the user device(s) 1180, and/or the third-party device(s) 1185. Alternatively, the massager device 1110 and the measurement device 1102 of the muscle management system 1100 can be configured to send raw sensor data to the back-end compute device(s) 1190, the user device(s) 1180, and/or the third-party device(s) 1185. In some embodiments, control unit 1108 and/or 1118 can be configured to present information to a user, e.g., via an onboard display, audio device, or other output device. In some embodiments, control unit 1108 and/or 1118 can interface with the communication interface 1116 and the communication interface 1106, respectively, to transmit information to other device(s) (e.g., the user devices(s) 1180, the back-end compute device(s) 1190, or the third-party device(s) 1185) for presenting information to a user.

The back-end compute device 1190 can be configured to process and/or analyze the sensor data, e.g., received from the sensor(s) 1114 and the sensor(s) 1104. In some embodiments, the back-end compute device 1190 can be a nearby compute device (e.g., a local computer, laptop, mobile device, tablet, etc.) that includes software and/or hardware for receiving the sensor data and processing and/or analyzing the sensor data. In some embodiments, the back-end compute device 1190 can be a server that is remote from the muscle management system 1100 but can communicate with the muscle management system 1100 via the network 1105 and/or via another device on the network 1105 (e.g., one or more user device(s) 1180). For example, the muscle management system 1100 can be configured to transmit sensor data to a nearby device (e.g., a third-party device 1185 or a user device 1180), e.g., via a wireless network (e.g., Wi-Fi, Bluetooth®, Bluetooth® low energy, Zigbee and the like), and then that device can be configured to transmit the sensor data to the back-end compute device 1190 for further processing and/or analysis. In some embodiments, the compute device 1190 can determine muscle stiffness information, muscle damping information, and/or other muscle characteristic data, e.g., based on the sensor data. The compute device 1190 can present this data to a user, e.g., via an onboard display, or send such data to one or more other devices (e.g., measurement device 1102, massager device 1110, user device 1180, and/or third-party device 1185) to present to the user or other individuals (e.g., a massage therapist or other individual assisting the user in muscle therapy).

The back-end compute device 1190 can include a memory 1192, a processor 1194, and an input/out device (I/O) 1196 (or a multiplicity of such components). The memory 1192 can be, for example, a random-access memory (RAM), a memory buffer, a hard drive, a database, an erasable programmable read-only memory (EPROM), an electrically erasable read-only memory (EEPROM), a read-only memory (ROM), and/or so forth. In some embodiments, the memory 1192 stores instructions that cause processor 1194 to execute modules, processes, and/or functions associated with processing and/or analyzing sensor data from the muscle management system 1100 and/or providing instructions associated with conducting muscle measurements and/or treatments.

The processor 1194 of the back-end compute device 1190 can be any suitable processing device configured to run and/or execute functions associated with processing and/or analyzing sensor data from the muscle management system 1100. For example, the processor 1194 can be configured to process and/or analyze sensor data (e.g., received from sensor(s) 1104 and sensor(s) 1114), to determine one or more characteristics of a tissue and/or muscle of a user, such as a stiffness, damping, etc. The processor 1194 can also be configured to generate and provide instructions associated with conducting muscle measurements and/or treatments. The processor 1194 can be a general purpose processor, a Field Programmable Gate Array (FPGA), an Application Specific Integrated Circuit (ASIC), a Digital Signal Processor (DSP), and/or the like.

The I/O device 1196 of the back-end compute device(s) 1190 can include one or more components (e.g., a communication or network interface) for receiving information and/or sending information to other devices (e.g., the muscle management system 1100, the user device(s) 1180, the third-party device(s) 1185). In some embodiments, the I/O device 1196 can optionally include or be operatively coupled to a display, audio device, or other output device for presenting information to a user. In some embodiments, the I/O device 1196 can optionally include or be operatively coupled to a touchscreen, a keyboard, or other input device or receiving information from a user.

The user device(s) 1180 can be compute device(s) that are associated with a user of a muscle management system 1100. Examples of user device(s) 1180 can include a mobile phone or other portable device, a tablet, a laptop, a personal computer, a smart device, etc.). In some embodiments, a user device 1180 can receive sensor data from the muscle management system 1100 and process that sensor data before passing the sensor data to the back-end compute device 1190. For example, a user device 1180 can be configured to reduce noise (e.g., filter, time average, etc.) raw sensor data. In some embodiments, a user device 1180 can be configured to analyze the sensor data and present (e.g., via a display) information representative of or summarizing the sensor data. In some embodiments, a user device 1180 can provide muscle stiffness information, muscle damping information, and/or other muscle characteristic data to a user. In some embodiments, a user device 1180 can transmit the sensor data to the back-end compute device 1190, which can analyze the sensor data and send information representative of or summarizing the sensor data back to the user device 1180 for presenting (e.g., via a display) to a user.

The third-party device(s) 1185 can be compute device(s) associated with other individuals or entities that have requested and/or been provided access to a user's data. For example, the third-party device(s) 1185 can be associated with massage therapists or other individuals assisting a user in muscle management (e.g., healthcare professional, personal caretaker, etc.). The user can select to have certain third parties have access to the user's muscle management data (e.g., including data obtained from sensor data collected by the muscle management system 1100). The third parties can then track the user's information to determine whether the user requires and/or needs certain interventions, treatments, or care.

Figure 2A:
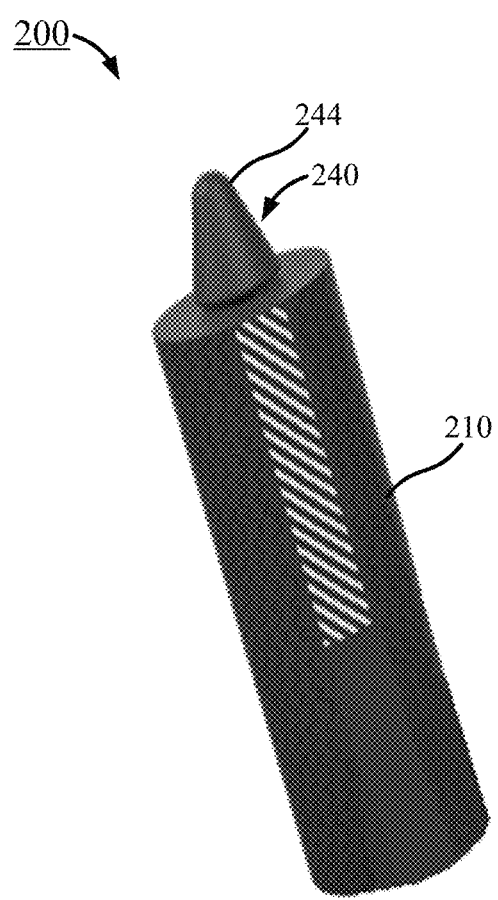
FIG. 2A is an illustration of a muscle management device according to an embodiment.
Figure 2B:
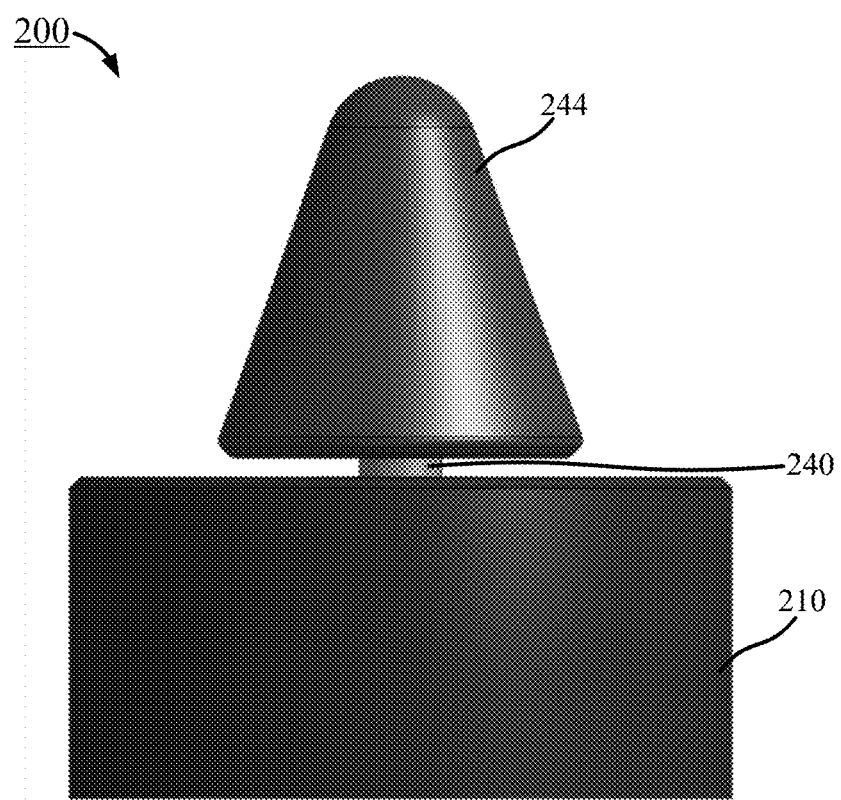
FIG. 2B is an enlarged view of a distal portion of a muscle management device according to an embodiment.

FIGS. 2A and 2B depict an example muscle management device 200, according to embodiments described herein. The muscle management device 200 can include components that are functionally and/or structurally similar to other massage devices described herein (e.g., muscle management device 100). For example, muscle management device 200 can include a housing 210 (that houses one or more of a power source, a control unit, a signal generator, a sensor, or a driving mechanism (not depicted)) and an output mechanism 240 including a tip 244 (e.g., delivery interface). The tip 244 can be configured to contact the skin and/or muscle of a user, e.g., to impart forces upon the skin and/or muscle in response to movement of the output mechanism 240.

FIG. 2B depicts an enlarged view of a front or distal end of the muscle management device 200, i.e., an end of the muscle management device facing the user. As shown in FIG. 2B, the output mechanism 240 can be implemented as a shaft that extends into the tip 244 (e.g., an interchangeable tip). The tip can be configured to apply sufficient pressure to skin and/or tissue without significant deformation. In some embodiments, the tip can be formed of a flexible, elastic and/or compliant material, such as rubber and/or a polymer. The tip can have a conical shape that terminates in a point that is configured to apply pressure to skin and/or muscle. While a conical shape is depicted in FIG. 2B, it can be appreciated that any suitable shape, including other shapes described above with reference to delivery interface 144, can be used. In operation, the output mechanism 240 and the tip 244 can move in a direct along a longitudinal axis of the muscle management device 200.

The housing 210 can have an elongate shape, e.g., suitable for being gripped for head by a user in one hand. In some embodiments, the housing 210 can have a textured or high friction (e.g., rubber) surface to facilitate easy gripping and/or manipulation of the device. In some embodiments, the housing 210 can have a circular cross-sectional shape, while in other embodiments, the housing 210 can have a ellipsoid, square, and/or other suitable cross-sectional shapes. In some embodiments, the housing 210 can form a seal (e.g., a water tight seal) to protect internal components of the muscle management device 200 from external environmental conditions (e.g., water, dust, heat, etc.).

Figure 3:
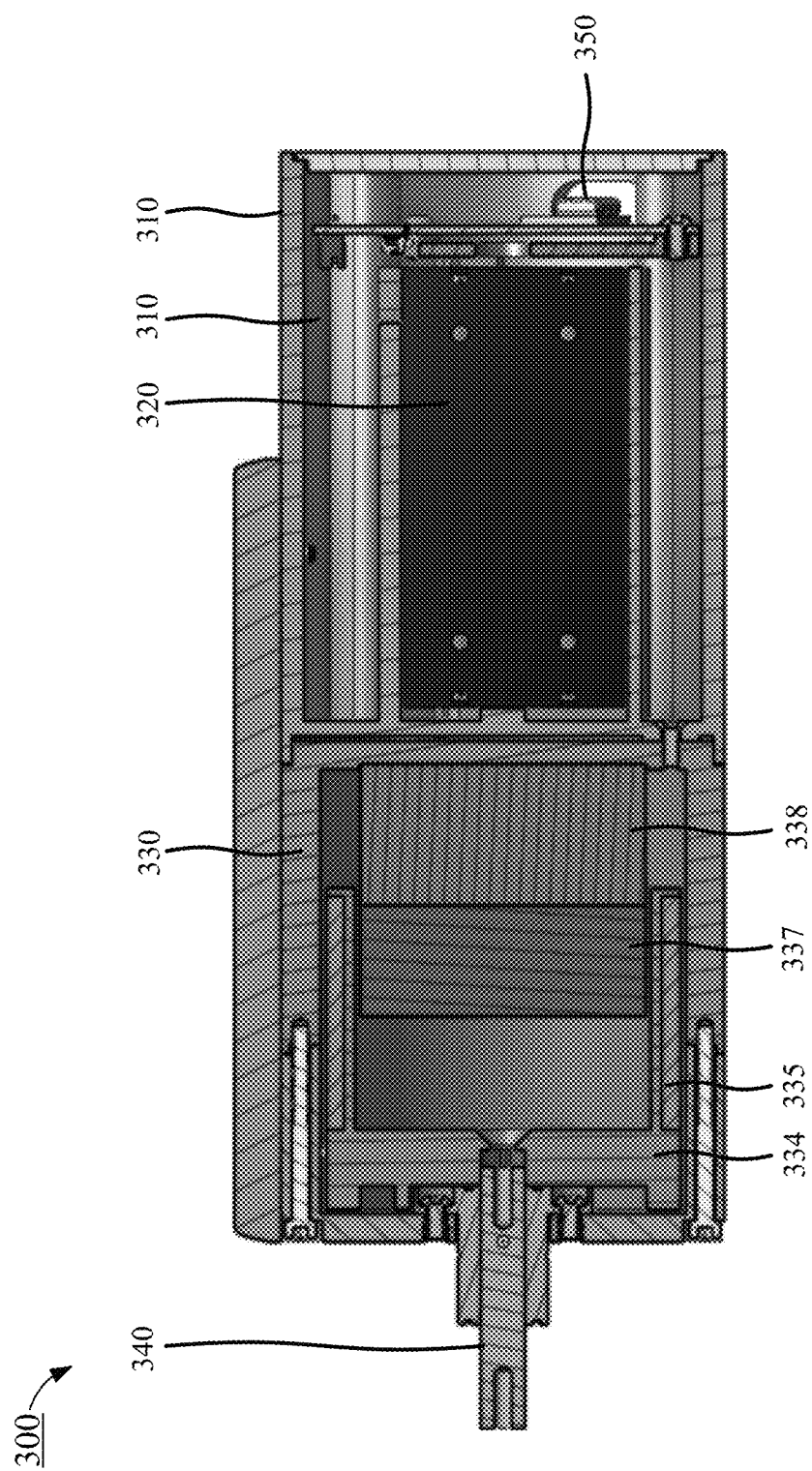
FIG. 3 is an illustration of a cross-sectional view of a muscle management device according to an embodiment.
Figure 4:
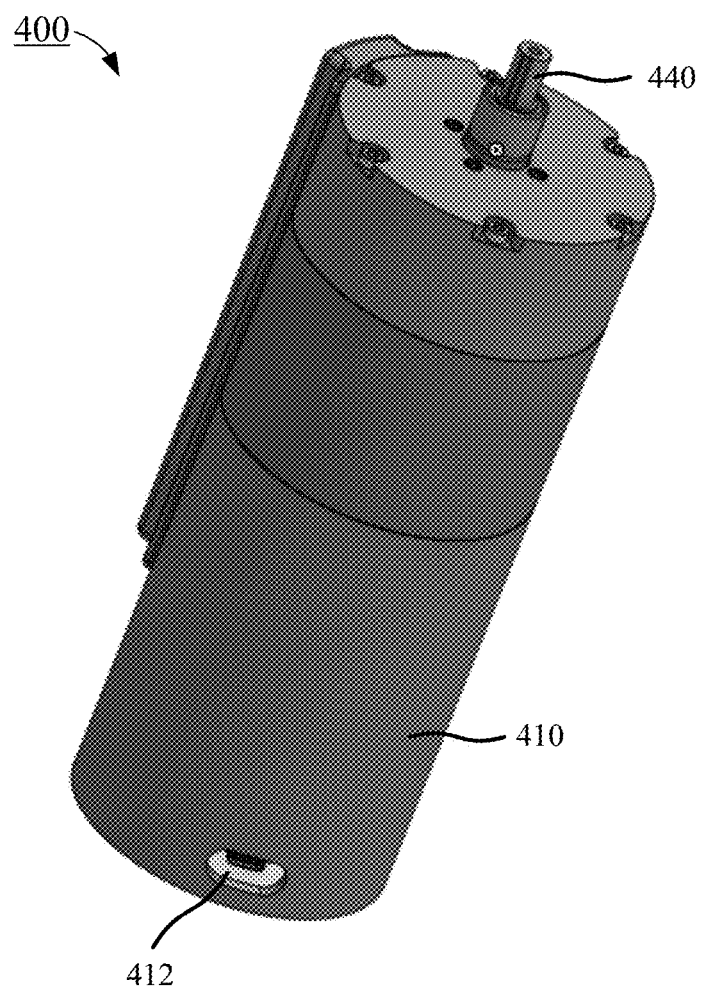
FIG. 4 is an illustration of a perspective view of the muscle management device of FIG. 3.

FIGS. 3 and 4 illustrate a muscle management device 300, according to some embodiments. The muscle management device 300 can include components that are structurally and/or functionally similar to other muscle management devices described herein, e.g., muscle management devices 100, 200, etc. For example, the muscle management device 300 can include a housing 310, a power source 320, a driving mechanism 330, an output mechanism 340, and a control unit 350. Portions and/or aspects of such components may not be described again herein.

The housing 310 can be similar to housing 110, and in particular has a cylindrical shape that defines two chambers or compartments for accommodating various components of the muscle management device 300. As depicted in FIG. 3, the housing 310 includes a bottom chamber 312 (or first chamber) that accommodates the power source 320 and the control unit 350. The control unit 350 can be mounted on an integrated circuit board that can include a signal generator and/or additional circuitry for generating a signal waveform, as further discussed below. In some embodiments, the bottom chamber 312 can be accessible via a cap 314. The cap 314 can be designed to open and close (or be removed or attached to the muscle management device 300) to provide access to and/or to facilitate removing various components of the muscle management device 300. For example, opening or removing the cap 314 can allow a user to gain access to the control unit 350, power source 320, etc.

As depicted in FIG. 3, the housing 310 also includes a top chamber 316 (or second chamber) that accommodates the driving mechanism 330 and at least a portion of the output mechanism 340. The top chamber 316 can include an opening 319 that accommodates at least a portion of the output mechanism 340. The output mechanism 340 implemented as a shaft can extend out from the top camber 316 of the housing 310. In some embodiments, the bottom chamber 312 and the top chamber 316 of the housing 310 can be detachably coupled to one another, e.g., via or more fastening elements (e.g., screws, pins, threads, etc.), adhesive, and/or other attachment mechanisms. In other embodiments, the bottom chamber 312 and the top chamber 316 can be integrated together. While not depicted, the housing 310 can include an exterior shell, e.g., such as the one depicted in FIGS. 2A and 2B.

The housing 310 can include a side panel or compartment 318 that housing additional components of the muscle management device 300. For example, in some embodiments, the side panel 318 can be configured to house wires and/or other electrical connections of the muscle management device 300. In some embodiments, the housing 310 can include one or more ports that can enable coupling between interior and exterior components of the muscle management device 300. For example, a port 312 can be configured to couple the muscle management device 300 (or specifically, the control unit 350 of the muscle management device 300) to an external compute device (e.g., for sending and/or receiving data) and/or external power sources.

The muscle management device 300 can include an onboard power source 320 that can be substantially similar in at least form and/or function to the onboard power source 120 described above with reference to FIG. 1. In some embodiments, the power source 320 can include one or more batteries. In some embodiments, an external power source can be used to directly power the components of the muscle management device 300 and/or recharge the onboard power source 320. The batteries can be recharged via port 312 and/or by removing cap 314 such that the batteries can be removed for replacement and/or recharging.

The control unit 350 can be functionally and/or structurally similar to control unit 150. For example, the control unit 350 can be configured to activate and/or control the operation of one or more components of the muscle management device 300, e.g., by receiving electrical signal(s) from and/or sending electrical signal(s) to other components of the muscle management device 300. The control unit 350 can include a memory, a processor, and an I/O device. The memory of the control unit 350 can store instructions that cause the processor of the control unit 350 to execute modules, processes, and/or functions associated with operating one or more components of the muscle management device 300. Such modules, processes, and/or functions can include, for example, processing and/or analyzing sensor data (e.g., received from sensor(s) 132), causing a signal generator and/or additional circuitry to generate signals (e.g., waveforms) for inducing movement of the output mechanism 340, adjusting one or more parameters of the signals (e.g., waveform shape, frequency, amplitude, etc.), and generating feedback and/or instructions to provide to a user to facilitate application of the muscle management device 300 to treat one or more muscle conditions. The I/O device of the control unit 350 can include one or more components for receiving information and/or sending information to other components of muscle management device 300 and/or other devices. For example, the I/O device can include or be operatively coupled to a display, audio device, or other output device for presenting information to a user and/or include a communication or network interface for communicating with other components of the muscle management device 300 and/or external compute devices.

As depicted in FIG. 3, the control unit 350 can be mounted on an integrated circuit board. The integrated circuit board can include a signal generator (e.g., similar to signal generator 160) and/or additional electrical components (e.g., amplifiers, transistors, switches) that can produce an electrical signal for energizing the driving mechanism 330. In some embodiments, the control unit 350 can be configured to generate electrical signals (or cause a signal generator to generate electric signals) that can be used to energize the driving mechanism 330. The electrical signals may include a stored pattern or sequence of operation, e.g., the stored instructions accessed by the control unit 350 that may be used to generate a series of electrical signals that are sent to the driving mechanism 330 to cause the driving mechanism 330 to turn "on" or "off." The stored pattern or sequence can be uniquely tailored to a specific user, e.g., based on historical data of the user (e.g., usage data collected, accumulated, and stored for that particular user) and/or information inputted by the user and/or therapist into the muscle management device. The electrical signals delivered to the driving mechanism 330 can cause the driving mechanism 330 to produce mechanical motion or a mechanical output that is suitable for treating one or more conditions associated with a muscle area (e.g., massaging a muscle area of a user).

In some embodiments, the control unit 350 can be coupled to a sensor (e.g., similar to sensor 132) that can measure various information associated to the muscle management device 300. In some embodiments, the sensor can be configured to measure one or more properties associated with the driving mechanism 330 and/or output mechanism 340, such as, for example, voltage, current, impedance, position, acceleration, force, and the like. The sensor data can be analyzed by the control unit 350 and, depending on information inferred from such sensor data, the control unit 350 can be configured to change one or more parameters or properties of the electrical signals that energize the driving mechanism 330 and/or mechanical output, such that one or more characteristics of the therapy (e.g., massage) applied on a user can be adjusted. In some embodiments, the control unit 350 can receive information measured by the sensor, analyze said information, and provide feedback to a user related to the therapy (e.g., massage) being executed. For example, the sensor can measure the force that the driving mechanism 330 imparts to one or more muscles of user being massaged. The force data can be compared to reference force data associated to the user and/or associated with general guidelines of massage therapy, and used to determine the appropriate feedback to provide to the user. For example, the force data can be used to determine a condition (e.g., status, state) of a muscle area, muscle, or group of muscles being massaged and/or determine an appropriate type of massage or other therapy (e.g., heat compress) required to treat the particular muscle condition.

The driving mechanism 330 of the muscle management device 300 can configured to drive movement of the output mechanism 340. The driving mechanism 330 can be implemented as a Lorentz force motor (e.g., a linear Lorentz force or voice-coil motor). The Lorentz force motor includes a bobbin or spool 334, a coil 335, a flux guide 337, and a magnet 338. The bobbin 334 can be a structure with a cylindrical shape that is configured to support the coil 335. The bobbin 334 can have a hollow interior volume that is fabricated from an insulating material, such as, for example, glass, Teflon, phenolic resins, polybutylene terephthalate, polyethylene terephthalate, polyphenylene sulfide and the like. The diameter of the bobbin 334 can be substantially equal to the inner diameter of the top chamber 316 such that movement of the bobbin 334 in a direction off axis from a longitudinal axis of the muscle management device 300 is minimized. The axial dimension or length of the bobbin 334 can be smaller than a length of the top chamber 316 of the housing 310, such that the bobbin 334 can move within a portion of the top chamber 316. Specifically, the difference between the length of the top chamber 310 and the bobbin 334 can define a displacement distance d that the bobbin can travel along the longitudinal axis of the housing 310. The coil 335 supported on the bobbin 334 can be made from a conductor material including, for example, a metal or a metal alloy such as Nickel, copper, titanium and stainless steel. In some embodiments, the coil 335 can be covered by an outer layer of a nonconductive and thermally insulating material such as, for example, nylon, polyphenylene sulfide (PPS) and other thermoplastics.

During operation, the coil 335 can receive electrical signals (e.g., a current waveform) from the control unit 350 (and/or signal generator and circuitry of the muscle management device 300). The electrical signals can vary according to a predefined profile, e.g., a waveform having a frequency, amplitude, and shape. When the electrical signals are passed through the coil 335, the coil 335 can be configured to generate a modulated magnetic field that interacts with the magnetic field of the magnet 338 to drive movement of the bobbin 334 (and the coil 335 mounted on the bobbin 334). In some embodiments, the magnitude of the Lorentz force can be proportional to the electrical current passing through the coil 335 and the magnetic flux produced by the magnet 338, producing a force that causes the bobbin to travel a distance d along the axial direction of the housing 310. Reversing the direction of the current passing through the coil 335 can produce a change in the direction of the Lorentz force, which in turn causes the bobbin 334 to travel in the opposite direction along the longitudinal axis of the housing 310. Accordingly, the characteristics or properties of the electrical signals generated by the control unit 350 (and/or signal generator and circuitry of the muscle management device 300) can be adjusted to produce desirable mechanical output from the muscle management device 300. While not depicted, in some embodiments, the bobbin 334 can be supported at an equilibrium position within the chamber 316, e.g., by one or more suspension elements (e.g., a spring, an elastic and/or compliant member, etc.).

In some embodiments, a flux guide 337 can be used to reduce stray magnetic flux. The flux guide 337 can be, for example, an end plate that is attached to the magnet 338. A driving mechanism with a magnet may have magnetic field lines that stray far from the magnet and cause the driving mechanism to be magnetically attracted to metallic objects. This attraction can produce undesirable side effects and make the muscle management device 300 cumbersome to use. The flux guide 337 can reduce such stray magnetic flux, e.g., such that the muscle management device 300 can be used close to other metallic objects without being attracted as much to those objects. Furthermore, flux guide 337 can be used to direct the magnetic field lines out from an end of the magnet 338 in a direction perpendicular to (e.g., toward) the coil 335 generating the magnetic fields such that more of the magnetic field lines are directed to enabling movement of the bobbin 334, while reducing stray dissipation or leakage of magnetic field lines in a direction parallel to the coil (e.g., not toward the coil 334).

In an alternative embodiment, the driving mechanism 330 can include a moving magnet and a fixed coil. For example, a magnet can be suspended within a chamber of the housing with a fixed coil disposed about the magnet. Driving a current waveform through the coil can similarly drive movement of the magnet, causing the magnet to mechanically move (e.g., back and forth) within the chamber. In such embodiments, the magnet can be coupled to the output mechanism, thereby imparting its mechanical motion onto the output mechanism.

The output mechanism 340 can be functionally and/or structurally similar to the output mechanisms 140, 240 described with reference to FIGS. 1, 2A, and 2B. The output mechanism 340 can include a shaft that extends distally from the housing 310. The output mechanism 340 can include a proximal portion that is disposable within the housing 310 and coupled to the bobbin 334. The other end (or distal end) of the output mechanism 340 can be coupled to a tip (not depicted) that can be configured to contact skin and/or muscle or a user. The shaft of the output mechanism 340 can be disposed partially within a bearing 341 that constrains the movement of the shaft substantially to a longitudinal axis of the bearing 341.

Figure 5:
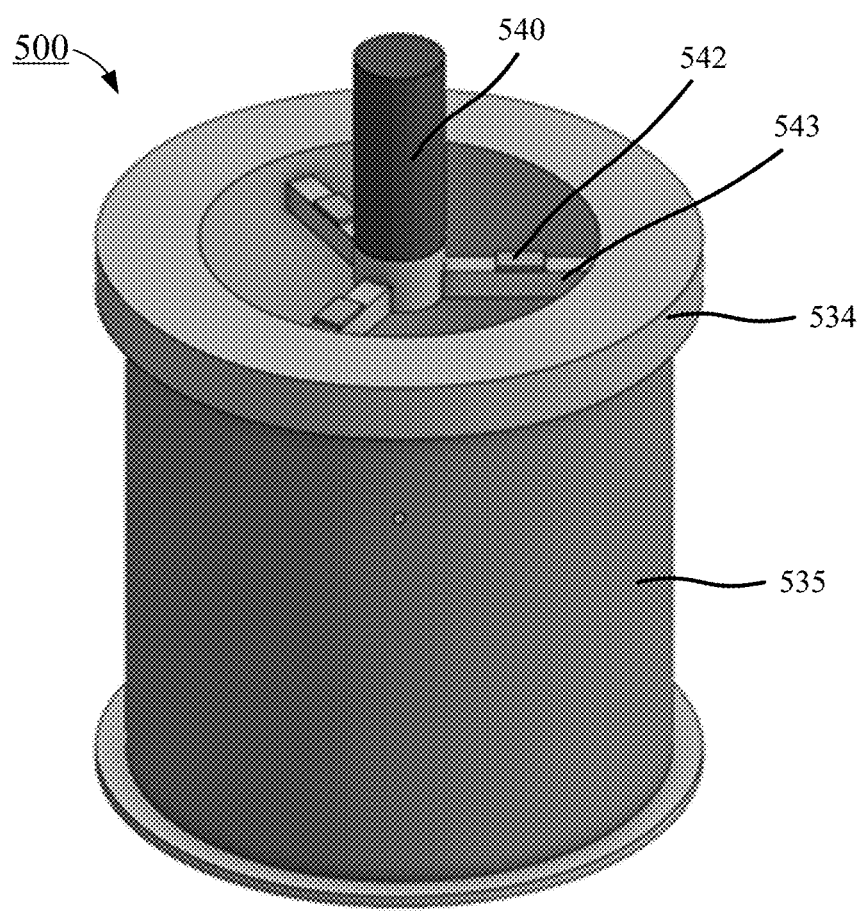
FIG. 5 is an illustration of a perspective view of portions of an output mechanism and a driving mechanism of a muscle management device according to an embodiment.
Figure 6:
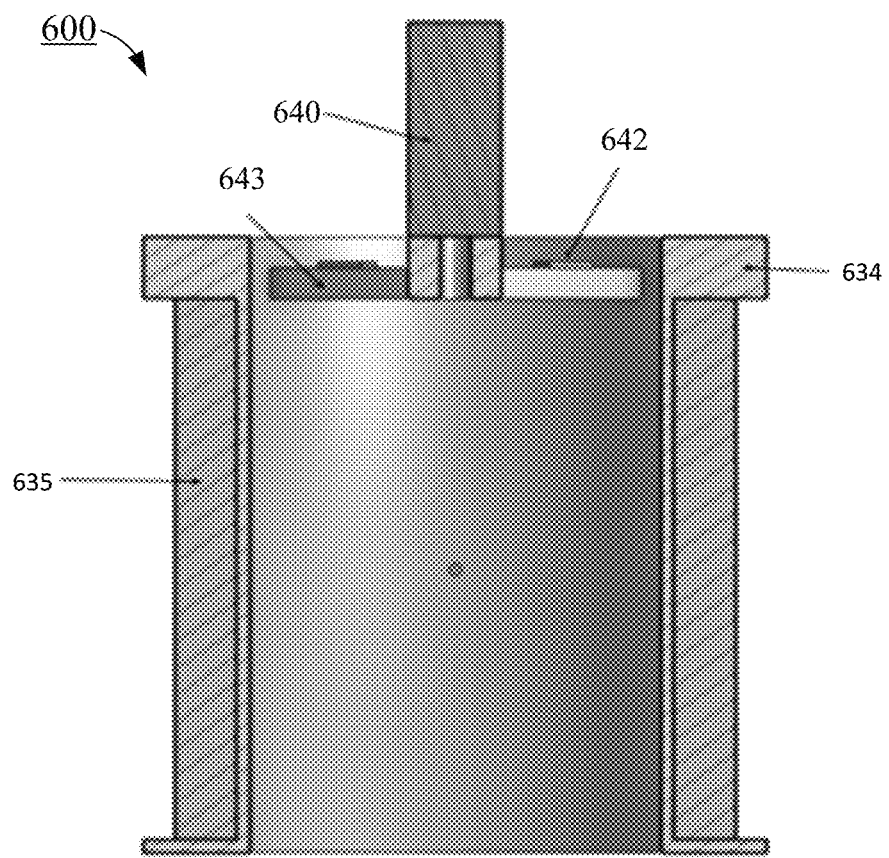
FIG. 6 is an illustration of a cross-sectional view of the portions of the output mechanism and the driving mechanism shown in FIG. 5.

FIGS. 5 and 6 depict a portion of a driving mechanism 530 of an example muscle management device, according to embodiments. The driving mechanism 530 can be similar to other driving mechanisms described herein, including, for example, driving mechanisms 130, 330. For example, the driving mechanism 530 can include a bobbin 534 (e.g., spindle, wheel, cylinder) that supports a coil 535. The bobbin 534 and the coil 535 can be part of a Lorentz motor or other type of electromagnetic motor, such as that described with reference to FIGS. 3 and 4.

The bobbin 534 can include a plurality of support members 543 (e.g., spokes), that together support a coupling between a shaft 540 of an output mechanism (e.g., output mechanism 140, 340) and the bobbin 534. The support members 543 can extend radially from a central longitudinal axis of the bobbin 534 and be arranged evenly about a circumference of the shaft 540. Each of the support member 543 can be flexural supports, e.g., supports that can deform, such that the supports can deform in response to a force applied to the shaft 540. In operation, when a user applies a tip of the output mechanism against skin and/or muscle, forces exerted by the skin and/or muscle are received by the shaft 540 and can cause deformation in one or more of the support members 543. These deformations can be measured by one or more strain sensors 542 (e.g., strain gauges) that are positioned on each support member 543.

The deformations measured by the strain sensors 542 can be used to determine (e.g., calculate, measure) an output force of the bobbin 534 and/or forces exerted by skin and/or muscle upon the output mechanism or shaft 540. The strain sensors 542 can be operatively coupled to a control unit (e.g. control unit 150), and the control unit can be configured to determine a force associated with the bobbin 534 and/or output mechanism (including shaft 540) based on data received from the stain sensors 542. In some embodiments, the control unit can control a signal generator (e.g., signal generator 160) to adjust a signal being passed through the coil 535 based on the determined force, such that one or more properties of the output signal (e.g., frequency, amplitude, force, pattern) can be adjusted to better apply therapy to particular skin and/or muscle. In some embodiments, the control unit can provide feedback to a user based on the determined force, e.g., to allow the user to change a direction, orientation, and/or force applied by the muscle management device 100. For example, the control unit can inform the user that the force applied is outside of a predefined range of values, below a predefined minimum, and/or above a predefined maximum value, such that the user can adjust the degree or extent that the user is pressing or holding the device against skin and/or muscle.

In some embodiments, the measured force can be indicative of a state or condition of tissue and/or muscle with which the tip of the output mechanism is in contact. For example, muscle that is more knotted and/or tense may exert greater forces upon the output mechanism (and therefore, the shaft 540). The control unit, in such instances, can adjust an output of the muscle management device (e.g., an output of the shaft 540), for example, by adjusting one or more parameters of the signal generated by the signal generator, to provide more effective therapy and/or relief to the muscle. For example, the control unit can shift from applying a smoother signal (e.g., sinusoidal) to a more pulsatile signal (e.g., square or sawtooth signal) and/or alternate between different output signals to better target the muscle. Alternatively, the control unit can shift into applying greater forces and/or more steady forces to better penetrate into and target the muscle. In some embodiments, the control unit can provide feedback to a user, e.g., that the muscle management device has detected a muscle knot or muscle stiffness, and/or provide instructions to the user to apply greater pressure to the muscle and/or to engage in alternative forms of therapy (e.g., seeking a professional massage therapist, applying warm compresses, etc.).

In some embodiments, the measured force associated with the bobbin 534 and/or output mechanism (including shaft 540) can be indicative of improper and/or ineffective use of the muscle management device. For example, the measurements can indicate that a user is not applying sufficient pressure (e.g., that the force is below a predefined value) or apply too much pressure (e.g., that the force is above a predefined value) on skin and/or tissue. Alternatively or additionally, the measurements can indicate that the user is applying forces in an uneven or unbalanced manner and/or at angles or orientations that are less effective. In some embodiments, the strain sensors 542 can be positioned on support shafts that extend in different directions from the shaft 540, such that their measurements can be used to discriminate between lateral and axial forces. In such instances, the control unit can provide feedback to a user, e.g., that the muscle management device isn't being used effectively, and/or provide instructions to the user to adjust a direction, orientation, and/or force applied by the output mechanism on tissue and/or muscle (e.g., increase or decrease pressure, orient the device more orthogonally to a skin surface, etc.). Alternatively or additionally, the control unit can automatically adjust the electrical signal being used to power the muscle management device such that, for example, less or greater force is applied and/or force is being applied along a certain axis.

Figure 7A:
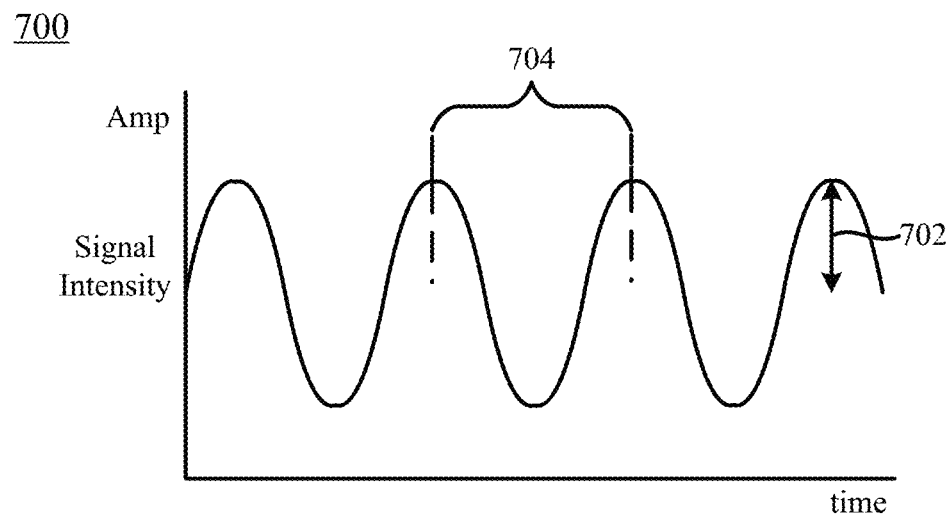
FIGS. 7A, 7B, and 7C depict three example waveforms that can be produced by a muscle management device according to an embodiment.
Figure 7B:
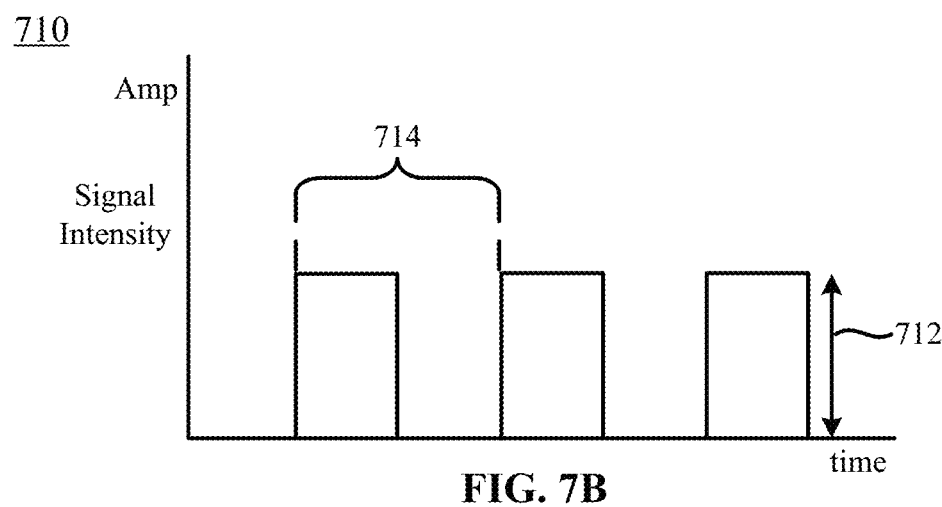
Figure 7C:
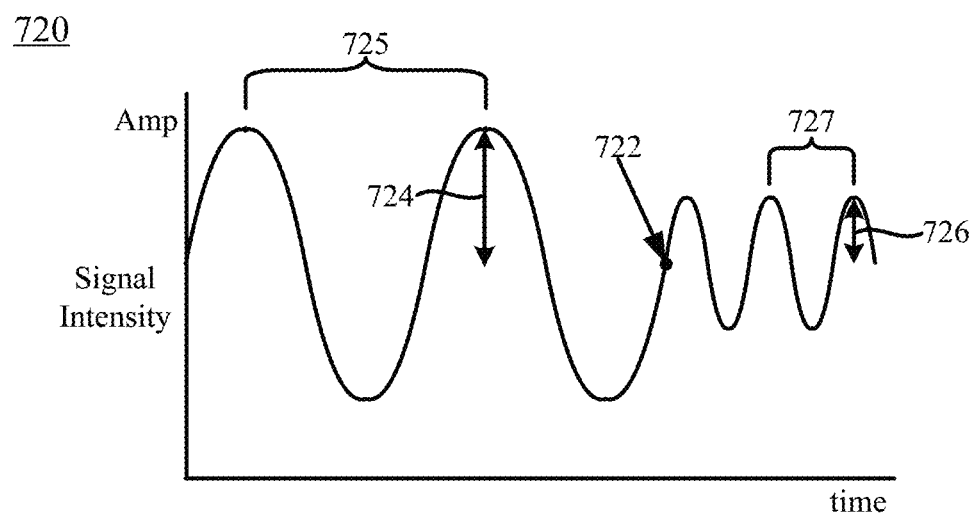

FIGS. 7A-7C depict different example waveforms of electrical signals that can be used to drive movement of an output mechanism of a muscle management device, according to embodiments described herein. The electrical signals depicted in FIGS. 7A-7C can be used with any of the muscle management devices described herein, including, for example, muscle management device 100, 200, or 300.

FIG. 7A depicts a sinusoidal waveform 700, with a wavelength 704 and an amplitude 702, that can, for example, be used to modulate a magnetic field to cause a portion of a driving mechanism (e.g., driving mechanism 130, 330, etc.) to move. For example, the sinusoidal waveform 700 can be passed through a coil (e.g., coil 335, 535) of a motor or transducer to generate a modulated magnetic field.

FIG. 7B depicts a pulse or square waveform 710, with a wavelength 714 and an amplitude 712. The square waveform 710 can be used to switch on and off a motor or transducer, e.g., a Lorentz force motor, a piezoelectric device, etc. The motor or transducer can switch on to generate pressure when activated by a pulse, and the pulse waveform can cycle at a certain frequency such that the pressure cycles on and off FIG. 7C depicts a sinusoidal waveform 700 that changes in frequency and amplitude following an event 722. Sinusoidal waveform 700 can have a first wavelength 725 and a first amplitude 724 during a first period of time prior to event 722, and a second wavelength 727 and a second amplitude 726 during a second period of time after event 722. Event 722 can represent a change in force and/or other parameter that is detected by a muscle management device (e.g., a control unit 150 of a muscle management device). Event 722 can be, for example, the detection of a muscle condition (e.g., a muscle knot), the detection of forces outside of predefined values, and/or detection of other conditions associated with the user, the muscle management device, and/or an external surrounding environment. Alternatively or additional, event 722 can be an input or instruction that is received from a user, e.g., to change a force, intensity, frequency, and/or other property of the output signal.

Figure 8:
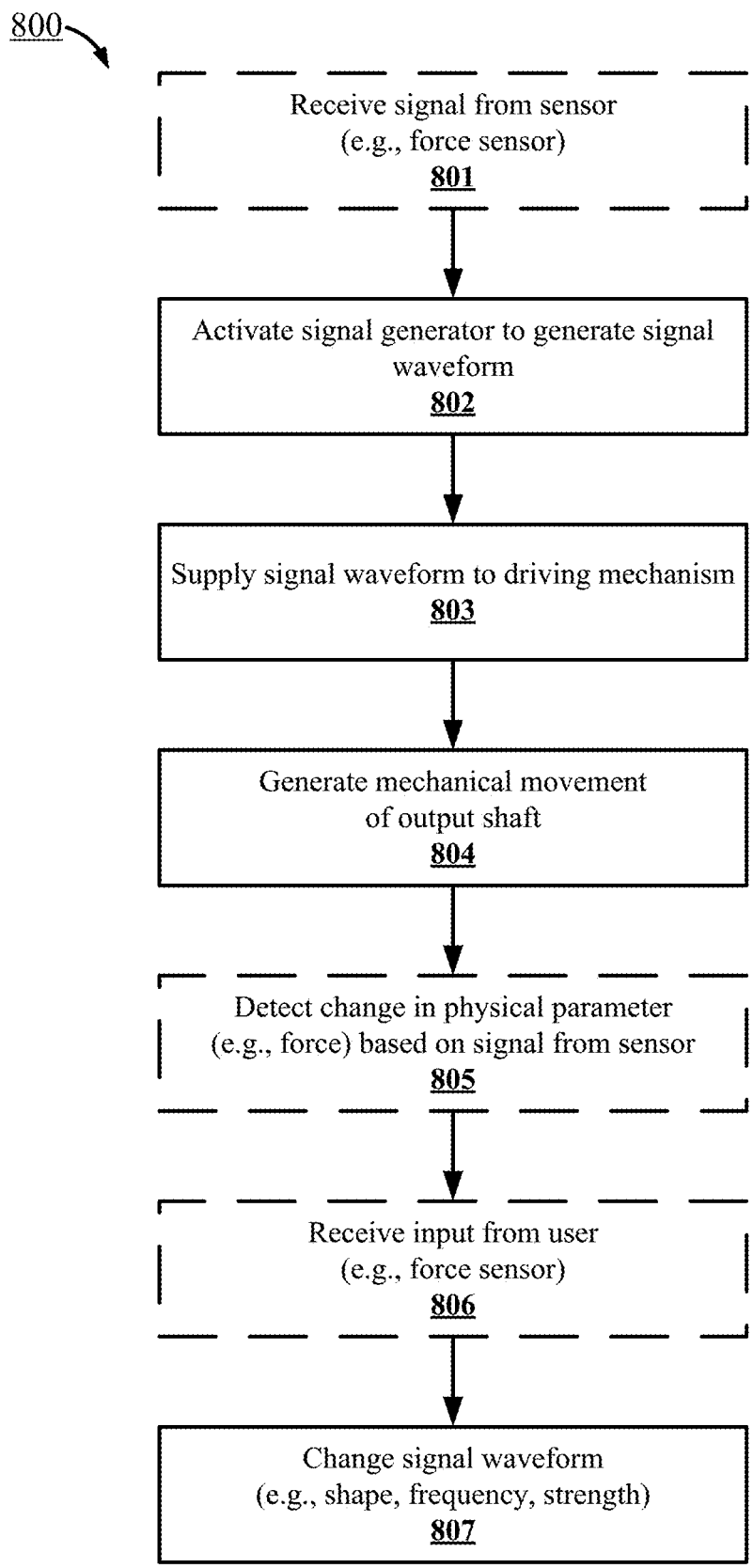
FIG. 8 is a flow chart of an example method performed by a muscle management device according to an embodiment.

FIG. 8 depicts a method 800 associated with operating a muscle management device (e.g., muscle management device 100, 200, 300, etc.), according to embodiments described herein. To use a muscle management device, a user can grip the muscle management device (e.g., along its housing) and orient the muscle management device such that a tip or delivery interface of the muscle management device is pointed toward a skin surface. The user can then press the muscle management device down onto the skin to apply a force to the skin and/or muscle. Optionally, in some embodiments, the muscle management device can receive a signal from a sensor (e.g., sensor 132, such as a force or strain sensor, a position sensor, etc.), at 801, and activate a signal generator to generate a waveform to drive movement of the tip of the muscle management device, at 802. For example, the control unit (e.g., control unit 150) of the muscle management device can detect when a user has pressed the muscle management device against skin and/or muscle (e.g., based on data received from one or more sensors) and automatically power on the device (e.g., control the signal generator and/or power source to energize the driving mechanism). Alternatively or additionally, in some embodiments, the muscle management device can receive an input from a user to power on, such as, for example, a user pressing a button on the muscle management device, a user using a mobile application (on a mobile device) to send an instruction to the muscle management device to power on, etc.

After generating the signal waveform, the waveform can be supplied to the driving mechanism (e.g., driving mechanism 130, 330, etc.) of the muscle management device, e.g., a Lorentz force motor, at 803. In particular, the signal waveform can be passed through a coil (e.g., coil 335, 535) to generate a magnetic field, which can be modulated based on the shape, frequency, amplitude, etc. of the waveform. The driving mechanism, in response to receiving the signal waveform, can generate mechanical movement of an output shaft (e.g., of an output mechanism), at 804. For example, in the case of a Lorentz motor or other electro-magnetic transducer, the modulated magnetic field generated by the coil can interact with a magnetic field of a magnet to cause the coil and/or another component of a motor or transducer to mechanically move (e.g., along an axis).

Optionally, the muscle management device can include one or more sensors that monitor one or more conditions or properties of the output shaft, the driving mechanism, the user, etc. For example, the muscle management device can include one or more strain sensors that are coupled to a bobbin (e.g., bobbin 534) of a driving mechanism, and the strain sensors can detect deformation along one or more portions of the bobbin and provide information indicative of forces being applied by or on the driving mechanism and/or output shaft. Based on data provided by the strain sensors, the compute device of the muscle management device can be configured to automatically adjust the signal waveform (e.g., adjust a shape, frequency, amplitude or strength) to change an output signal of the output shaft and/or provide feedback to a user, at 807. Examples of such adjustments and/or feedback are provided above with reference to FIGS. 5-7. In some embodiments, the muscle management device (or compute device of the muscle management device) can optionally receive inputs from a user, at 806, which can also cause the muscle management device to adjust the signal waveform and/or provide feedback to the user.

In some embodiments, one or more of 801-807 can repeat, e.g., such that further adjustments to waveforms based on sensor data and/or user inputs can be made, until a user is finish with using the device. In some embodiments, the control unit can monitor the usage of the muscle management device and, based on such monitoring, provide recommendations to the user as to when to move the muscle management device to a new location (e.g., over a new area of skin and/or muscle) and/or discontinue using the muscle management device. In some embodiments, the control unit can send information regarding muscle management device usage and/or monitored conditions (e.g., muscle conditions and/or other physiological parameters of a user) to other compute devices, e.g., via a network, as described above with reference to I/O device 156.

FIGS. 12-15 show a measurement device or scanner 1200 according to an embodiment. The measurement device 1200 can be configured to measure and/or determine a characteristic, state, or condition of a tissue or muscle of a user. The measurement device 1200 can include components that are structurally and/or functionally similar to components of other devices described herein, including the muscle management device 100 and/or the measurement device 1000, described above with reference to FIGS. 1 and 10, respectively. For example, the measurement device 1200 can include a housing 1210, a power source 1220, a driving mechanism 1230, an output mechanism 1240, one or more sensor(s) including a sensor 1242A, a control unit 1250, and a fixed shroud 1270A. Thus, portions and/or components of the measurement device 1200 may not be described again in detail herein.

Figure 12:
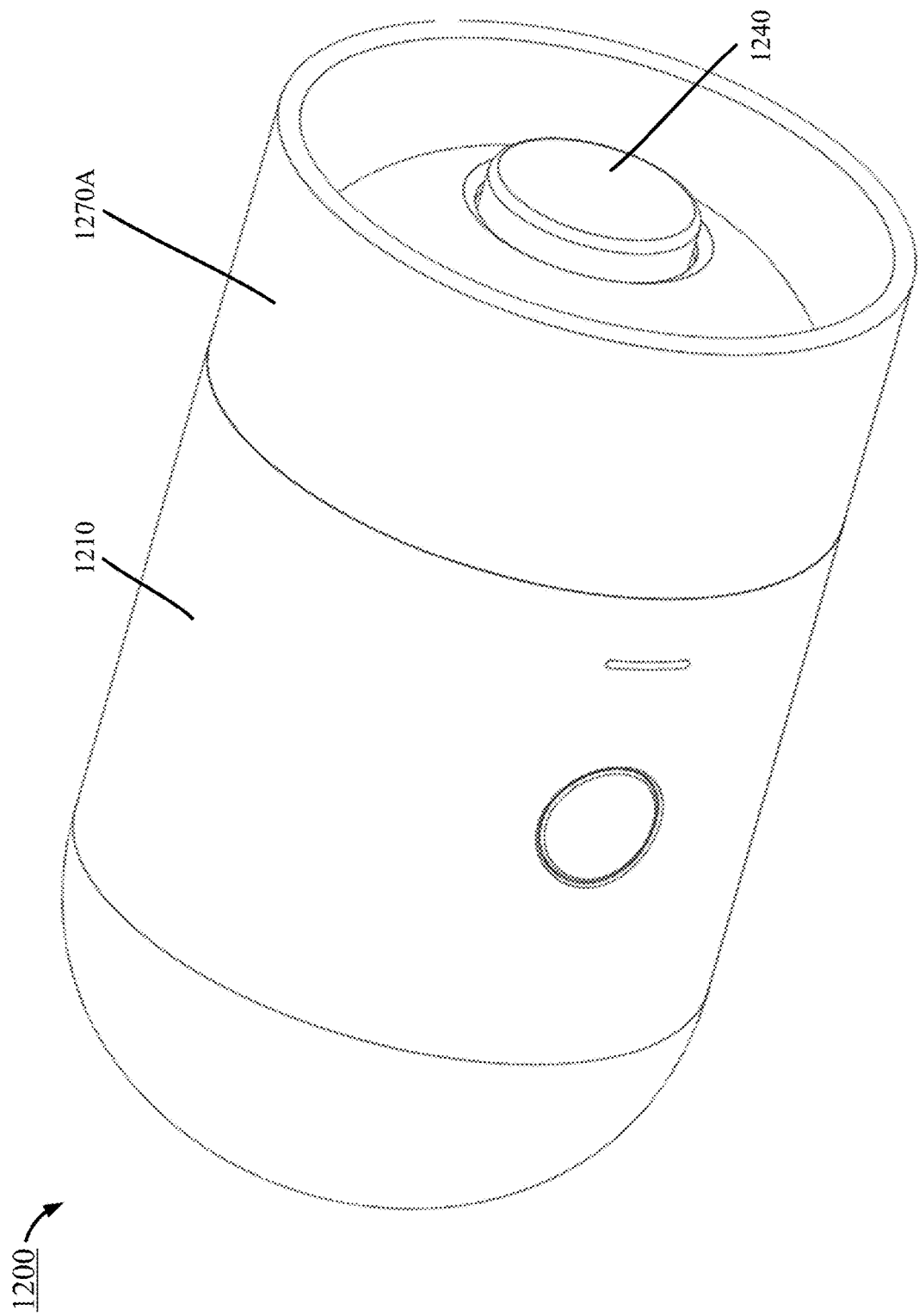
FIG. 12 is a perspective view of a measurement device, according to an embodiment.

The housing 1210 can include a compartment or chamber configured to accommodate and/or contain various components of the measurement device 1200 such as the power source 1220, the driving mechanism 1230, the one or more sensor(s) including sensor 1242A, and the control unit 1250. The housing 1210 can also be configured to contain a proximal portion of the output mechanism 1240, providing an opening that allows the output mechanism 1240 (or an end effector or head of the output mechanism 1240) to extend out of the housing 1210, as shown in FIG.12. The housing 1210 can have any suitable shape or configuration for housing and/or supporting the one or more components of the muscle management device 1200 and/or facilitating manipulation by a user. For example, as shown in FIG. 12, the housing 1210 can be an elongate structure having a circular cross-sectional shape, and a rounded rear-end configured to increase ergonomics of the measurement device 1200 such that a user may be able to manipulate the measurement device 1200 with one hand (i.e., single-handed use), e.g., to grasp and position the measurement device 1200 against a portion of tissue using a single hand.

The power source 1220 can be substantially similar to the power source 120 and/or the power source 1020, described above with reference to FIGS. 1 and 10, respectively. For example, the power source 1220 can be any suitable energy source and/or energy storage device, including, but not limited to one or more rechargeable batteries. In some embodiments, the measurement device 1200 can include one or more ports (not shown) that enable connection between an external power source and one or more components of the muscle management device 1200. The external power source can be used to directly power the components of the measurement device 1200 and/or recharge the onboard power source 1220.

Figure 15:
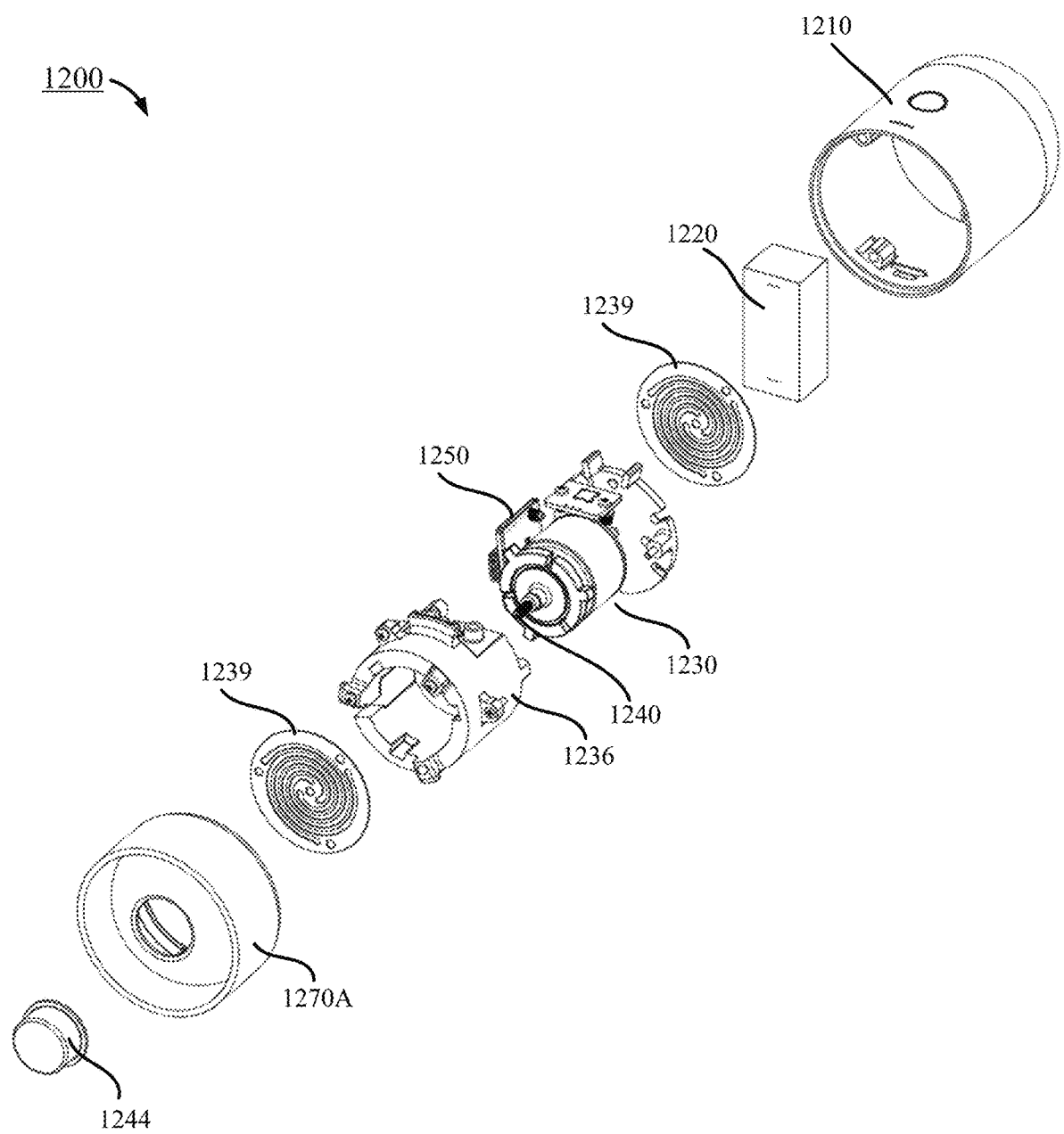
FIG. 15 is an exploded view of the measurement device of FIG. 12.

The control unit 1250 can be configured to activate and/or control the operation of one or more components of the measurement device 1200. In some embodiments the control unit 1250 can be coupled to the power source 1220 to establish and/or interrupt a flow of electric power (e.g., an electric current) to operate one or more components of the measurement device 1200. In some embodiments, the control unit 1250 can be coupled to a signal generator that can generate one or more current patterns or waveforms, which can be used to drive movement of the driving mechanism 1230. The control unit 1250 can also be coupled to the sensor(s) of the measurement device 1200, e.g., to receive sensor data from the sensor(s) and to process and/or analysis such sensor data, as further described herein. While not depicted in FIG. 12, the control unit 1250 can include a memory, a processor, and/or an I/O device, similar to the control unit 150 as depicted and described with reference to FIG. 1. Furthermore, in some embodiments the control unit 1250 can be or form part of an integrated circuit. For example, as shown in FIG. 15, the control unit 1250 can be an integrated chip 1250 disposed inside the housing 1210 and configured to integrate multiple components including the memory, the processor, and the I/O device. The integrated circuit 1250 can also include one or more other components of the system, including, for example, the signal generator.

In some embodiments, the control unit 1250 can be configured to receive and store instructions from an external device such as a user device, a back-end compute device, and/or a third-party device, as further described above with reference to FIG. 11. In some embodiments, the control unit 1250 can have stored instruction (e.g., in an onboard memory) that when executed by a processor (e.g., an onboard processor) can cause the processor to perform one or more operations associated with measuring one or more properties of various components of the measurement device 1200. Based on the received and/or stored instructions, the control unit 1250 can generate signals to control one or more components of the measurement device 1200. For example, the control unit 1250 can cause the signal generator to generate signals (e.g., waveforms) for activating movement of the output mechanism 1240, to adjust one or more parameters of the signals (e.g., waveform shape, frequency, amplitude, etc.), and/or to receive, process, analyze, and/or store, sensor data (e.g., data received from the sensor(s) of the measurement device 1200).

Figure 13:
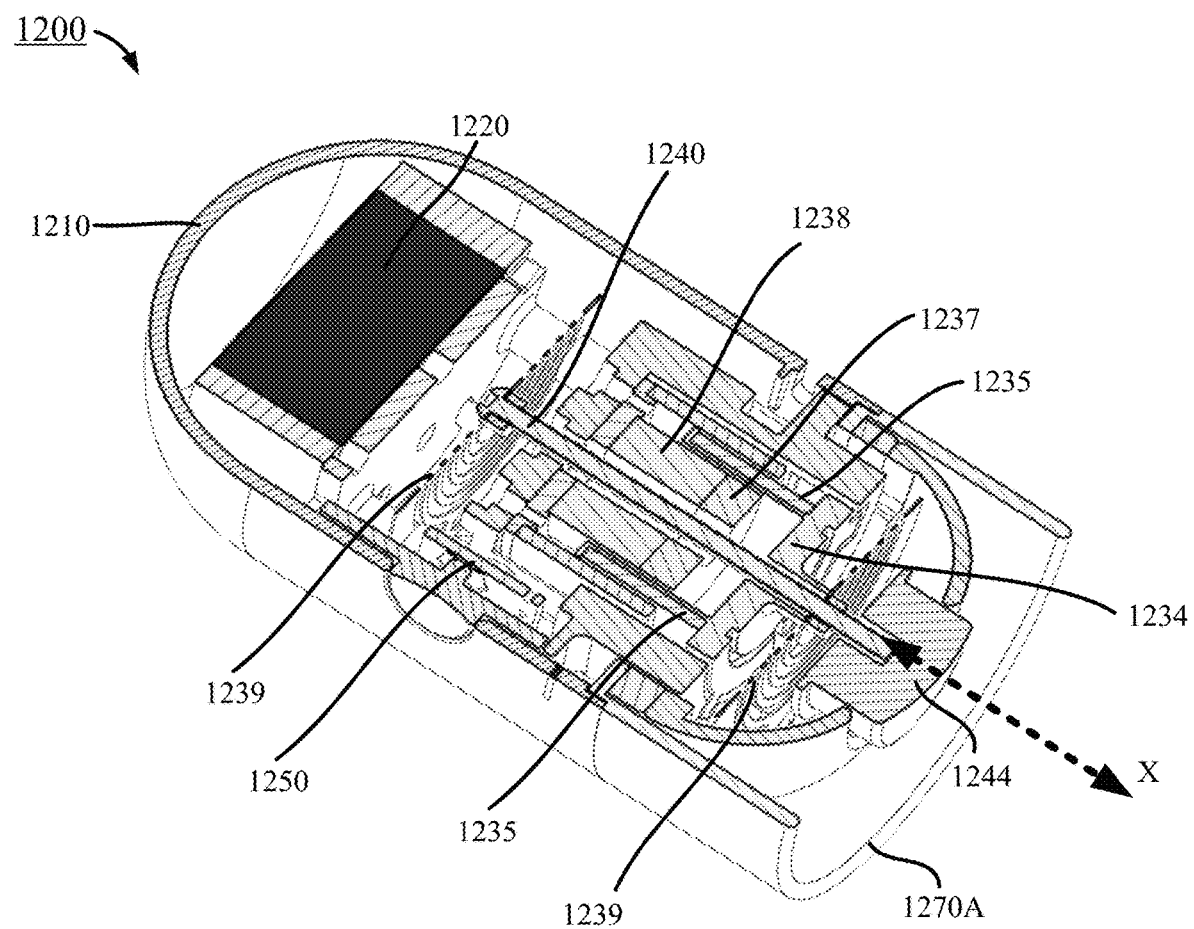
FIG. 13 is an angled cross-sectional view of the measurement device of FIG. 12.
Figure 14:
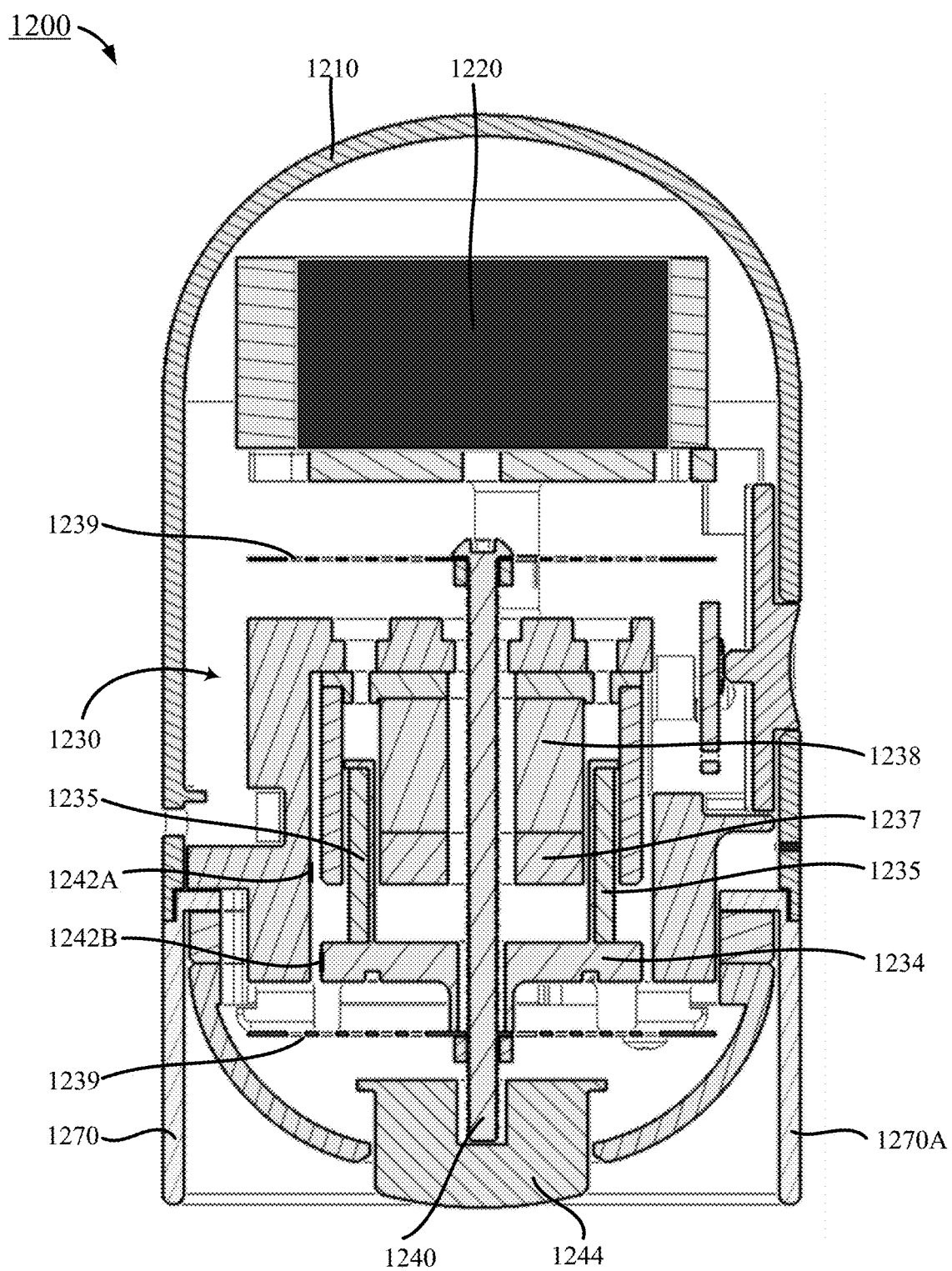
FIG. 14 is a cross-sectional view of the measurement device of FIG. 12.

The driving mechanism 1230 of the measurement device 1200 can be configured to drive movement of the output mechanism 1240 such that the output mechanism 1240 produces a mechanical output that can be applied to tissue. As shown in FIGS. 13 and 14, the driving mechanism 1230 can include a Lorentz force motor (e.g., a linear Lorentz force or voice-coil motor). The Lorentz force motor includes a magnet 1238 and a coil 1235 coupled to a bobbin 1234 to convert electrical energy to mechanical energy according to the Lorentz force principle. The bobbin 1234 can be coupled to the output mechanism 1240, and therefore movement of the coil and bobbin 1234 can be used to drive movement of the output mechanism 1240. In some embodiments the Lorentz force motor can also include a flux guide 1237 configured to reduce stray magnetic flux. The flux guide 1237 can be, for example, an end plate that is attached to the magnet 1238, similar to the flux guide 337 described above with reference to FIG. 3. In some embodiments, the driving mechanism 1230 can be disposed within an enclosure 1236 configured to provide mechanical support to the components of the driving mechanism 1236. In some embodiments, the enclosure 1236 can be configured to couple one or more components of the measurement device 1200 such as, for example, the control unit 1250.

The driving mechanism 1230 can be configured to receive an electrical signal (e.g., an electric current) from the signal generator of the control unit 1250, and to generate mechanical movement along an axis X of the muscle management device 1200 (e.g., a longitudinal axis of the measurement device 1200, as shown in FIG. 13). The mechanical movement can cause the output mechanism 1240 to produce an output signal (e.g., by moving back-and-forth or in an oscillatory or vibratory manner) that can be applied to a user to measure a characteristic of a tissue and/or muscle. In some instances, the driving mechanism 1230 can produce the output signal for a predetermined period of time of between about 2 seconds and about 5 minutes, including all values and subranges therebetween. Sensor 1242A, further described below, can be configured to measure a property associated with the driving mechanism 1230 during the predetermined period of time that the driving mechanism 1230 is producing and applying the output signal to the tissue and/or muscle.

The measurement device 1200 can be configured to reduce or minimize factors (e.g., including friction, off-axis movement, etc.) that can affect the mechanical movement of the output mechanism 1240, which can be implemented as or include a shaft that extends parallel to a longitudinal axis of the measurement device 1200. For example, in some embodiments the measurement device 1200 can include one or more spiral flexures 1239 configured to minimize or reduce off-axis movement of the output mechanism 1240, e.g., movement not along a longitudinal axis of the measurement device 1200 or an X-axis (as depicted in FIG. 13). The spiral flexures 1239, as positioned and configured, can have high stiffness in directions off-axis from the longitudinal axis or X-axis and low stiffness in a direction along the longitudinal axis or X-axis. Accordingly, the spiral flexures 1239 can be configured to efficiently drive the output mechanism 1240 along the X-axis but reduce or prevent movement of the output mechanism 1240 in directions lateral to or offset from the X-axis. In some embodiments, a plurality of spiral flexures 1239 can be disposed inside the housing 1210 at spaced locations along a length of the output mechanism 1240. For example, a first spiral flexure 1239 can be positioned near a proximal end of the output mechanism 1240 and a second spiral flexure 1239 can be positioned near a distal end of the output mechanism 1240, with the two flexures 1239 together being appropriately positioned to guide the movement of the output mechanism 1240, as shown in FIGS. 13-15.

The output mechanism 1240 can be substantially similar to the output mechanism 140 and 1040, described above with reference to FIGS. 1 and 10, respectively. For example, in some embodiments the output mechanism 1240 of the measurement device 1200 can be configured to transfer the mechanical energy generated by the measurement device 1200 to a target area (e.g., skin and/or muscle area) of a user. The output mechanism 1240 can include a shaft 1240 and a delivery interface or end effector 1244 coupled to one end of the shaft 1240, as shown in FIG. 13. The delivery interface 1244 can be configured to contact the skin and/or muscle of a user, e.g., at the target area. The delivery interface 1244 can be any suitable shape or form. For example, in some embodiments the delivery interface can be a disk-like shape characterized by a diameter and a thickness, as shown in FIG. 15. In some embodiments, the delivery interface 1244 can include a surface with rounded edges configured to to improve ergonomics when the delivery interface 1244 is in contact with the skin and/or muscle of a user at the target area. The delivery interface 1244 can be coupled to the shaft 1240 via one or more coupling mechanisms including, but not limited to threaded ends, screws, bolt fasteners, welding, brazing, adhesives, or any combination thereof.

The output mechanism 1240 can be operatively coupled to the driving mechanism 1230 and be configured to move in response to movement generated by the driving mechanism 1230. The output mechanism 1240 and/or the delivery interface 1244 can move in and out of the housing 1210, in response to the mechanical movement of the driving mechanism 1230. At least a portion of the output mechanism 1240 can be disposed inside the housing 1210 and can be coupled with at least a portion of the driving mechanism 1230, such as, for example, the bobbin 1234 (as shown in FIGS. 13 and 14). The coupling between the output mechanism 1240 and the portion of the driving mechanism 1230 can facilitate conduction or transfer of mechanical movements (e.g., highly sensitive mechanical dynamics) from the driving mechanism 1230 to the shaft 1240.

The sensor 1242A can be configured to measure and/or record information associated with the output mechanism 1240 of the measurement device 1200. The sensor 1242A can be configured to measure and/or record a position of the output mechanism 1240, and/or an acceleration of the output mechanism 1240. The sensor 1242A can include a position sensor configured to detect the position of the shaft 1240. The position sensor may indicate absolute position (location) or relative position (displacement), in terms of linear travel, e.g., along a direction of the axis X. In some embodiments, the position sensor can be a capacitive displacement sensor that measure variations of capacitance between two points: a first point comprising a sensor 1242A and a second point comprising a conductive target 1242B, as shown in FIG. 14. Alternatively, in some embodiments the position sensor can be an inductive sensor that uses a coil and an oscillator to create a magnetic field in the close surroundings of the sensing surface and produce a dampening of the oscillation amplitude in response to the position of an actuator. In some embodiments, the position sensor can be an optical component such as a laser doppler vibrometer that directs a laser beam at surface of interest, and the vibration amplitude and frequency are extracted by the doppler shift of the of a reflected laser beam frequency due to the motion of the surface. In some embodiments, other types of sensors can be used, including, for example, an accelerometer configured to measure an acceleration profile of the output mechanism 1240. The accelerometer can be disposed on a shaft 1240 of the output mechanism 1240 and/or on a delivery interface 1244 of the output mechanism 1240. In some embodiments, the position, acceleration, and/or force data measured by one or more sensor can be used to calculate one or more characteristics of a tissue and/or muscle of a user, such as a stiffness, damping, and/or mass of a muscle.

The fixed shroud 1270A can be used as a reference for how deep or how much to press the output mechanism 1240 against a surface of the user's skin. The fixed shroud 1270A can serve as a reference for the user, e.g., to prevent the user from pressing the output mechanism 1240 against the skin too lightly or too hard. As described above with respect to the measurement device 1000 in FIG. 10, being able to account for depth or position of the output mechanism 1240 relative to the tissue and/or muscle can avoid user-induced biases into the measurements of the tissue and/or muscle properties. By providing a reference frame for how much to press the output mechanism 1240 against tissue, a user may be able to maintain the measurement device 1200 against the tissue at a constant or substantially constant depth or position over a longer period of time. Such can therefore enable the measurement device 1200 to be used for longer periods of time, e.g., to measure data associated with the output mechanism 1240 for a longer period of time and thus determine a characteristic of the tissue and/or muscle for a longer period of time. The fixed shroud 1270A can be coupled to and/or integrated with the housing 1210 and can be configured to remain stationary while the output mechanism 1240 is configured to move about the axis X. The fixed shroud 1270A can be any suitable mechanical structure coupled to the housing 1210 and configured to make contact with a surface of the user's skin and prevent undesired changes in the orientation and/or position of the measurement device 1200 against the skin of the user while the output mechanism 1240 is configured to move about the axis X. As shown in FIG. 12, the shroud 1270A can be an annular wall or structure (e.g., a tubular wall, elliptical wall, etc.) that surrounds or partially surround the output mechanism 1240 and provides a surface that can be placed in direct contact with the user's skin at a target area and/or region over which a tissue and/or muscle to be measured is located.

FIGS. 16A-19 show portions of a measurement device or scanner 1600, according to an embodiment. The measurement device 1600 can be configured to measure and/or determine the state or condition of a tissue or muscle of a user. The measurement device 1600 can include components that are structurally and/or functionally similar to components of other devices described herein, including the muscle management device 100 and the measurement devices 1000 and 1200, described above with reference to FIGS. 1, 10, and 12-15. For example, the measurement device 1600 includes a driving mechanism 1630, an output mechanism 1640, and sensor 1642A. Thus, portions and/or components may not be described again in detail herein.

Unlike the measurement device 1200, the measurement device 1600 can include a moving shroud 1670B (in addition to or without a fixed shroud). The measurement device 1600 can also include a sensor 1632A that is configured to measure a property associated with the moving shroud 1670B, as further described below. FIGS. 16A, 16B, 17A, 17B, and 19 each depict the measurement device 1600 without an outer housing, so as to facilitate viewing of internal components of the measurement device 1600. It can be appreciated though that measurement device can include an outer housing and/or a fixed shroud that is coupled that that outer housing.

The driving mechanism 1630 of the measurement device 1600 can be substantially similar to the driving mechanism 1230 of the measurement device 1200 described above with reference to FIGS. 12-15. For example, the driving mechanism 1630 can be configured to drive movement of the output mechanism 1640 such that the output mechanism 1640 produces a mechanical output. The driving mechanism 1630 can include a Lorentz force motor (e.g., a linear Lorentz force or voice-coil motor) which includes a magnet 1638, and a coil 1635 (e.g., a conductor disposed around a bobbin 1634) to convert electrical energy to mechanical energy according to the Lorentz force principle. The Lorentz force motor can also include a flux guide 1637 configured to reduce stray magnetic flux. The flux guide 1637 can be an end plate that is attached to the magnet 1638, as shown in the cross-sectional view of the driving mechanism 1630 shown in FIGS. 17A and 17B. In some embodiments the driving mechanism 1630 can be configured to receive an electrical signal (e.g., an electric current) from a signal generator of the measurement device 1600 and to generate mechanical movement along an axis X (e.g., a longitudinal axis of the measurement device 1600). The mechanical movement can cause the output mechanism 1640 to produce an output signal (e.g., by moving back-and-forth or in an oscillatory or vibratory manner) that can be applied to a user.

Figure 16B:
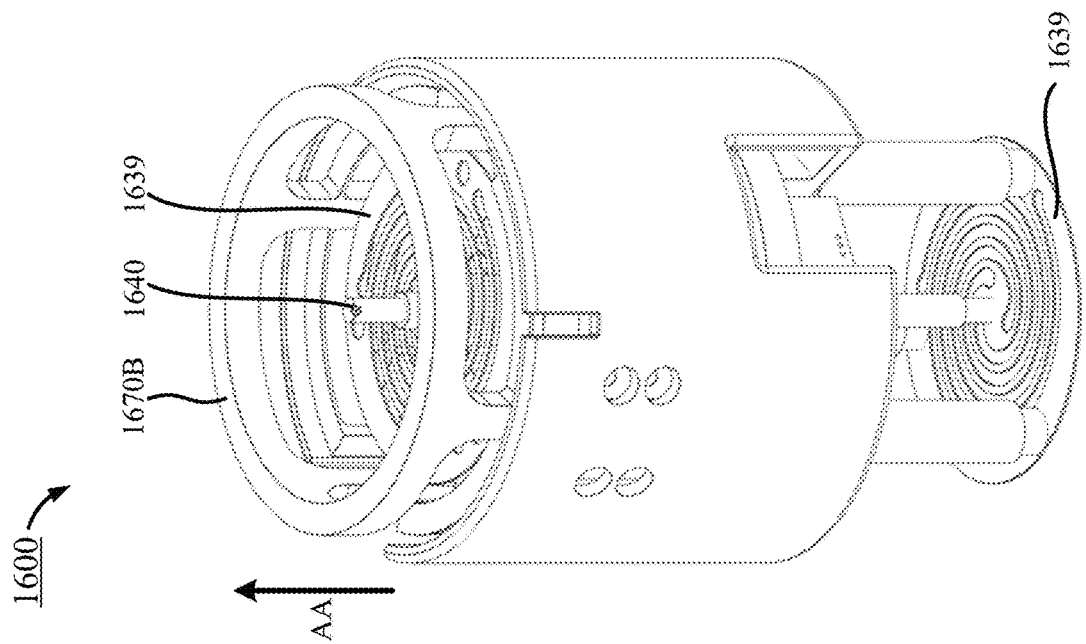
FIGS. 16A and 16B are perspective views of a portion of a measurement device, displaying a moving shroud in a retracted position and an extended position, respectively, according to embodiments.
Figure 16A:
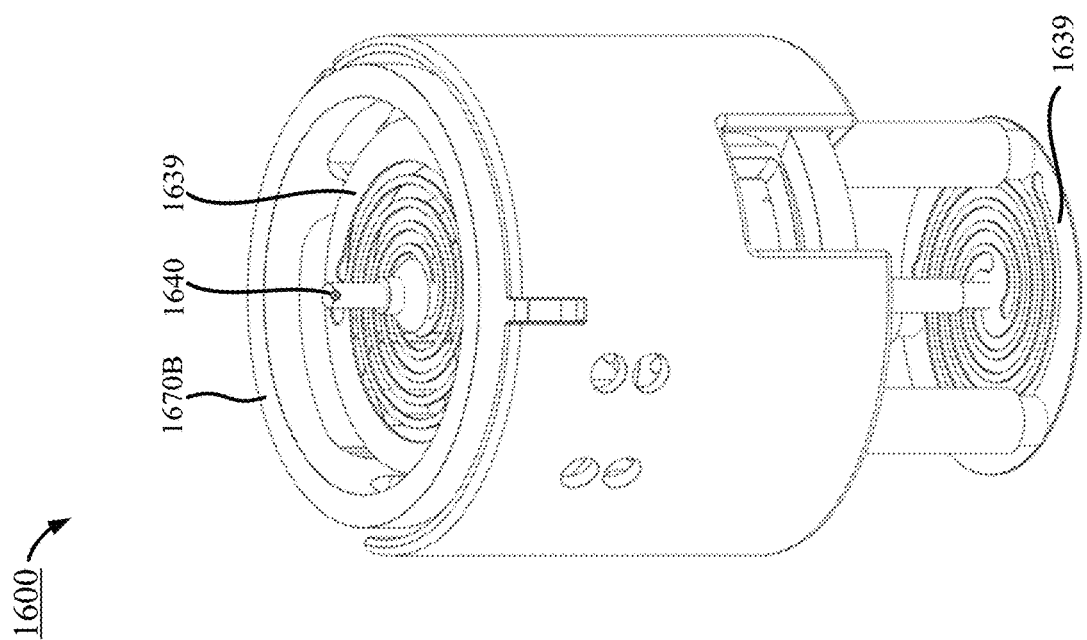

In some embodiments, the measurement device 1600 can be configured to reduce or minimize factors (e.g., including friction, off-axis movement, etc.) that can affect the mechanical movement of the output mechanism 1640. For example, in some embodiments the measurement device 1600 can include one or more flexures 1639 configured to minimize or reduce off-axis movement of the output mechanism 1640 (e.g., movement not along a longitudinal axis of the output mechanism 1640). The flexures 1639 can be structurally and/or functionally similar to the flexures 1239 described with reference to device 1200. The flexures 1639, as positioned and configured, can have high off-axis stiffness and low in-line or on-axis stiffness. Accordingly, the flexures 1639 can be configured to efficiently drive the output mechanism 1640 along its longitudinal axis but reduce or prevent movement of the output mechanism 1640 in directions lateral to or offset from the longitudinal axis. In some embodiments, such components can be mechanically coupled the output mechanism 1640 (or a shaft of the output mechanism 1640) which is configured to transfer the mechanical energy generated by the measurement device 1600 via a delivery interface or end effector to a target area of a user. For example, FIGS. 16A and 16B show a perspective view of the driving mechanism 1630 displaying two flexures 1639 coupled to the output mechanism 1640 at two points along the length of the output mechanism 1640 and appropriately positioned to guide the movement of the output mechanism 1640.

Figure 18:
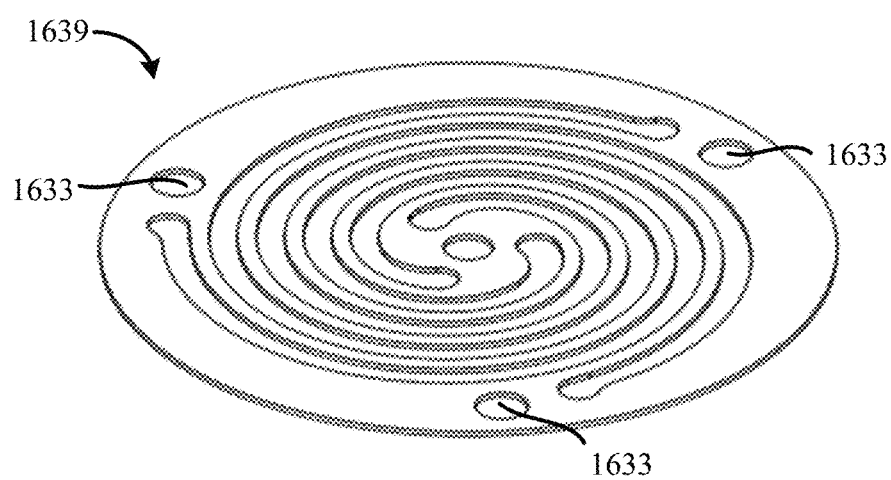
FIG. 18 is a perspective view of a flexure included in the measurement device of FIGS. 16A and 16B.
Figure 19:
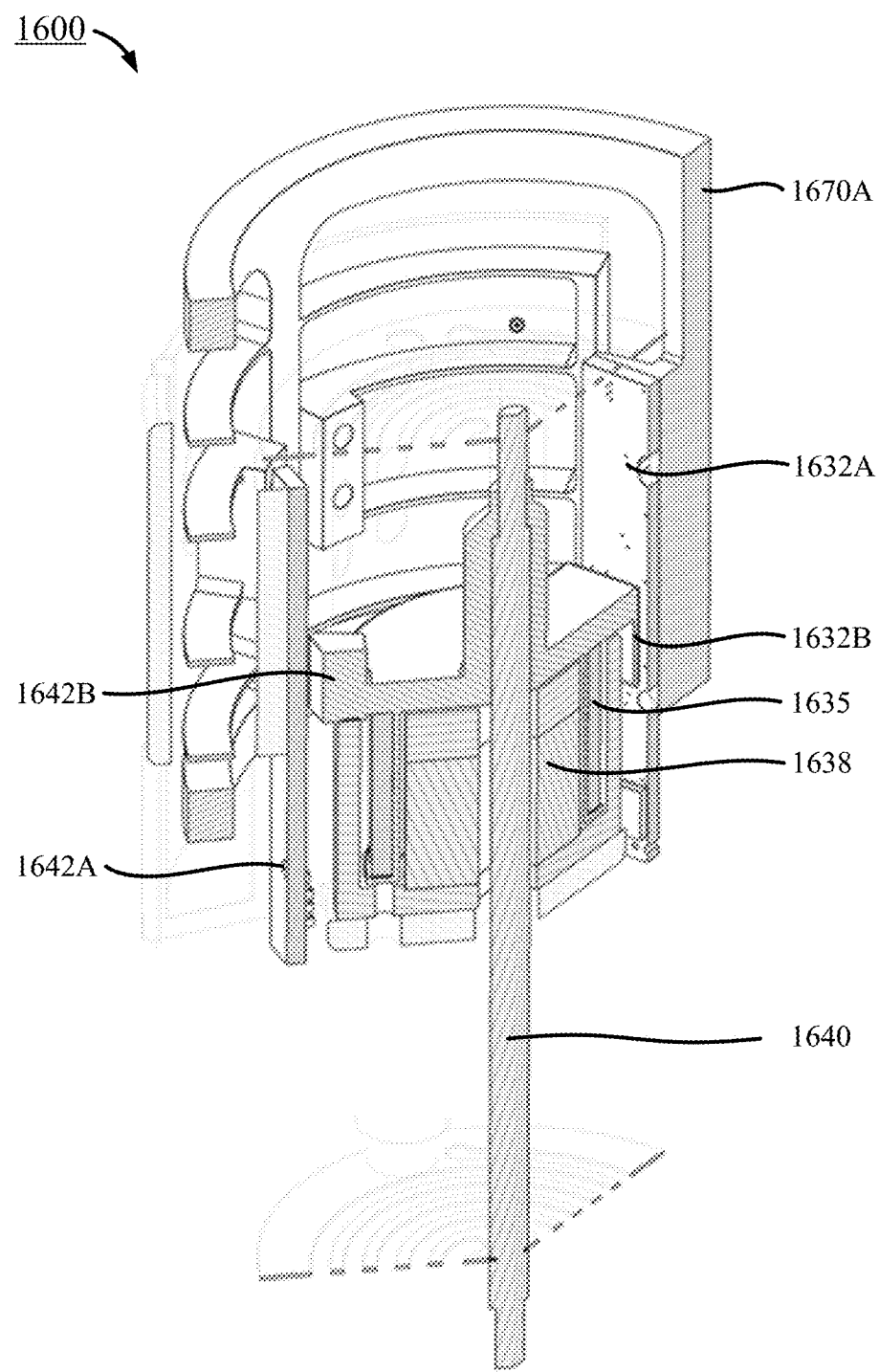
FIG. 19 is a sectional view of a portion of the measurement device of FIGS. 16A and 16B, displaying the location of a position sensor coupled to an output mechanism and a position sensor coupled to a moving shroud.

The flexures 1639 can be any suitable structure configured to have high off-axis stiffness and low in-line or on-axis stiffness. In some embodiments, the flexures 1639 can be a planar structure having a suitable cross-sectional shape including, but not limited to a circular, elliptical, and/or polygonal shape. In some embodiments, the flexures 1639 can include a plurality of openings and/or channels forming a pattern that reduces in-line or on-axis stiffness while maintaining off axis stiffness. For example, FIG. 18 shows a perspective view of a flexure 1639, which includes a spiral cutout pattern that reduces in-line or on-axis stiffness but maintains off axis stiffness. The flexure 1638 can include three holes 1633 for coupling the flexure 1638 to other fixed portions of the measurement device 1600. As such, the flexure 1638 can be held in place axially by the coupling points while its center can deform to allow on-axis or in-line deformation with low friction.

The output mechanism 1640 can be substantially similar to the output mechanisms 1040 and 1240 described above with reference to FIG. 10 and FIGS. 12-15, respectively. For example, the output mechanism 1640 of the measurement device 1600 can be configured to transfer the mechanical energy generated by the measurement device 1600 to a target area (e.g., skin and/or muscle area) of a user. The output mechanism 1640 can include a shaft 1640 as well as a delivery interface (not shown) that is configured to contact the skin and/or muscle of the user, e.g., at the target area. The output mechanism 1640 can be operatively coupled to the driving mechanism 1630 and be configured to move in response to movement generated by the driving mechanism 1630.

One or more sensors can be configured to measure and/or record information associated with the output mechanism 1640 of the measurement device 1600. In some embodiments, the sensor(s) can be configured to measure and/or record a position of the output mechanism 1640, an acceleration of the output mechanism 1640, or other data associated with the output mechanism 1640. In particular, the sensor(s) can include a position sensor 1642A configured to detect the position of the output mechanism or shaft 1640. The position sensor 1642A may indicate absolute position (location) or relative position (displacement), in terms of linear travel, e.g., along a direction of the longitudinal axis of the shaft 1640. In some embodiments, the position sensor 1642A can be a capacitive displacement sensor that measures variations of capacitance between two points: a first point comprising the sensor 1642A and a second point comprising a conductive target 1642B, as shown in the sectional view of FIG. 19. Alternatively, in some embodiments a position sensor can be an inductive sensor that uses a coil and an oscillator to create a magnetic field in the close surroundings of the sensing surface and produce a dampening of the oscillation amplitude in response to the position of an actuator. In other embodiments, a position sensor can be an optical component such as a laser doppler vibrometer that directs a laser beam at surface of interest, and the vibration amplitude and frequency are extracted by the doppler shift of the of a reflected laser beam frequency due to the motion of the surface. In some embodiments, the sensor(s) can include an accelerometer configured to measure an acceleration profile of the output mechanism 1640. The accelerometer can be disposed on the shaft 1640 and/or on a delivery interface 1644 of the output mechanism 1640. In some embodiments, the position, acceleration, and/or force data measured by the sensor(s) can be used to calculate one or more characteristics of a tissue and/or muscle of a user, such as a stiffness, damping, and/or mass of a muscle.

One or more sensors can be configured to measure and/or record information associated with the shroud 1670B. The sensor(s) can be operatively coupled to the moving shroud 1670B and to a control unit of the measurement device 1600. In some embodiments, the sensor(s) can include a position sensor 1632A configured to detect the position of the moving shroud 1070B. The position sensor 1632A may indicate absolute position (location) or relative position (displacement), in terms of linear travel, e.g., along a direction of the longitudinal axis. In some embodiments, the control unit of the measurement device 1600 (or a processor, such as a processor associated with a user device 1180, a back-end compute device 1190, and/or a third-party device 1185, as described with reference to FIG. 11) can receive data representative of the position (location) of the moving shroud 1670B from the sensor 1632A and use that data to process and/or analyze data representative of the position (location) of the output mechanism 1640 (e.g., received from the sensor(s) 1642). For example, the moving shroud 1670B can provide a depth reference for measurements of muscle stiffness. The moving shroud 1670B can be configured to move (e.g., retract into the housing 1610 along the longitudinal axis) as a user presses the measurement device 1600 against a surface of the user's skin. As such, the movement or displacement of the moving shroud 1670B can be indicative of a measure of depth or position of the measurement device 1600 relative to the user's muscle.

Figure 17A:
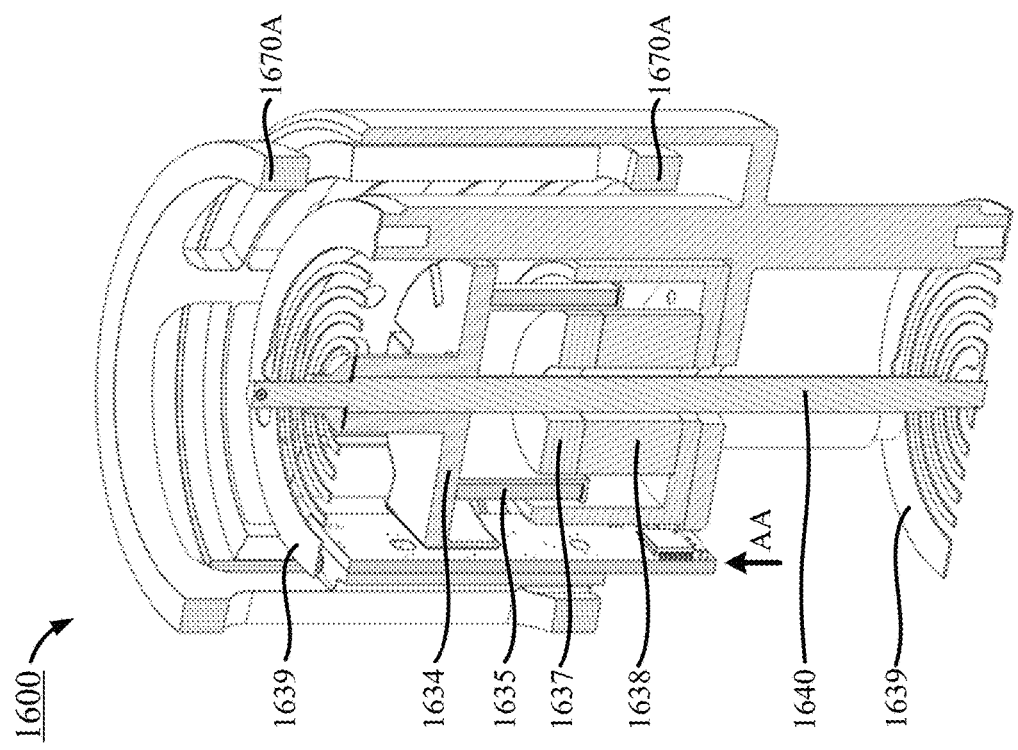
FIGS. 17A and 17B are cross-sectional views of a portion of the measurement device of FIGS. 16A and 16B, displaying a moving shroud in a retracted position and an extended position, respectively.

FIGS. 16A and 17A show the shroud 1670B disposed on a retracted position (e.g., a fully retracted) position. In the retracted position, the moving shroud 1670B can be retracted a distance that corresponds to a first position or depth that the output mechanism 1640 is at with respect to the target tissue and/or muscle. In the retracted position, a surface of the moving shroud 1670B is in contact with the user's skin and exerts a first degree of pressure or force against the skin.

Figure 17B:
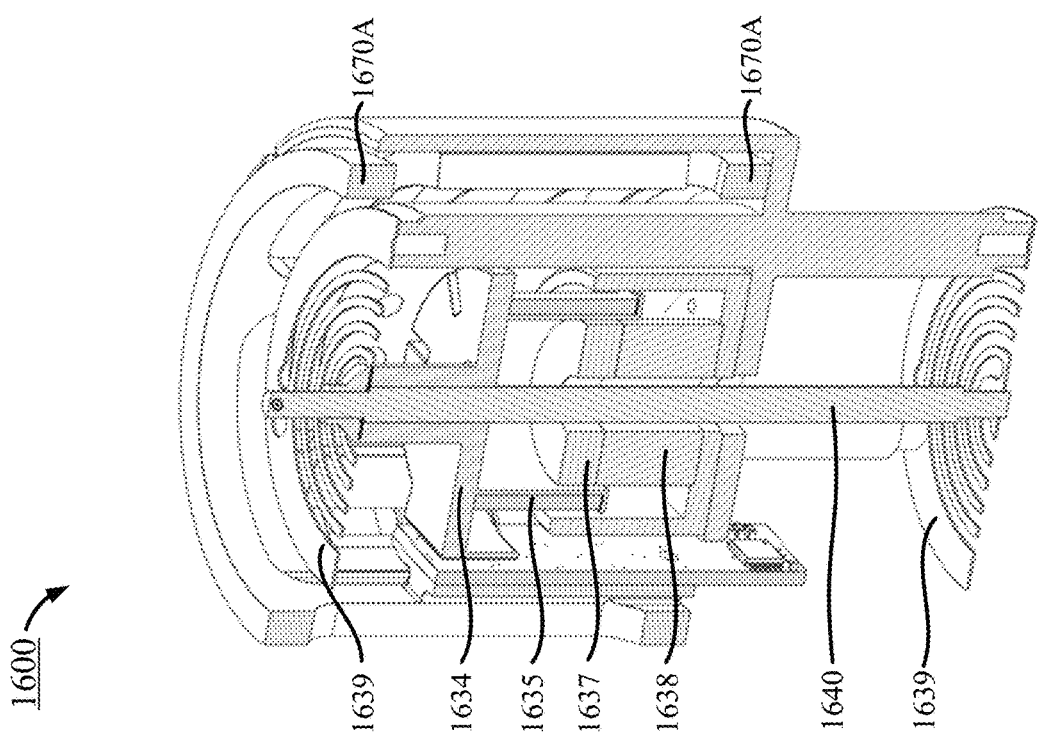

FIGS. 16B and 17B show the shroud 1670B disposed in an extended position (e.g., a fully extended position). In the extended position, the moving shroud 1670B can be extended relative to its retracted position depicted in FIGS. 16A and 17A. The moving shroud 1670 can be transitioned from the retracted position (shown in FIGS. 16A and 17A) to the extended position (shown in FIGS. 16B and 17B) by reducing the pressure applied by the measurement device 1600 against the user's skin such that the moving shroud 1670B moves along the direction AA shown in FIGS. 16B and 17B. In the extended position, the moving shroud 1670B can be at a position that corresponds to a second position or depth that the output mechanism 1640 is at with respect to the target tissue and/or muscle. In the extended position, a surface of the moving shroud 1670B can be in contact with the user's skin and can exert a second degree of pressure or force against the skin. The second degree of pressure or force can be less than the first degree of pressure or force, as described above. In some embodiments, in the extended position, the surface of the moving shroud 1670B may exert substantially no pressure against a surface of the user's skin.

The sensor 1632A can be configured to measure the displacement of the moving shroud 1670B, e.g., by tracking a position of the moving shroud 1670B when the measurement device 1600 is placed against a surface of the user's skin between the retracted position (or fully retracted position) and the extended position (or fully extended position). This depth information can provide greater dimensionality of data regarding muscle stiffness, when used in conjunction with the sensor 1642A. As described above, the sensor 1642A can measure a position associated with the output mechanism 1640. Such data can be used to determine or evaluate one or more characteristics of a user's muscle, such as, for example, muscle stiffness. Accordingly, when used in conjunction with a moving shroud 1670B and sensor 1632A, output mechanism 1640 and sensor 1642A can be used to provide richer information regarding muscle stiffness, including for example, stiffness as a function of depth or position (e.g., a depth or position of the output mechanism 1640 relative to the tissue). In some embodiments, by being able to account for position or depth, the measurement device 1600 can additionally or alternatively provide data that can be used to determine damping of the muscle over time, as well as data of other parameters that may vary over time.

Figure 24:
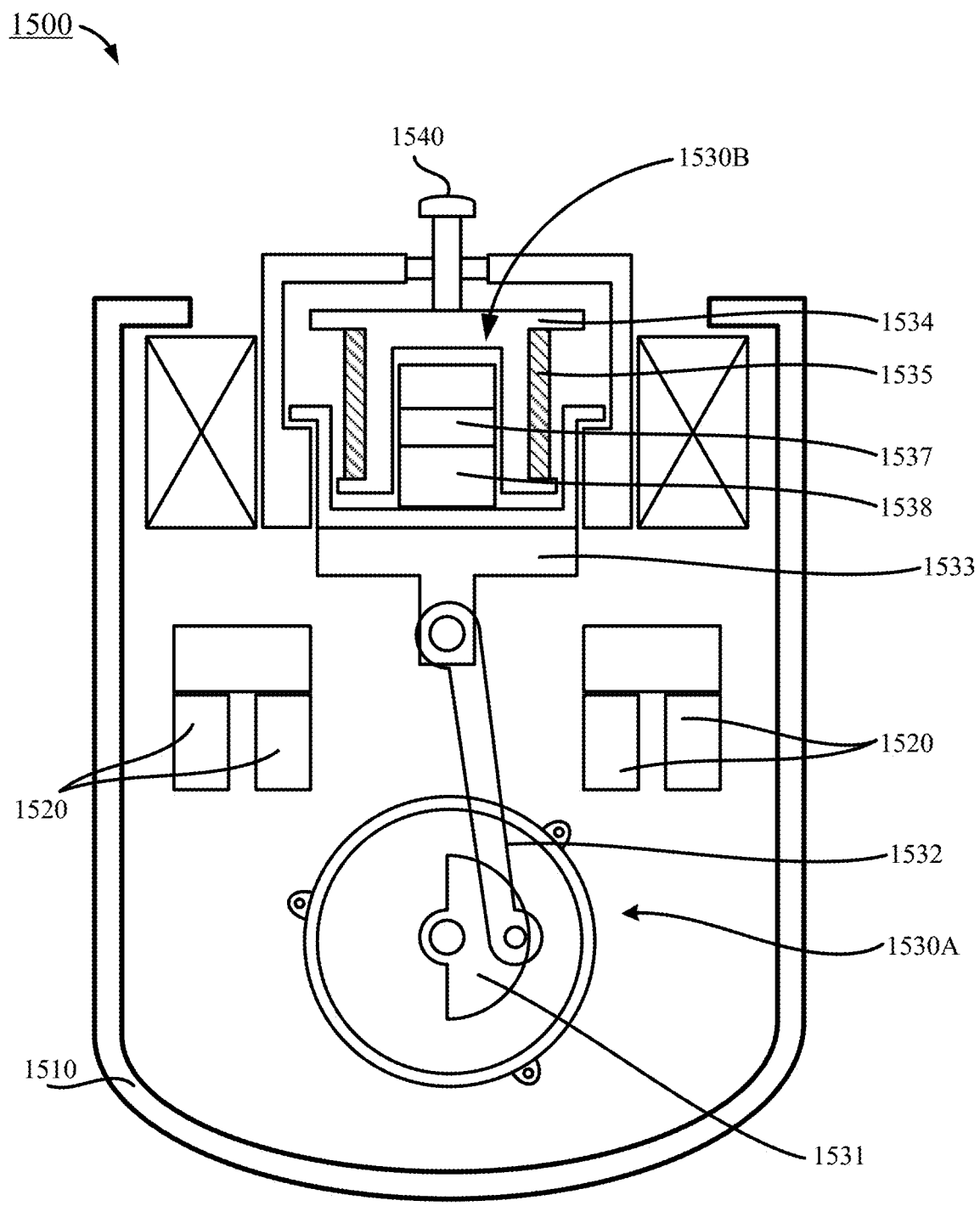
FIG. 24 is a schematic illustration of a muscle management device, according to an embodiment.

FIG. 24 depicts an example device 1500, according to embodiments. Device 1500 can be a muscle management device or measurement device, and can include components that are structurally and/or functionally similar to other muscle management devices, measurement devices, or treatment devices described herein. For example, device 1500 can include a driving mechanism implemented as or including a first actuator 1530A and a second actuator 1530B, an output mechanism 1540, a power source 1520, and a housing 1510. Thus, certain details of such portions and/or components may not be described again herein.

Device 1500 can be suited for creating a broad selection of massage types. For example, different individuals may prefer different types of massage, depending on a region or area of focus or personal preferences. For larger muscles, such as the quadriceps or hamstrings, a user may prefer to have a high intensity massage, e.g., a massage that utilizes a large stroke length and/or relatively high force. For smaller muscles, such as muscles around the jaw or neck, a user may prefer to have a more gentle massage, e.g., a massage that utilizes a small stroke length, with a relatively low force. As such, a massage device such as device 1500 that can scale between different modes of massage can be desirable. Device 1500 can also provide a broader selection of massage types for treating different types of conditions associated with a muscle area, e.g., as reflected by measurements taken by a measurement device or scanner (or muscle management device equipped with muscle measurement capabilities).

Device 1500 can also be used as a muscle measurement device or scanner. In sports or other types of high exertion activities, injuries can occur as a result from overuse or inadequate preparation of muscles. The ability to accurately and quickly measure mechanical properties of muscles can aid in reducing a number and/or severity of overuse injuries. For sufficient insight to be gained from such measurements, the measurements of the muscle need to be performed to a degree that provides adequate resolution and bandwidth. The combination of requirements necessary to perform measurements and massaging can be difficult to achieve. For massaging or muscle treatment, a high displacement, high force actuator may be necessary. While for measurements, a high frequency actuator may be necessary. As such, a device such as device 1500 that is equipped with muscle measurement and treatment features may be required to have high displacement, high force, and high frequency capabilities. Device 1500 incorporates these functions by having two separate actuators 1530A, 1530B that together can achieve the displacement, force, and bandwidth requirements for muscle measurements and treatment.

As depicted in FIG. 24, device 1500 has an output mechanism 1540 that can be driven by a first actuator 1530A and a second actuator 1530B. Each actuator 1530A, 1530B can be controlled by a processor (or control unit) and a drive system or signal generator, where the processor can generate control signals for regulating energy delivery from the power source(s) 1520 to the drive systems and the actuators 1530A, 1530B. Device 1500, as depicted, includes multiple power sources 1520, but it can be appreciated that one or more power sources 1520 can be used to activate the drive systems and actuators 1530A, 1530B.

The first actuator 1530A can be structurally and/or functionally similar to the first actuator 931a as described with reference to FIG. 9. For example, the first actuator 1530A can be used to generate a high force, long stroke output. In an embodiment, the actuator can be an electric motor including a Lorentz force motor, a brushless DC motor, or brushed DC motor. The first actuator 1530A can be connected to mechanisms used to gain a mechanical advantage or convert rotary motion into linear motion, such as a crank-piston mechanism including a crank arm 1531, a connecting rod 1532, and a long stroke piston 1533.

The second actuator 1530B can be structurally and/or functionally similar to the second actuator 931b as described with reference to FIG. 9. For example, the second actuator 1530B can be used to generate a low-force, low displacement stroke, but at a high bandwidth. The second actuator 1530B can be connected directly to the first actuator 1530A, such that the actuators 1530A, 1530B are in series together. The combination of the two actuators 1530A, 1530B can achieve the desired outcome of a high-force, high-displacement, high-bandwidth muscle management device. The second actuator 1530B can be an electric motor, such as a Lorentz force motor, brushless DC motor, brushed DC motor, piezoelectric actuator, LRA, solenoid, or other type of motor. In the embodiment depicted in FIG. 24, the second actuator 1530B can be a Lorentz force motor, including a permanent magnet 1538, a flux guide 1537, a coil 1535, and a short stroke bobbin 1534. Such components can be substantially similar to other like components described with reference to earlier embodiments.

In some embodiments, actuators 1530A, 1530B can be controlled by independent drive systems or signal generators that can contain power electronics (e.g., MOSFETs, GaN-FETs, or power op-amps). These rive systems can take a reference signal as an input, and act as the power amplifiers for driving the actuators.

While the actuators 1530A, 1530B are depicted in FIG. 24 as being in series with each other, it can be appreciated that in other embodiments, the actuators 1530A, 1530B can be arranged in parallel with each other. For example, each actuator 1530A, 1530B can be arranged to independently drive the movement of the output mechanism 1540 without having to move a mass of one of the other actuators 1530A, 1530B. Such a configuration can result in higher bandwidth being capable with both actuators 1530A, 1530B.

While device 1500 is not depicted with one or more sensors, it can be appreciated that any number of sensors can be coupled to device 1500, including sensors that can measure one or more properties associated with the output mechanism 1540 and/or housing 1510 (e.g., sensor(s) 912, 942 as described with reference to FIG. 9). The sensors can include, for example, one or more of a position sensor, an accelerometer, a gyroscope, a pressure sensor, a force sensor, a current sensor, a orientation sensor, etc. The sensor(s) can be used for controlling the actuators 1530A, 1530B, generating commands associated with the actuators 1530A, 1530B, and/or providing data about the user.

Figure 20:
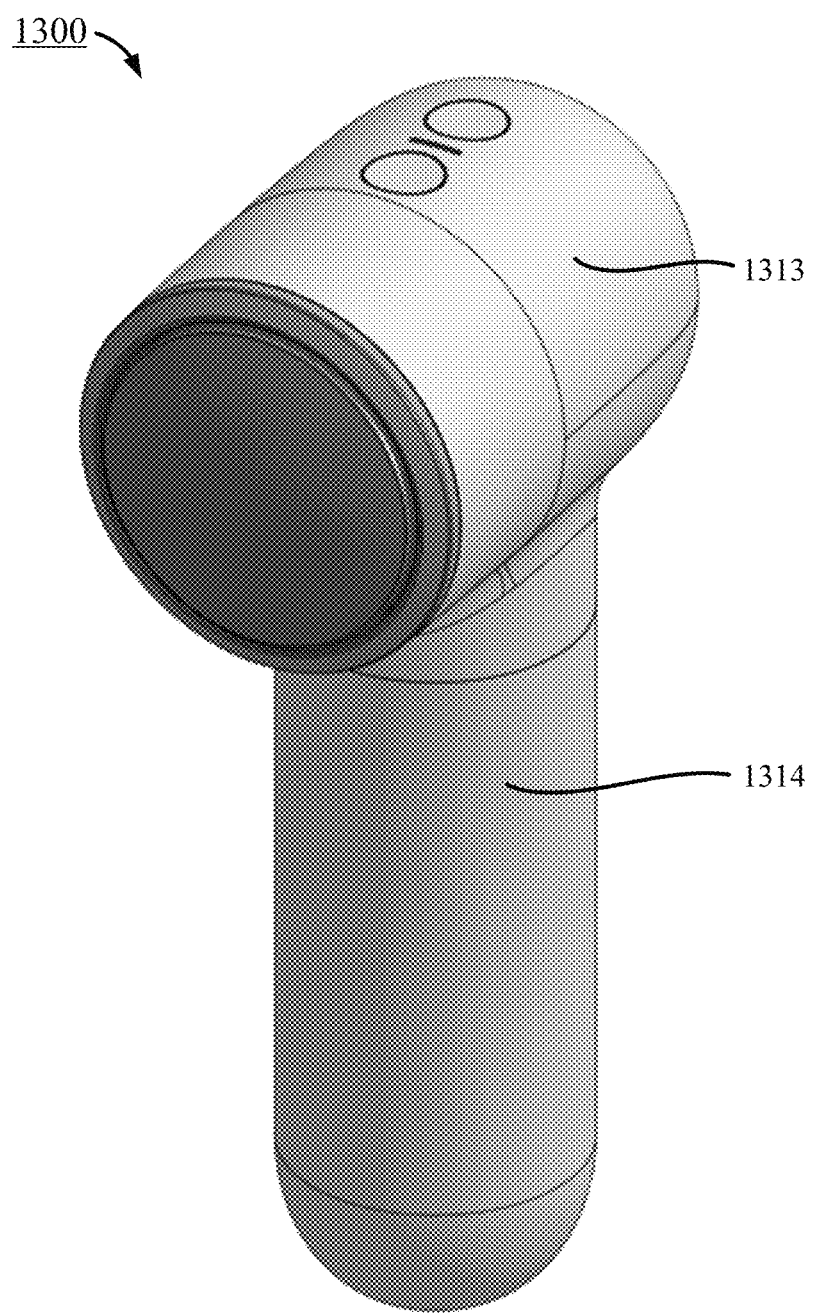
FIG. 20 is a perspective view of a massager device, according to embodiments.
Figure 21:
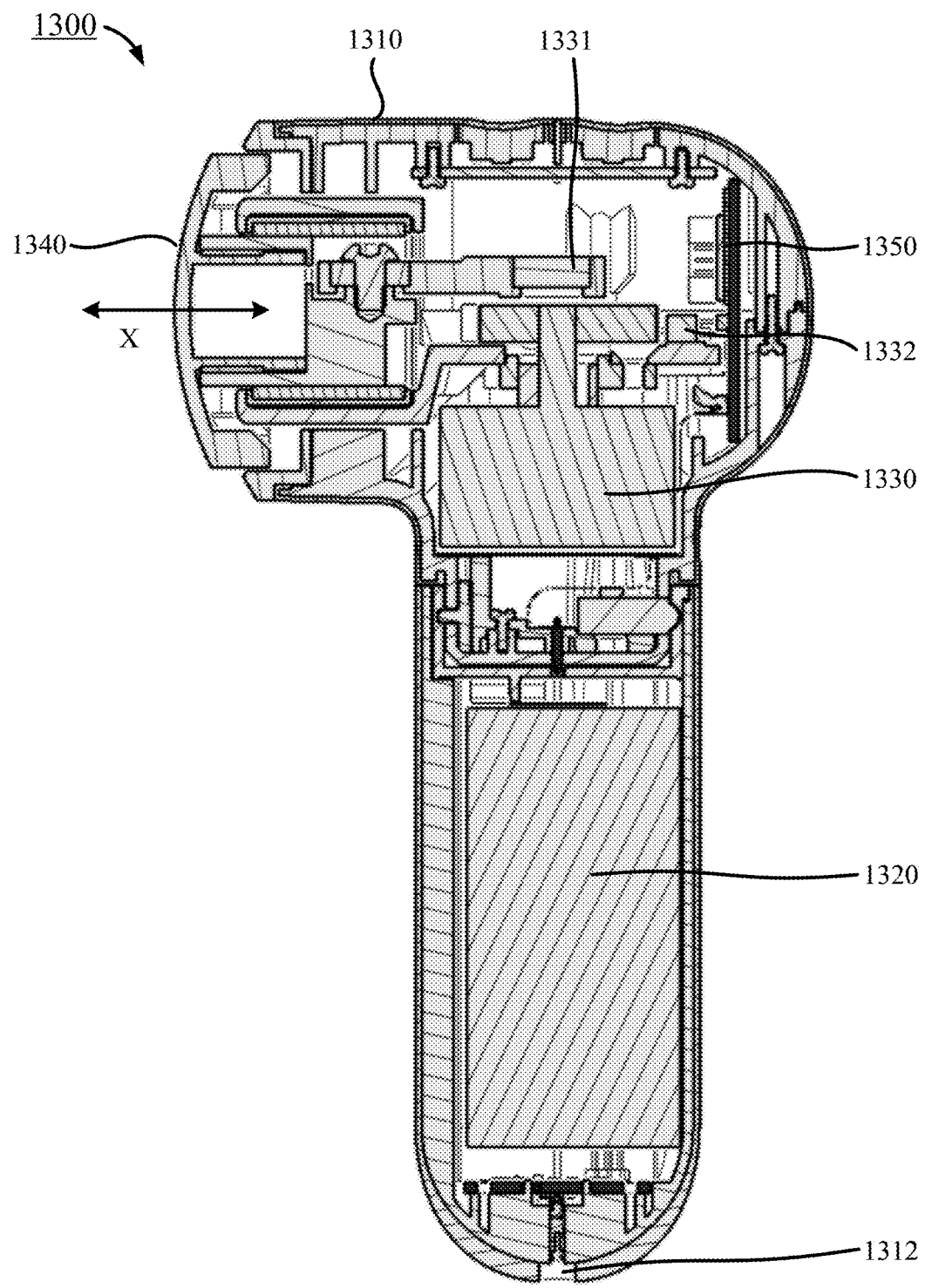
FIG. 21 is a cross-sectional view of the massager device of FIG. 20.
Figure 22:
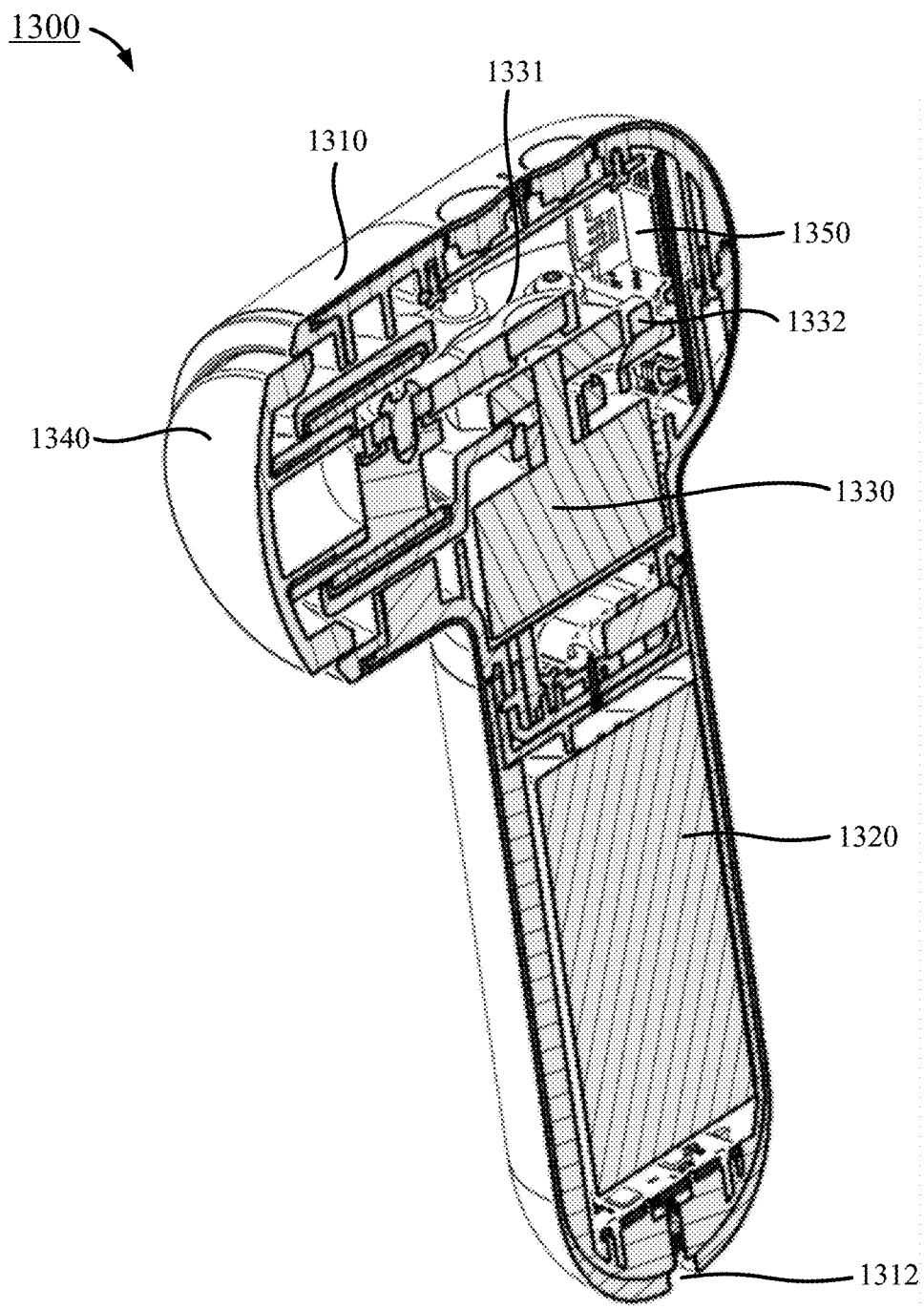
FIG. 22 is an angled cross-sectional view of the massager device of FIG. 20.

FIGS. 20-22 depict a massage or massager device 1300, according to embodiments. FIG. 20 depicts a perspective view of the massage device 1300, and FIGS. 21 and 22 depict sectional views of the massage device 1300. The massage device 1300 can include components that are structurally and/or functionally similar to other devices described herein, including massage management device 100, massage device 900, etc. For example, the massage device 1300 can include a housing 1310, an output mechanism 1340, a sensor 1332, a driving mechanism 1330, a control unit 1350, and a power source 1320. Thus, portions and/or components of the massage device 1300 may not be described again in detail herein.

The driving mechanism 1330 of the massage device 1300 can include an electric motor, such as, for example, a Lorentz force motor, a brushless DC motor, or brushed DC motor. As depicted in FIGS. 21 and 22, the electric motor can be a rotary motor that is configured to rotate to drive a linear movement of the output mechanism 1340 along an axis X. The electric motor can be coupled to the output mechanism 1340 via a crank-shaft 1331 (and one or more fasteners or other mechanical components). The electric motor can be configured to generate a high force and/or long stroke or displacement output.

The output mechanism 1340 can be structurally and/or functionally similar to other output mechanisms 1340 described herein. In some embodiments, the output mechanism 1340 can be constrained to move along the axis X, e.g., via channels, grooves, or other mechanical structures formed in or disposed within housing 1310.

The housing 1310 can be configured to separate into two portions, e.g., a top or first portion 1313 that defines one or more first compartments and a bottom or second portion 1314 that defines one or more second compartments. The first and second portions 1313, 1314 can be removably attached to one another, e.g., via a twist-on and twist-off arrangement. The first portion 1313 can be configured to house a majority of the internal circuitry and components of the massage device 1300, including, for example, the driving mechanism 1330, the sensor 1332, the control unit 1350, and a portion of the output mechanism 1340. The first portion 1313 can define an opening through which the output mechanism 1340 can extend out of the first portion 1313 of the housing 1310 and contact with tissue, such that the output mechanism 1340 can apply a mechanical output to tissue and/or muscle. The output mechanism 1340 can be configured to move along a longitudinal axis of the first portion 1313 of the housing 1310. The second portion 1314 can be configured to house the power source 1320. As such, the second portion 1314 can be removed from the first portion 1313 to allow for easy access and/or replacement of the power source 1320. The second portion 1314 can also include a port or interface 1312 for receiving an electronic connector, e.g., for coupling an external power source to the power source 1320 to facilitate recharging of the power source 1320, for operatively coupling an external power source to other components of the massage device 1300 for powering such components, and/or for coupling one or more other external devices or components to one or more components of the massage device 1300 (e.g., a user device, a compute device, a third-party device, etc., as described with reference to FIG. 11).

The sensor 1332 can be configured to measure a movement such as velocity and/or acceleration of the housing 1310. In particular, the sensor 1332 can be coupled to the housing 1310 and can detect when the housing 1310 is moving, which can indicate that the massager device 1300 is not providing the desired muscle treatment and/or therapy. For example, a user may have pressed the output mechanism 1340 of the massager device 1300 too much against a region of tissue or the massager device 1300 is pushing against bone or other hard structure, which causes the housing 1310 of the massager device 1300 to move together with the output mechanism 1340. As such, the sensor 1332 by detecting the velocity or acceleration of the housing 1310, can inform the control unit 1350 (or another device that is operatively coupled to the massage device 1300, such as, for example, user device 1180, compute device(s) 1190, third-party device(s) 1185, and/or other devices, as described below with reference to FIG. 11) that the massage device

1300 is not delivering the necessary massage treatment and/or needs to be adjusted (e.g., to move off of bone and/or press less firmly against the muscle). In some embodiments, the data captured by the sensor 1332 can be received by the control unit 1350 and can be used to adjust one or more parameters of the operation of the driving mechanism 1330 (e.g., by sending electrical signals to the driving mechanism 1330).

Figure 23:
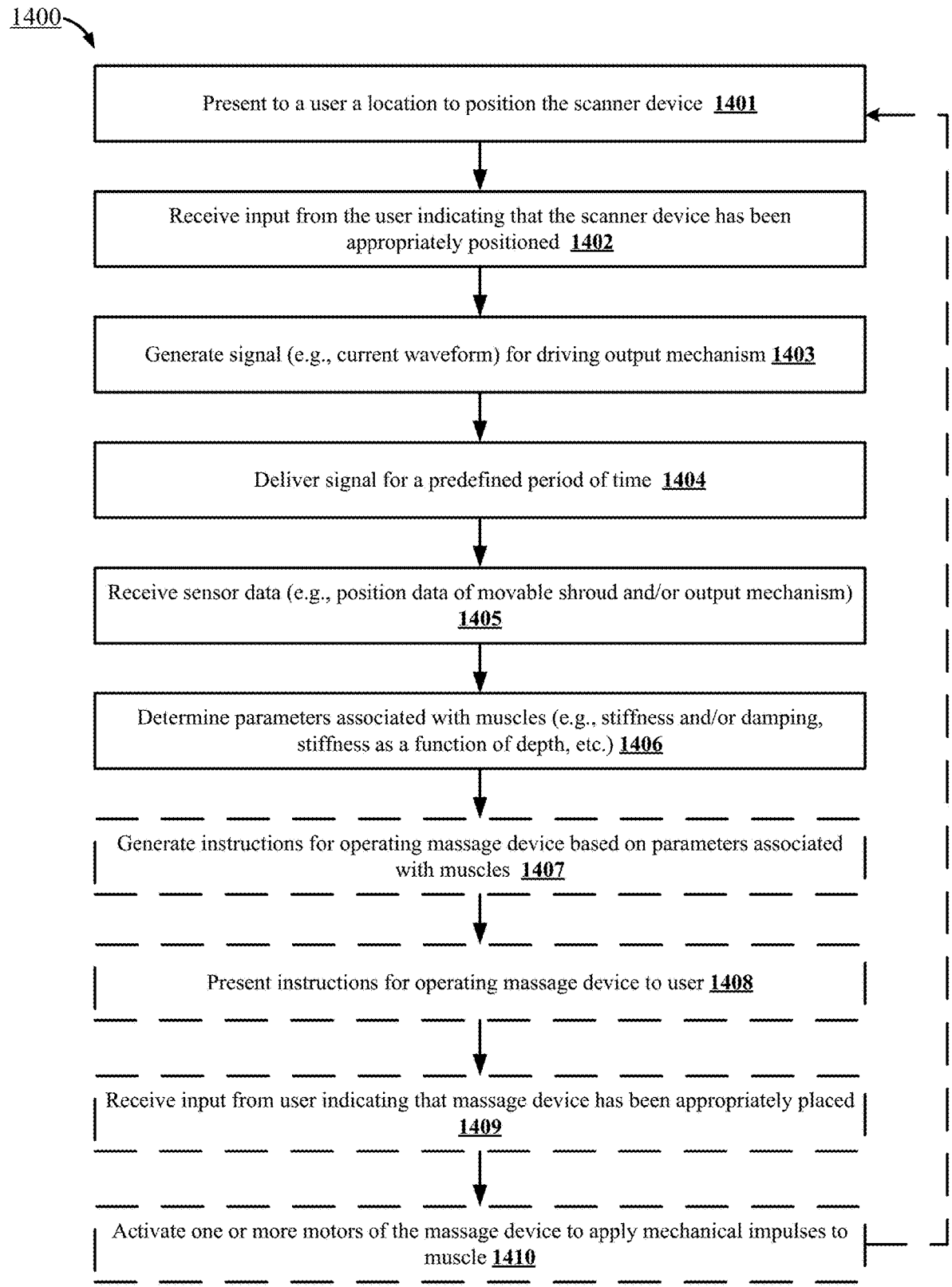
FIG. 23 is a flow chart of an example method performed by a muscle measurement device, according to an embodiment.

FIG. 23 depicts an example method 1400 of operating the systems and devices described herein, according to embodiments. Method 1400 can be performed by one or more of the muscle management devices, muscle measurement devices, muscle treatment devices, and/or systems thereof described herein.

Method 1400 can include presenting to a user a location for positioning a muscle measurement or scanner device (or muscle management device equipped with measurement capabilities), at 1401. For example, a compute device (e.g., compute device 1190) and/or a user device (e.g., a user device 1180) can present information to a user indicating to the user where to position a muscle measurement device on the user's body. In some embodiments, the compute device can send instructions to the user device to cause the user device to present (e.g., display via an application interface) such information to a user. Alternatively, the user device can have such instructions stored therein and can present such instructions to the user (e.g., via an application interface). In some embodiments, a muscle measurement device (or a muscle management device) can present such instructions to the user, e.g., via an onboard display or other output device (e.g., an I/O device of a control unit). The muscle measurement device (or muscle management device) can receive such instructions from an external compute device (e.g., the user device or the compute device) to present to the user or can have such instructions stored onboard a memory of the muscle measurement device (or muscle management device). In some instances, the instructions can involve instructing the user to position the muscle measurement device (or muscle management device) at a specific location on the body of the user. In some embodiments, the instructions can involve instructing the user to position the muscle measurement device (or muscle management device) at a series of locations on the body of the user or to move the muscle measurement device (or muscle management device) according to a plan or sequence along a portion of the body of the user. In some embodiments, the instructions can involve instructing the user to position the muscle measurement device (or muscle management device) at a predetermined orientation relative to and/or with a predetermined depth or pressure against the skin of the user.

At 1402, a signal can be received that indicates that the muscle measurement device (or muscle management device) has been appropriately positioned against a skin of the user. The signal can be received at one or more devices, including, for example, the muscle measurement device (or muscle management device), the user device, and/or the compute device. In some embodiments, the signal can indicate that the muscle measurement device (or muscle management device) has been placed at an appropriate position (e.g., with sufficient pressure or depth against the user's skin) and/or appropriate orientation. In some embodiments, the signal can be an input provided by the user, e.g., via an I/O device of the muscle measurement device (or muscle management device) or the user device. In some embodiments, the signal can be automatically generated by the muscle measurement device (or muscle management device) in response to detecting that a portion of the muscle measurement device (or muscle management device), such as, for example, an output mechanism, end effector, and/or shroud, has been placed at an appropriate position and/or orientation relative to the user's target muscle area. Such detection can be conducted by one or more sensors disposed on or coupled to the muscle measurement device (or muscle management device).

At 1403, a signal (e.g., a current waveform) can be generated for driving movement of an output mechanism or end effector of the muscle measurement device (or muscle management device). The signal can be, for example, a periodic signal or more complex waveform. FIGS. 7A-7C provide some examples of example waveforms. The signal can be delivered to a drive mechanism of the muscle measurement device (or muscle management device) for a predetermined or predefined period of time (e.g., about 2 second to about 5 minutes). During this predetermined period, sensor(s) disposed on the muscle measurement device (or muscle management device) can be configured to measure one or more properties of the output mechanism or other portions of the muscle measurement device (or muscle management device). In some embodiments, a first sensor (e.g., sensor 1042) can be configured to measure a property (e.g., position) of the output mechanism, while a second sensor (e.g., sensor 1032) can be configured to measure a property (e.g., position) of a movable or moving shroud. In some embodiments, a sensor (e.g., sensor 132) can be configured to measure a position, velocity, acceleration, and/or force associated with the output mechanism. Sensor data from the sensor(s) can be received, at 1405.

At 1406, one or more parameters or characteristics associated with the muscles can be determined, e.g., by the muscle measurement device (or muscle management device), the user device, or the compute device. These parameters can include, for example, one or more biomechanical properties of the tissue and/or muscle area, such as, a stiffness of the muscle area, an elasticity of the muscle area, a damping of the muscle area, and/or such parameters as a function of depth and/or time. For example, in embodiments where the muscle measurement device (or muscle management device) is used to collect sensor data for an extended period of time, the muscle measurement device (or muscle management device), user device, and/or compute device can be configured to measure or determines one or more characteristics of the muscle area as a function of time. In embodiments where the muscle measurement device (or muscle management device) is used to collect position or depth data associated with the output mechanism (e.g., with the use of a movable or moving shroud), the muscle measurement device (or muscle management device), user device, and/or compute device can be configured to measure or determine one or more characteristics of the muscle area as a function of depth.

The parameters or characteristics of the muscle determined by the devices and systems described herein can be stored, e.g., on an onboard memory of the muscle measurement device (or muscle management device), the user device, and/or the compute device, e.g., for future reference by the user, a caretaker of the user, a therapist, or other individuals monitoring information about the user and/or providing treatment to the user.

Optionally, the muscle measurement device (or muscle management device), user device, and/or compute device can be configured to generate instructions for operating a massage or muscle treatment device (or muscle management device equipped with muscle treatment functionality), at 1407. In particular, instructions can be generated for operating the massage device (or muscle management device) based on the parameters or characteristics measured of the muscle. Such instructions can be optionally presented to a user, at 1408. For instance, the user device, the compute device, and/or the massage device (or muscle management device) can present instructions for operating the massage device (or muscle management device) to the user. In some embodiments, the compute device such as a back-end compute device can generate and send the relevant instructions for operating the massage device (or muscle management device) to the user device and/or the massage device (or muscle management device), and have such device(s) present the instructions to the user. In some embodiments, the user device and/or massage device (or muscle management device) can generate such instructions (e.g., based on internally stored instructions) and present such instructions to the user. The instructions can include instructions for placing the massage device (or muscle management device) at an appropriate position, depth, and/or orientation relative to the muscle area.

At 1409, a signal can be received that indicates that the massage device (or muscle management device) has been appropriately places relative to the muscle area of the user. The signal can be received at one or more devices, including, for example, the massage device (or muscle management device), the user device, and/or the compute device. In some embodiments, the signal can indicate that the massage device (or muscle management device) has been placed at an appropriate position (e.g., with sufficient pressure or depth against the user's skin) and/or appropriate orientation. In some embodiments, the signal can be an input provided by the user, e.g., via an I/O device of the massage device (or muscle management device) or the user device. In some embodiments, the signal can be automatically generated by the massage device (or muscle management device) in response to detecting that a portion of the massage device (or muscle management device) such as, for example, an output mechanism, has been placed at an appropriate position and/or orientation relative to the user's target muscle area. Such detection can be conducted by one or more sensors disposed on or coupled to the massage device (or muscle management device).

At 1410, the massage device (or muscle management device) can activate one or more actuators or motors of the massage device to apply mechanical impulses to the muscle. In some embodiments, one or a plurality of actuators can be activated to drive a movement of the massage device (or muscle management device). In some embodiments, a signal waveform can be generated to activate the movement of the output mechanism of the massage device (or muscle management device). Such mechanical impulses, when applied to the muscle, can treat one or more conditions of the muscle, as reflected by the parameters of the muscle measured at 1406.

In some embodiments, the method 1400 can repeat, as necessary, for targeting multiple locations or muscle areas of the user and/or to target particular locations multiple times.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The invention claimed is:

1. An apparatus, comprising:
    a housing;
    a movable shroud including a surface configured to contact a tissue area, the movable shroud configured to displace relative to the housing in response to being pressed against the tissue area;
    an output mechanism configured to displace relative to the housing, the output mechanism including an end effector configured to apply a mechanical output to the tissue area when the movable shroud is pressed against the tissue area;
    a driving mechanism coupled to the output mechanism, the driving mechanism configured to drive mechanical motion of the output mechanism to produce the mechanical output;
    a first sensor configured to measure a property associated with the output mechanism when the output mechanism is applying the mechanical output;
    a second sensor configured to measure a position of the movable shroud when the movable shroud is pressed against the tissue area; and
    a processor operatively coupled to the first and second sensors and the driving mechanism, the processor configured to:

control the driving mechanism to drive movement of the output mechanism for a predetermined period of time;

receive, from the first sensor during the predetermined period of time, first data representative of the property over time;

receive, from the second sensor, second data representative of the position of the movable shroud; and determine, based on the first and second data, a characteristic of the tissue area of the user.

2. The apparatus of claim 1, wherein the housing houses the driving mechanism and the first and second sensors, the housing defining an opening through which a portion of the output mechanism extends.

3. The apparatus of claim 1, further comprising a fixed shroud that is coupled to an exterior of the housing and forms an annular wall around the portion of the output mechanism.

4. The apparatus of claim 3, wherein the fixed shroud and the movable shroud are disposed concentrically around the portion of the output mechanism.

5. The apparatus of claim 3, wherein the output mechanism in an extended position is configured to extend a greater distance from the housing than the fixed shroud, the output mechanism configured to displace toward the housing when the surface of the fixed shroud is placed against the tissue area.

6. The apparatus of claim 1, wherein the processor is configured to receive an input or signal indicative of the movable shroud being placed against the tissue area, the processor configured to control the driving mechanism in response to receiving the input or signal.

7. The apparatus of claim 1, wherein:
the characteristic of the tissue area includes a stiffness of a muscle area;
the second data representative of the position of the movable shroud include position data representative of the position of the movable shroud over time; and
the processor is further configured to:
determine a depth extended by the output mechanism into the tissue area over time based on the position data; and
determine the stiffness of the muscle area as a function of depth based on the determined stiffness of the muscle area and the determined depth extended by the output mechanism.

8. The apparatus of claim 1, wherein:
the characteristic of the tissue area includes a damping of a muscle area;
the second data representative of the position of the movable shroud includes position data representative of the position of the movable shroud over time; and
the processor further configured to:
determine a depth extended by the output mechanism into the tissue area over time based on the position data; and
determine the damping of the muscle area over time based on the determined damping of the muscle area while accounting for variations in the determined depth extended by the output mechanism over time.

9. The apparatus of claim 1, wherein the movable shroud is mounted to a cage, the cage including a plurality of compressible members that are configured to depress in a direction along a longitudinal axis of the output mechanism in response to a displacement of the movable shroud while reducing movement of the movable shroud in directions other than the direction along the longitudinal axis of the output mechanism.

10. The apparatus of claim 1, further comprising one or more compliant elements, the one or more compliant elements being coupled to the output mechanism at different spaced locations and being configured to reduce a movement of the output mechanism in directions other than a direction along a longitudinal axis of the output mechanism.

11. The apparatus of claim 10, wherein the one or more compliant elements include one or more flexures,
each flexure having a planar structure that has relatively low stiffness in a direction normal to a surface of the planar structure and relatively high stiffness in directions parallel to the surface of the planar structure, such that the flexure, when positioned to extend outwardly from the output mechanism, is configured to facilitate displacement of the output mechanism in the direction along the longitudinal axis of the output mechanism while reducing the movement of the output mechanism in directions other than the direction along the longitudinal axis of the output mechanism.

12. The apparatus of claim 1, wherein the processor is configured to generate, via a signal generator, a time-varying waveform for controlling the driving mechanism to drive the movement of the output mechanism.

13. The apparatus of claim 1, wherein the end effector has a convex surface.

14. The apparatus of claim 1, wherein the predetermined period of time is a first predetermined period of time, the processor further being configured to:
control the driving mechanism to drive movement of the output mechanism for a second predetermined period of time to apply treatment to the muscle area based at least in part on the characteristic of the muscle area.

15. The apparatus of claim 1, wherein the predetermined period of time is between about 2 seconds and about 5 minutes.

16. An apparatus, comprising:
an output mechanism including an end effector configured to displace relative to a tissue area to apply a mechanical output to the tissue area;
a driving mechanism coupled to the output mechanism, the driving mechanism configured to drive displacement of the output mechanism along a longitudinal axis of the output mechanism to produce the mechanical output;
a plurality of compliant elements coupled to the output mechanism at different spaced locations along the longitudinal axis, each compliant element of the plurality of compliant elements having low on-axis stiffness and high off-axis stiffness such that the compliant element allows the displacement of the output mechanism along a direction of the longitudinal axis while reducing movement of the output mechanism in other directions;
a sensor configured to measure a property associated with the output mechanism; and
a processor operatively coupled to the sensor and the driving mechanism, the processor configured to:
control the driving mechanism to drive the displacement of the output mechanism for a predetermined period of time;
receive, from the sensor during the predetermined period of time, data representative of the property over time; and determine, based on the data over time, a characteristic of the muscle area of the user.

17. The apparatus of claim 16, wherein each compliant element of the plurality of compliant elements has a planar structure and extends outwardly from the output mechanism.

18. The apparatus of claim 16, wherein each compliant element of the plurality of compliant elements has a cut pattern that contributes to the low on-axis stiffness of the compliant element.

19. The apparatus of claim 16, wherein each compliant element of the plurality of compliant elements is a circular disc.

20. The apparatus of claim 16, wherein the plurality of compliant elements includes at least two compliant elements where a first compliant element is positioned near a first end of the output mechanism and a second compliant element is positioned near a second, opposite end of the output mechanism.

21. The apparatus of claim 16, further comprising a shroud disposed around at least a portion of the output mechanism, the shroud including a surface configured to contact the tissue area.

22. The apparatus of claim 21, wherein the processor is configured to receive an input or signal indicative of the shroud being placed against the tissue area,
the processor configured to control the driving mechanism in response to receiving the input or signal.

23. The apparatus of claim 16, further comprising a housing, the output mechanism configured to displace relative to the housing,
each compliant element of the plurality of compliant elements having an outer portion that is coupled to the housing and a central portion that is configured to displace to enable the displacement of the output mechanism.

24. The apparatus of claim 23, further comprising a movable shroud configured to displace relative to the housing,
the movable shroud configured to form an annular wall that is disposed around at least one of the plurality of compliant elements.

25. A method, comprising:
receiving, from a first sensor, first data representative of a property associated with an output mechanism of a measurement device that is configured to apply a mechanical output to a tissue area during a predetermined period of time;
receiving, from a second sensor, second data representative of a position of a movable shroud of the measurement device, the movable shroud configured to displace in response to being pressed against the tissue area during the predetermined period of time; and
determining, based on the first and second data, a characteristic of the tissue area during the predetermined period of time.

26. The method of claim 25, further comprising:
controlling a driving mechanism of the measurement device to drive movement of the output mechanism during the predetermined period of time, the predetermined period of time is between about 30 seconds and about 5 minutes.

27. The method of claim 25, further comprising:
determining a depth extended by the output mechanism into the tissue area based on the second data representative of the position of the movable shroud.

28. The method of claim 27, wherein the characteristic of the tissue area includes a stiffness of a muscle area, the method further comprising:
determining the stiffness of the muscle area as a function of depth based on the determined stiffness of the muscle area and the determined depth extended by the output mechanism.

29. The method of claim 27, wherein the characteristic of the tissue area includes a stiffness of a muscle area, the method further comprising:
determining a damping of the muscle area as a function of depth based on the determined stiffness of the muscle area and the determined depth extended by the output mechanism over time.

30. The method of claim 25, wherein the receiving the first and second data from the first and second sensors is while the measurement device is moved along a portion of the body of a user.

* * * * *